United States Patent [19]

Cochran et al.

[11] 4,200,926
[45] Apr. 29, 1980

[54] ELECTRONIC CALCULATOR IMPLEMENTED IN SEMICONDUCTOR LSI CHIPS WITH SCANNED KEYBOARD AND DISPLAY

[75] Inventors: Michael J. Cochran; Jerry L. Vandierendonck, both of Houston, Tex.

[73] Assignee: Texas Instruments Incorporated, Dallas, Tex.

[21] Appl. No.: 444,226

[22] Filed: Feb. 20, 1974

Related U.S. Application Data

[63] Continuation of Ser. No. 255,856, May 22, 1972.

[51] Int. Cl.² .................... G06F 3/02; G06F 7/48
[52] U.S. Cl. ........................... 364/200; 340/365 S
[58] Field of Search ............. 340/172.5, 365 S; 445/1; 364/200 MS File, 900 MS File, 709, 710

[56] References Cited

U.S. PATENT DOCUMENTS

| | | | |
|---|---|---|---|
| 3,341,819 | 9/1967 | Emerson | 340/172.5 |
| 3,360,781 | 12/1967 | Boehnke | 340/172.5 |
| 3,380,033 | 4/1968 | Cerny et al. | 340/172.5 |
| 3,453,601 | 7/1969 | Bogert et al. | 340/172.5 |
| 3,487,369 | 12/1969 | King et al. | 340/172.5 |
| 3,533,076 | 10/1970 | Perkins et al. | 340/172.5 |
| 3,579,201 | 5/1971 | Langley | 340/172.5 |
| 3,593,313 | 7/1971 | Tomaszewski et al. | 340/172.5 |
| 3,594,734 | 7/1971 | Wang et al. | 340/172.5 |
| 3,602,894 | 8/1971 | Igel et al. | 340/172.5 |
| 3,623,156 | 11/1971 | Osborne | 340/172.5 |
| 3,641,328 | 2/1972 | Osborne | 340/172.5 |
| 3,641,501 | 2/1972 | Lloyd et al. | 340/172.5 |
| 3,651,463 | 3/1972 | Rawson et al. | 340/172.5 X |
| 3,702,988 | 11/1972 | Haney et al. | 340/172.5 |
| 3,760,171 | 9/1973 | Wang et al. | 340/172.5 X |
| 3,781,852 | 10/1973 | White et al. | 340/172.5 X |
| 3,855,461 | 12/1974 | Stockwell | 340/172.5 |
| 3,855,577 | 12/1974 | Vandierendonck | 340/172.5 |
| 3,892,957 | 7/1975 | Bryant | 340/172.5 |

Primary Examiner—Mark E. Nusbaum
Attorney, Agent, or Firm—John G. Graham

[57] ABSTRACT

An electronic desk top calculator implemented in MOS/LSI technology and including a scanned keyboard input and display output. Data registers are provided in a sequentially addressed random access memory array, which is addressed by a commutator also used to generate encoded timing signals for other parts of the system and control logic. The keyboard input includes an interface register into which is entered key sense line information along with encoded timing information derived from the encoded timing signals. The contents of the interface register may be entered into the data registers or used to select an address in a program storage memory via a program counter. Bits may be read out in parallel from cells in the data registers and processed through an arithmetic logic unit and then re-entered in the same cells within a bit time or state time, so the data registers do not recirculate in the usual sense.

35 Claims, 67 Drawing Figures

OPERATIONS

| 12 | 11 | 10 | 9 | 8 | 7 | 6 | 5 | 4 | 3 | 2 | 1 | 0 | ← $l_x$ |
|---|---|---|---|---|---|---|---|---|---|---|---|---|---|
| 1 | $M_d$ MSB | $M_c$ | $M_b$ | $M_a$ LSB | SUB | $R_d$ MSB | $R_c$ | $R_b$ | $R_a$ LSB | $\Sigma_c$ MSB | $\Sigma_b$ | $\Sigma_a$ LSB | |
| | M | | | | | R | | | | Σ | | | |

BRANCHES

| 12 | 11 | 10 | 9 | 8 | 7 | 6 | 5 | 4 | 3 | 2 | 1 | 0 | ← $l_x$ |
|---|---|---|---|---|---|---|---|---|---|---|---|---|---|
| 0 | COND | MSB | | | | | | | | | | LSB | |

ADDRESS

*Fig. 4A*

| | | | $\Sigma_c$ $R_d$ $M_d$ | $\Sigma_b$ $R_c$ $M_c$ | $\Sigma_a$ $R_b$ $M_b$ | $R_a$ $M_a$ |
|---|---|---|---|---|---|---|
| Σ0, | R0, | M0 | 0 | 0 | 0 | 0 |
| Σ1, | R1, | M1 | 0 | 0 | 0 | 1 |
| Σ2, | R2, | M2 | 0 | 0 | 1 | 0 |
| Σ3, | R3, | M3 | 0 | 0 | 1 | 1 |
| Σ4, | R4, | M4 | 0 | 1 | 0 | 0 |
| Σ5, | R5, | M5 | 0 | 1 | 0 | 1 |
| Σ6, | R6, | M6 | 0 | 1 | 1 | 0 |
| Σ7, | R7, | M7 | 0 | 1 | 1 | 1 |
| | R8, | M8 | 1 | 0 | 0 | 0 |
| | R9, | M9 | 1 | 0 | 0 | 1 |
| | R10, | M10 | 1 | 0 | 1 | 0 |
| | R11, | M11 | 1 | 0 | 1 | 1 |
| | R12, | M12 | 1 | 1 | 0 | 0 |
| | R13, | M13 | 1 | 1 | 0 | 1 |
| | R14, | M14 | 1 | 1 | 1 | 0 |
| | R15, | M15 | 1 | 1 | 1 | 1 |

*Fig. 4B*

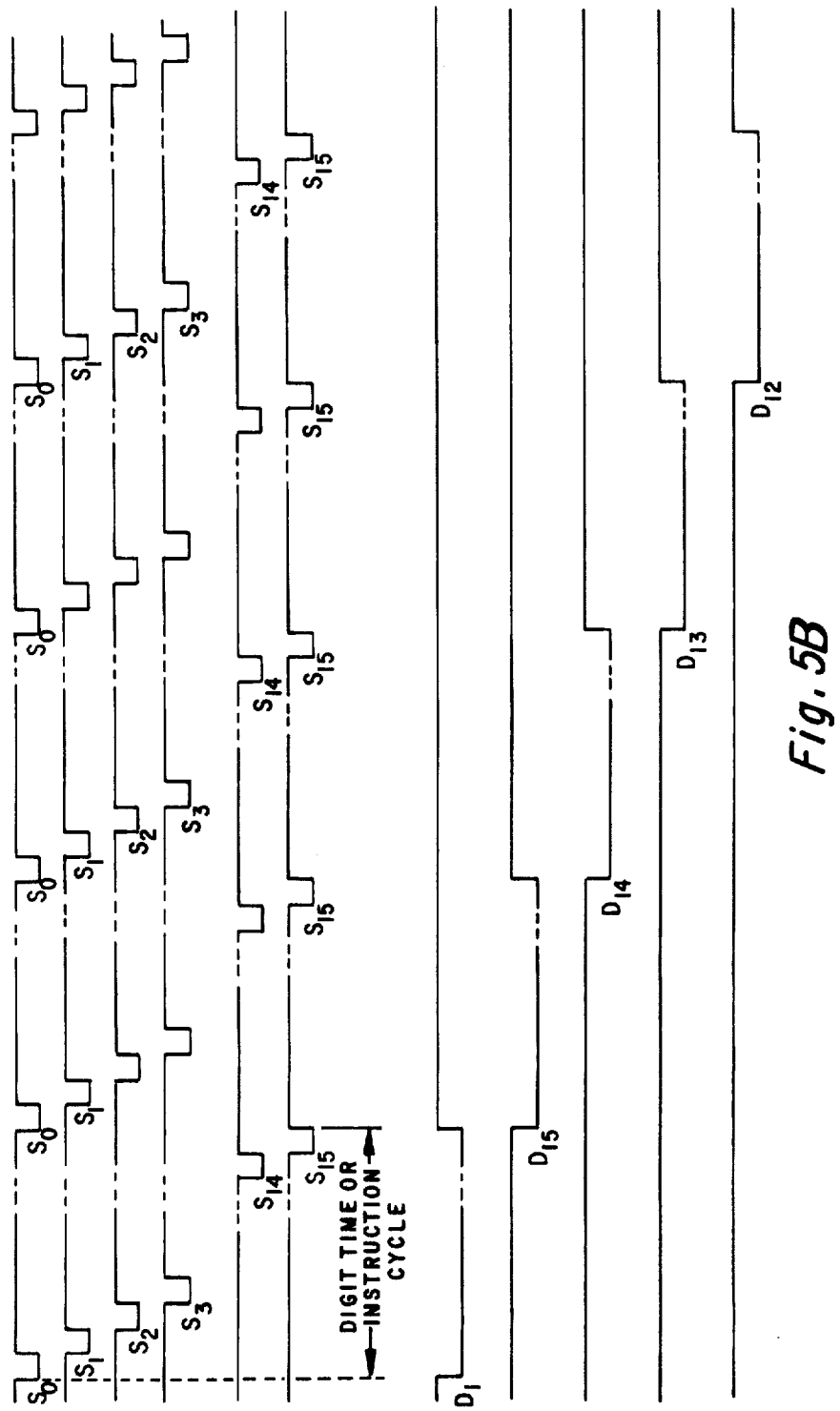

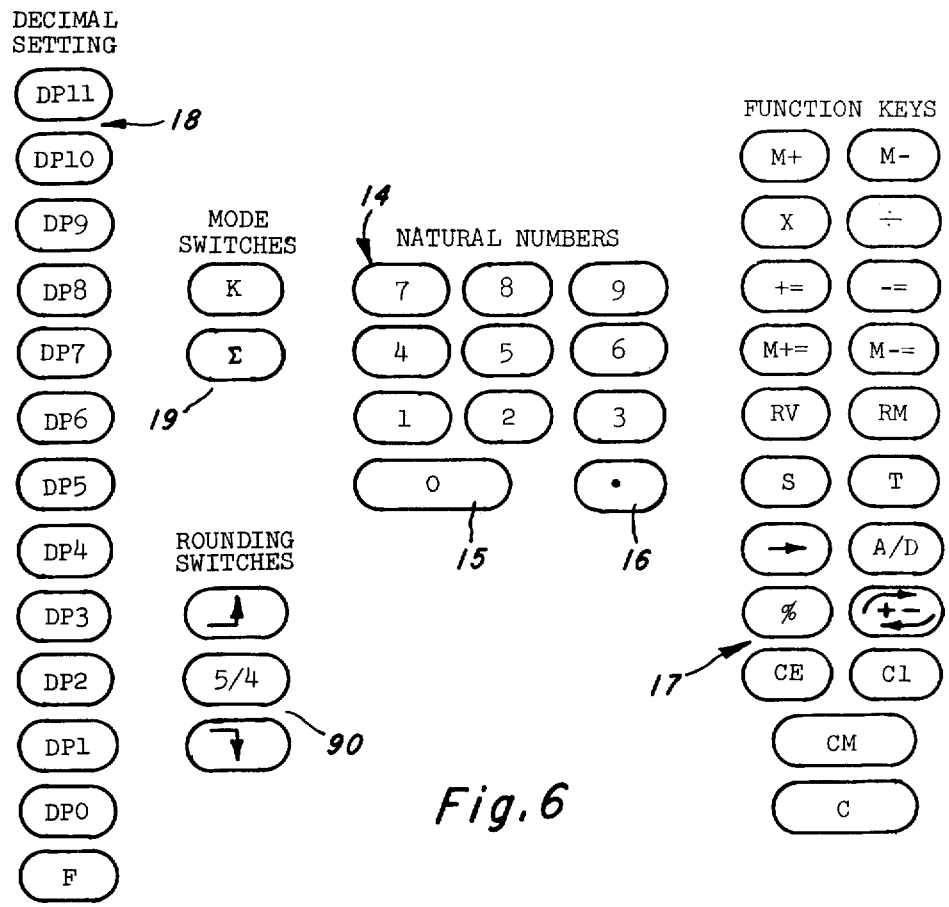
Fig. 6
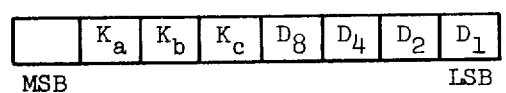
Fig. 8A
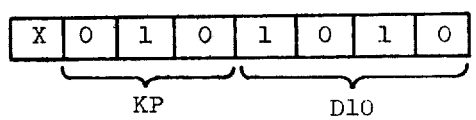
Fig. 8C
| K - line | Ka | Kb | Kc |
|---|---|---|---|
| KN | 0 | 0 | 0 |
| KO | 0 | 0 | 1 |
| KP | 0 | 1 | 0 |
| KQ | 0 | 1 | 1 |
| KR | 1 | 0 | 0 |
| KS | 1 | 0 | 1 |
| KT | 1 | 1 | 0 |
Fig. 8B

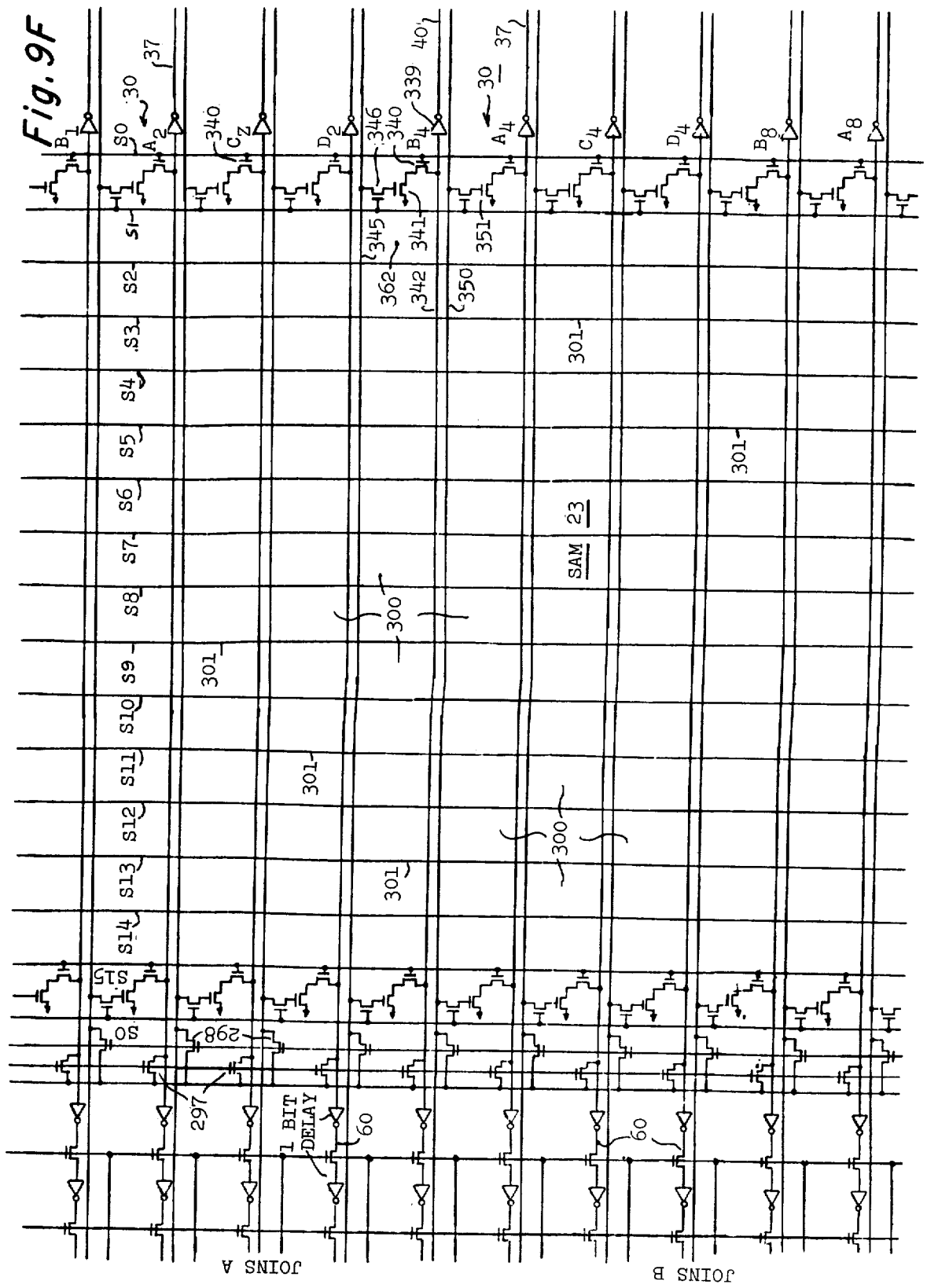

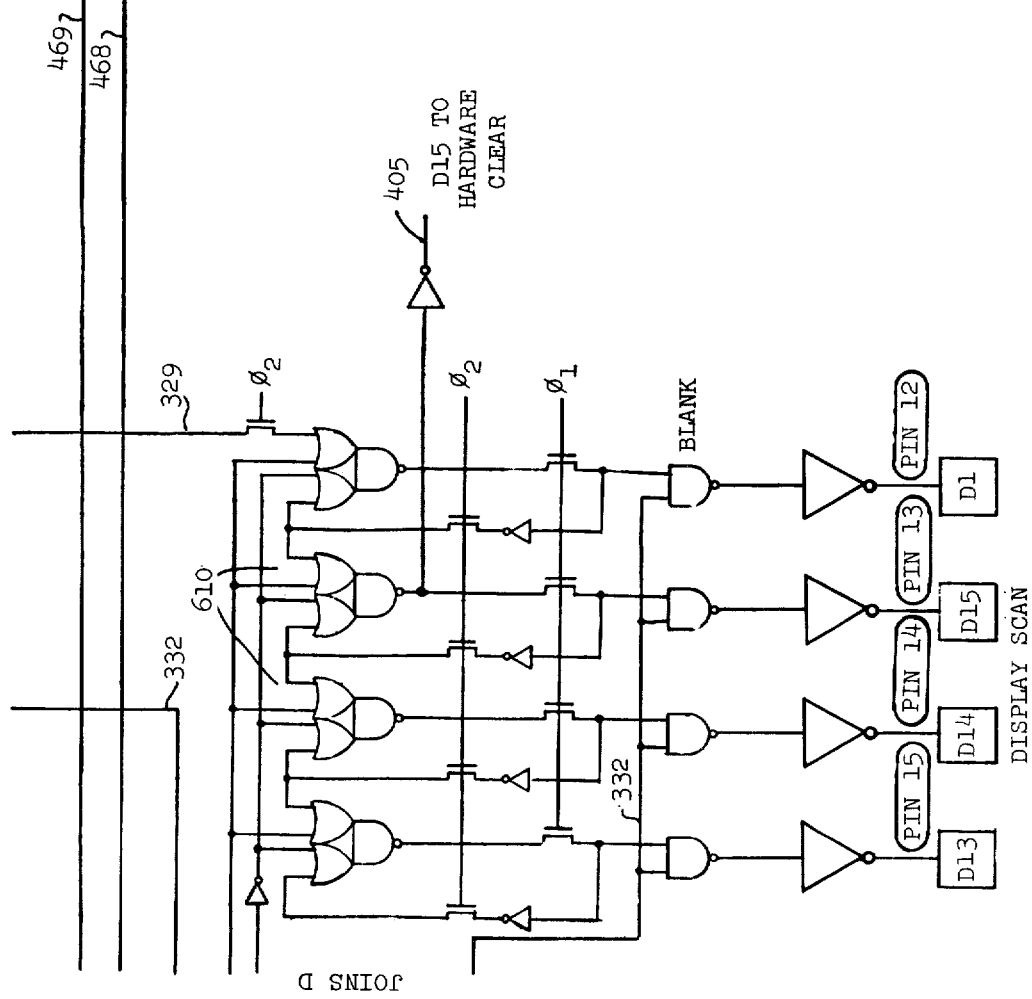

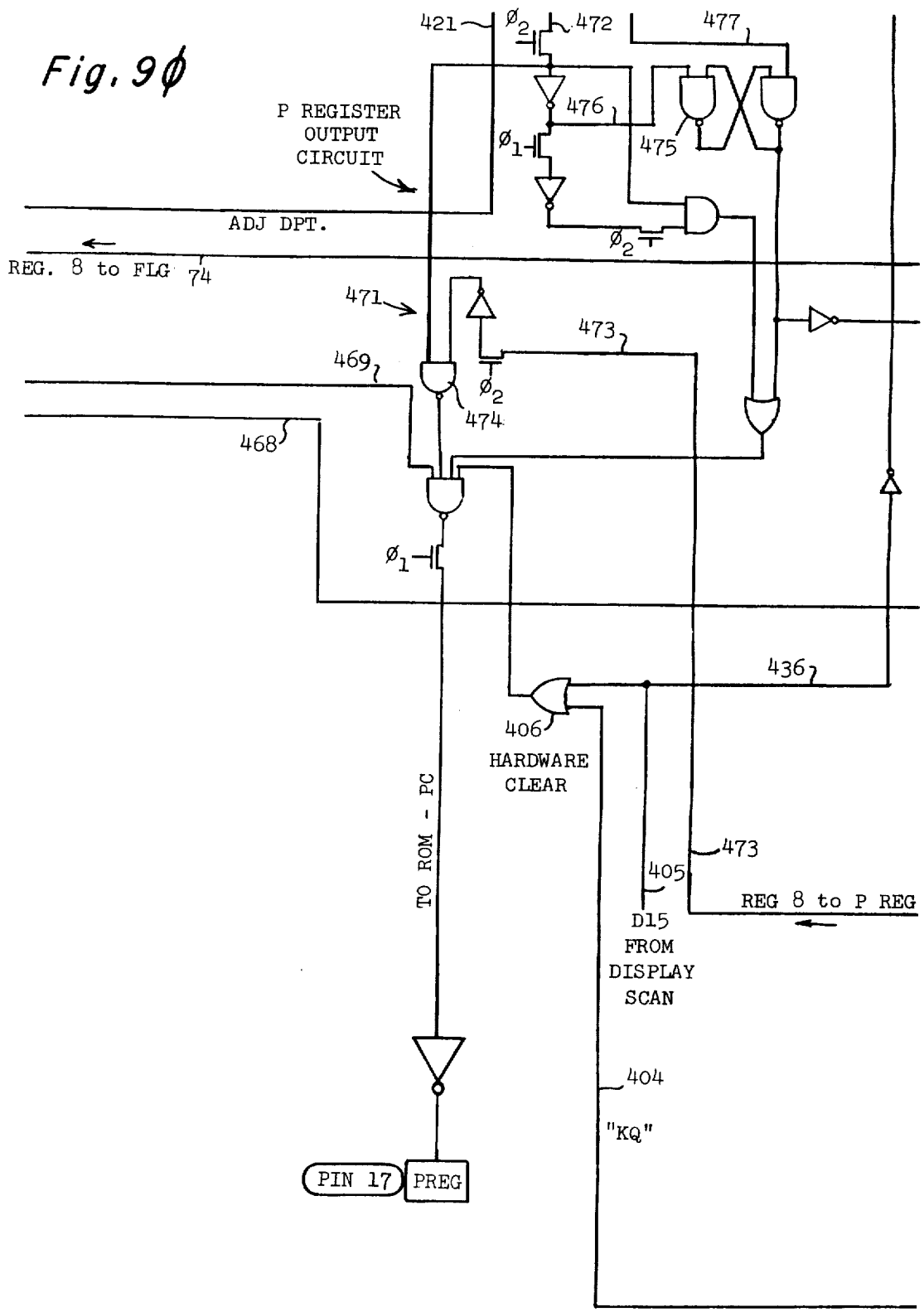
Fig. 9∅

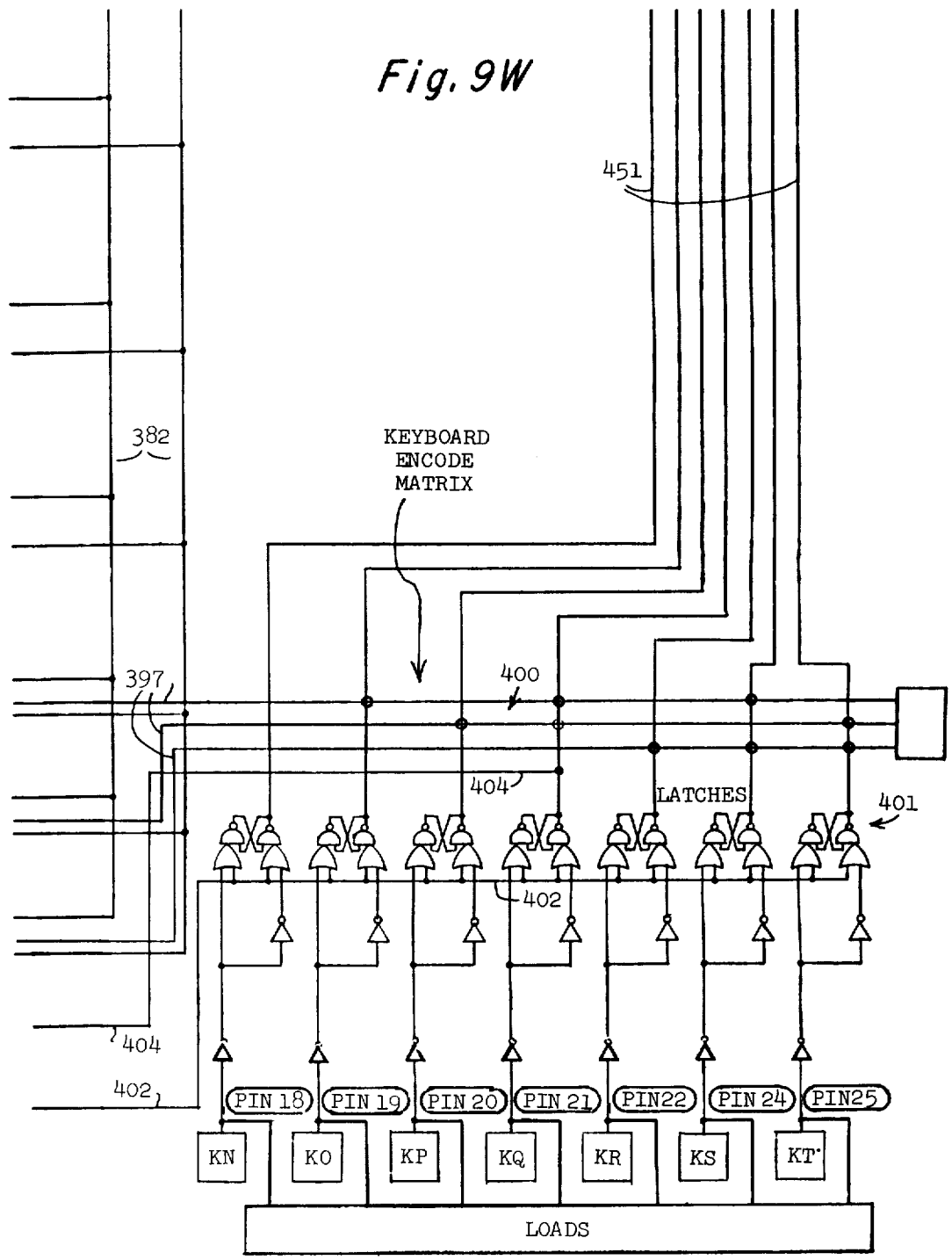

Fig. 10B

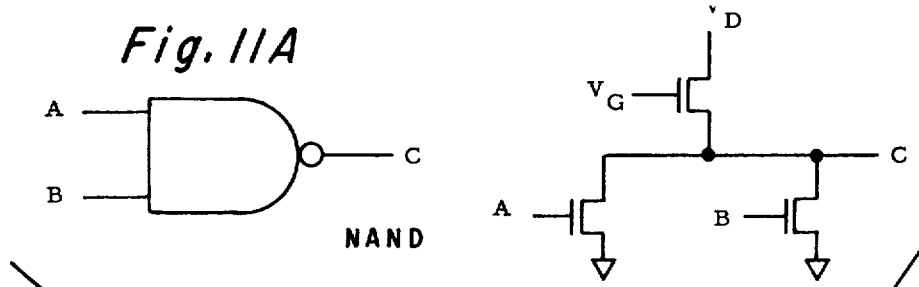
Fig. 11A
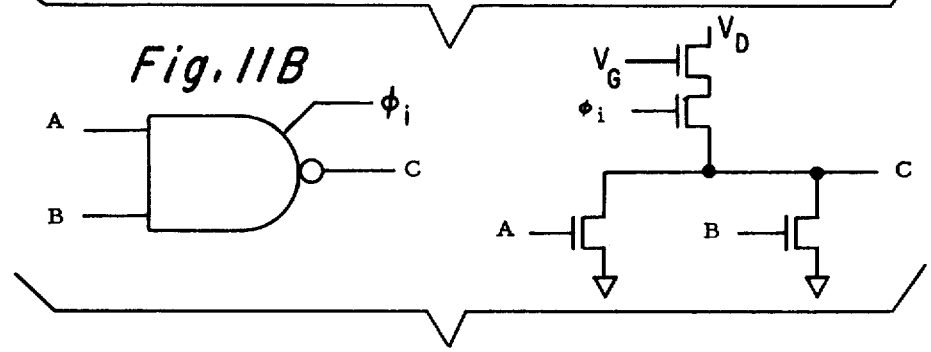
Fig. 11B
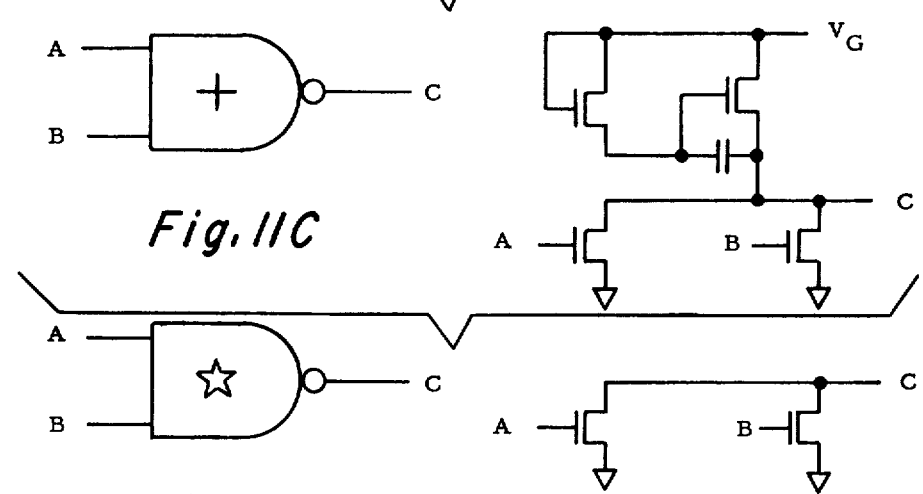
Fig. 11C
Fig. 11D
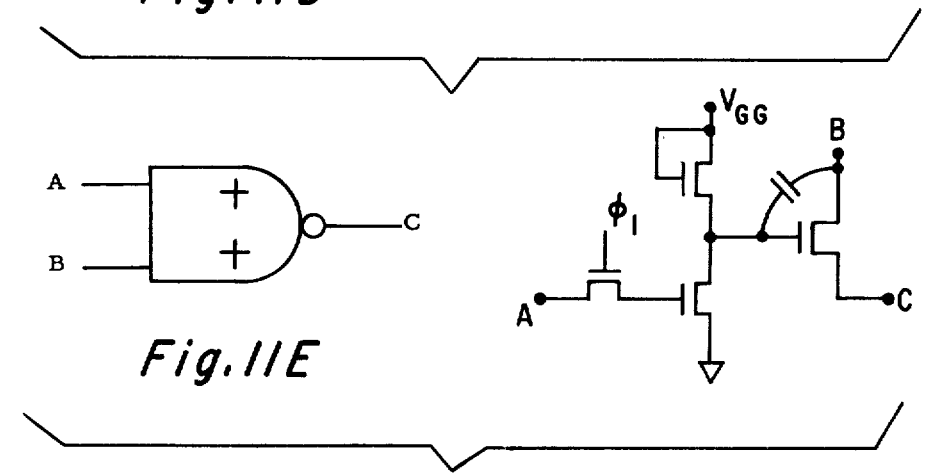
Fig. 11E

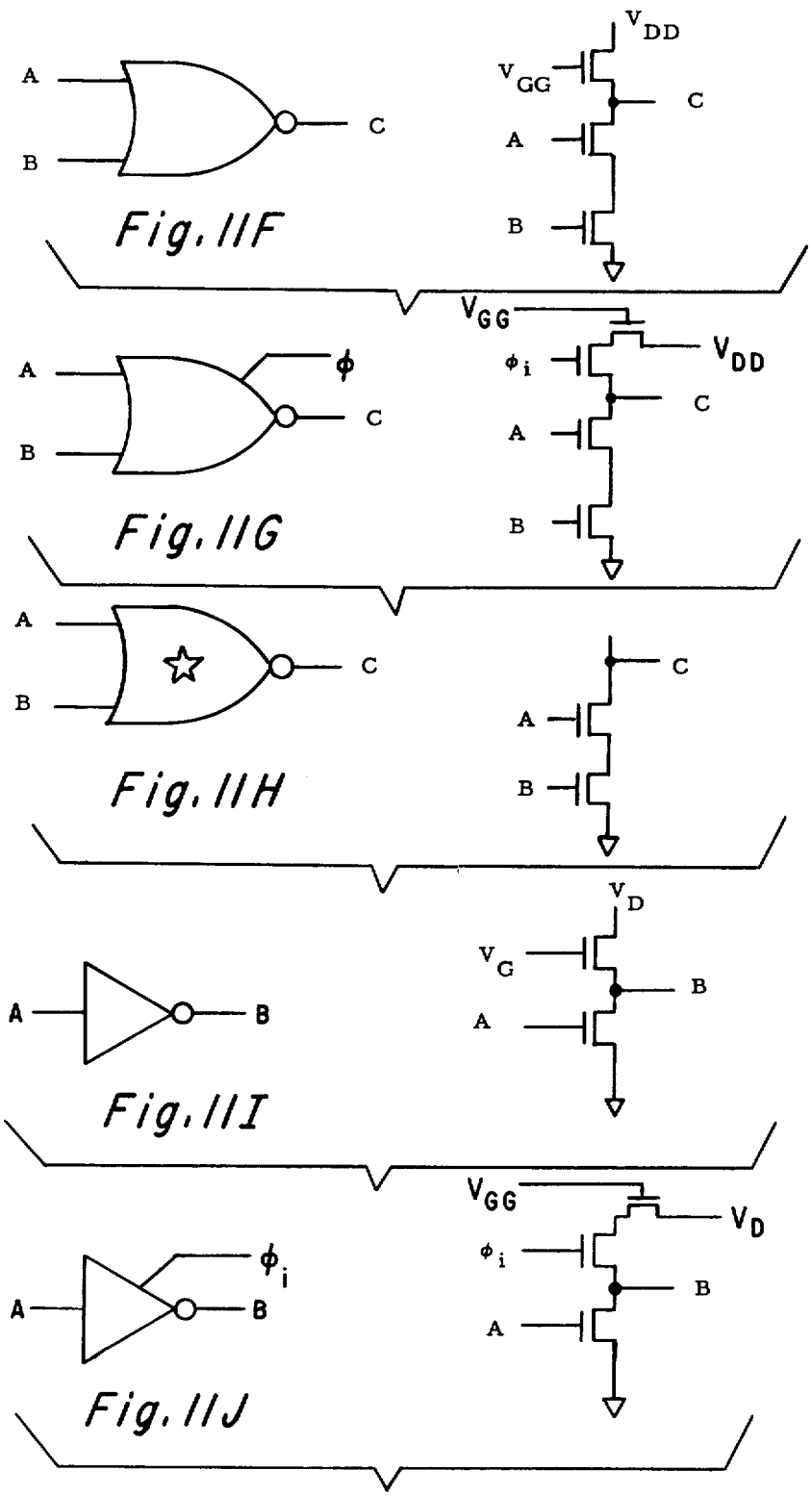

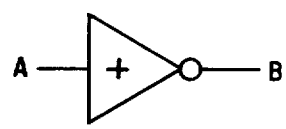 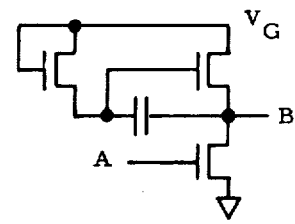
*Fig. 11K*
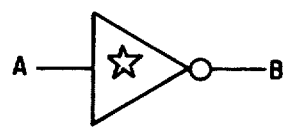 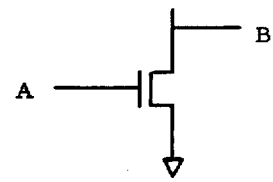
*Fig. 11L*
*Fig. 11M*
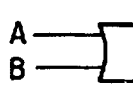 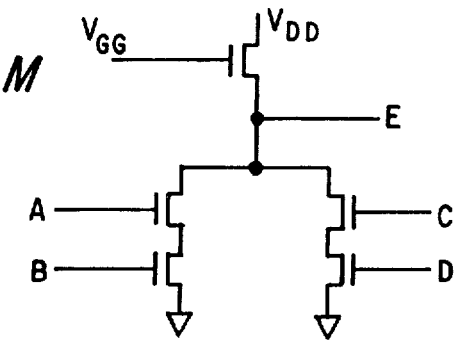
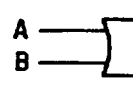 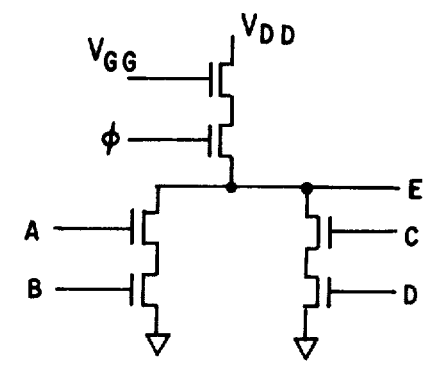
*Fig. 11N*

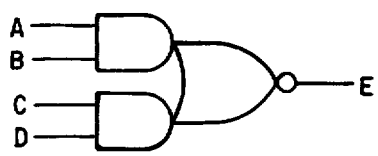
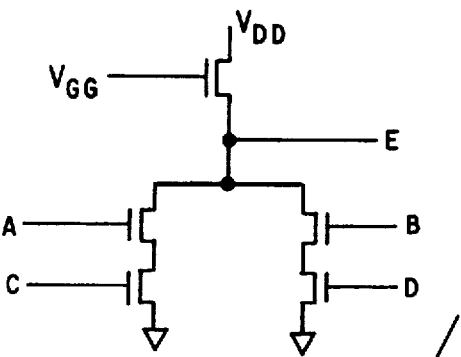
Fig. 11∅
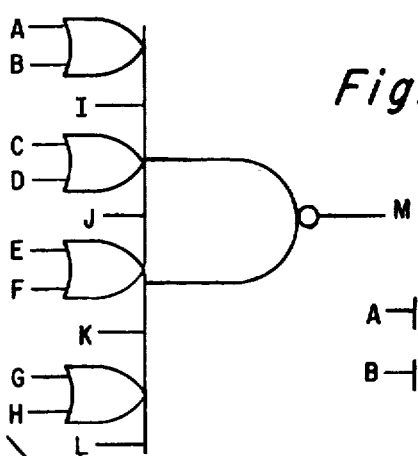
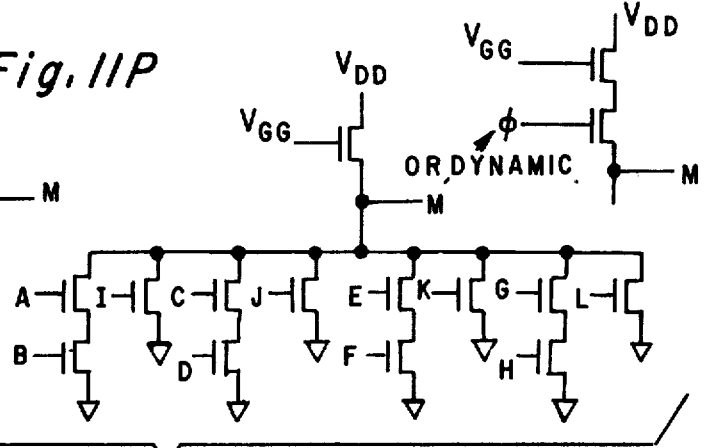
Fig. 11P
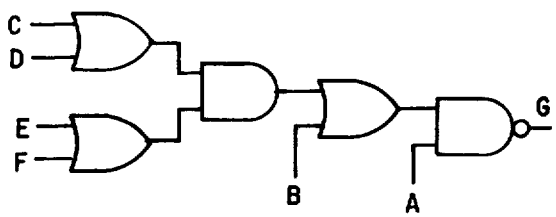
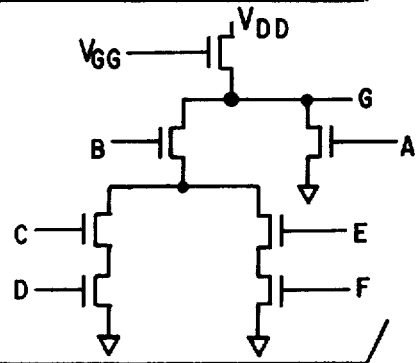
Fig. 11Q
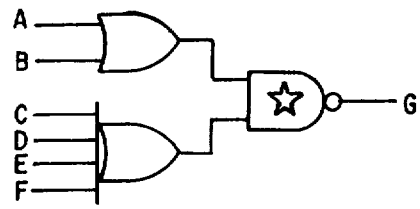
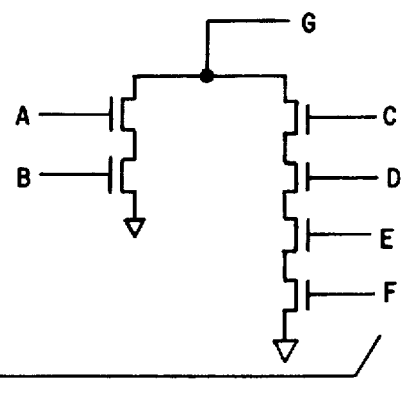
Fig. 11R

THE DATA CHIP

THE ROM CHIP

ELECTRONIC CALCULATOR IMPLEMENTED IN SEMICONDUCTOR LSI CHIPS WITH SCANNED KEYBOARD AND DISPLAY

This is a continuation of application Ser. No. 255,856, filed May 22, 1972.

BACKGROUND OF THE INVENTION

Electronic desk top calculators have been changed in design due to the availability of MOS/LSI chips which allow the entire system to be embodied in only one or a small number of semiconductor devices. The term MOS/LSI refers to Metal Oxide Semiconductor Large Scale Integrated Circuits; "MOS" is used interchangably with MIS or Metal Insulator Semiconductor, both terms referring generally to insulated gate field effect transistors. This technology permits large savings in manufacturing, labor and material costs and allows calculators to have operating functions not possible at reasonable cost in machines built from discrete devices or from large numbers of integrated circuits. A calculator system adapted to be implemented using only one MOS/LSI chip is set forth in co-pending application Ser. No. 163,565, assigned to the assignee of this invention, now abandoned. A feature of the calculator disclosed in application Ser. No. 163,565 is the use of a random access memory array which is sequentially addressed to operate as a plurality of shift registers; this unit provides the main data registers in a space on the chip much less than needed for shift registers of conventional design. Another feature of said application was the keyboard scanning technique.

It is a principal feature of this present invention to provide an improved electronic calculator system adapted to be implemented in MOS/LSI technology, in a minimum of semiconductor chips or wafers. Another feature is to provide an expandable system which may include optional program memory arrays and data registers. Other features include use of the sequentially addressed memory of Ser. No. 163,565 with a timing arrangement in such a manner that auxilliary timing generators are not needed, and the provision of a keyboard interface register which provides keyboard and timing information encoded for entering into the data registers or for selecting an address for the program memory. A further feature is an arithmetic logic unit which operates fast enough so that bits in the data registers may be shifted in parallel out of cells in the sequentially addressed memory array through the ALU and back into the same cells.

BRIEF DESCRIPTION OF THE DRAWINGS

The novel features believed characteristic of the invention are set forth in the appended claims. The invention itself, however, as well as further objects and advantages thereof, will be best understood by reference to the following detailed description of an illustrative embodiment, when read in conjunction with the accompanying drawings, wherein:

FIGS. 4A and 4B are representations and tables showing the make-up of the instruction word used in the system of the invention;

FIGS. 5A and 5B are timing diagrams showing the timing of various parts of the system of the invention;

FIG. 6 is a representation of the keyboard layout used for the calculator of the invention;

FIG. 8A represents the coding of the K information and D times in the keyboard register;

FIG. 8B is a table of the keyboard code; and

FIG. 8C is a specific encoding of one keyboard entry.

FIGS. 10A to 10E is a composite schematic diagram of the circuit of the "ROM chip" part of the system of the invention;

FIGS. 11A to 11R are detail views of certain circuits used in the system of FIGS. 9 and 10;

DETAILED DESCRIPTION OF SPECIFIC EMBODIMENT

Figure 1:
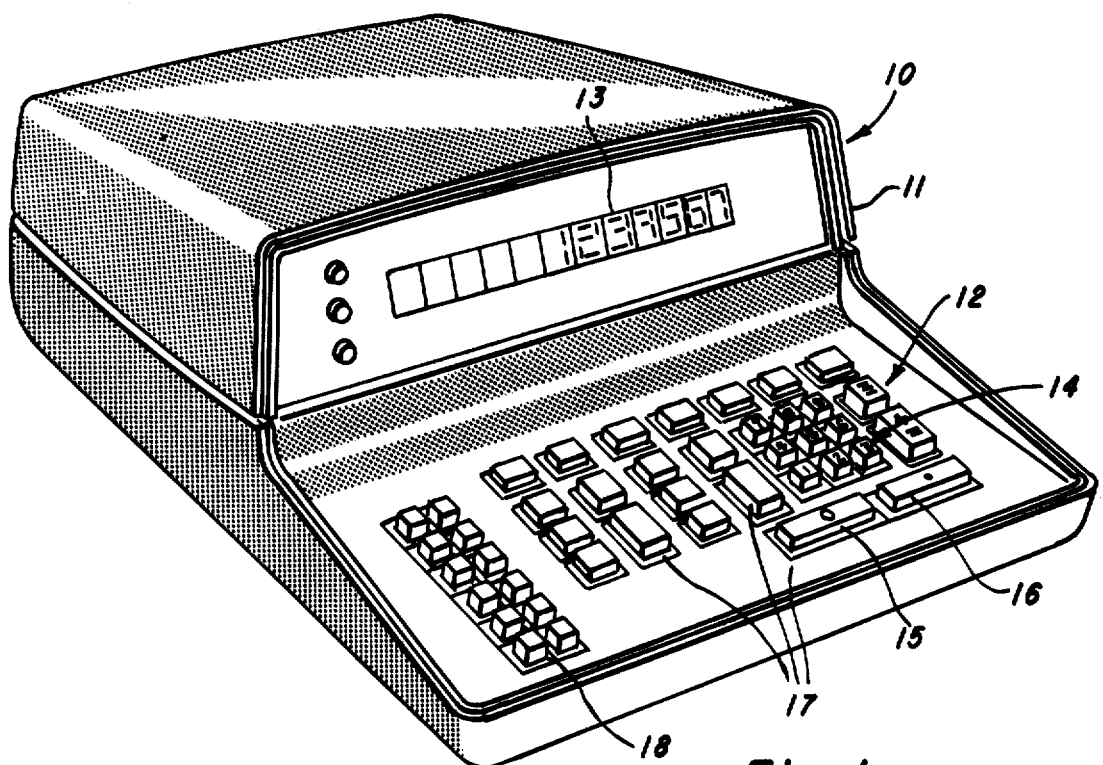
FIG. 1 is a pictorial view of an electronic desk top calculator which may employ the invention.
Figure 2:
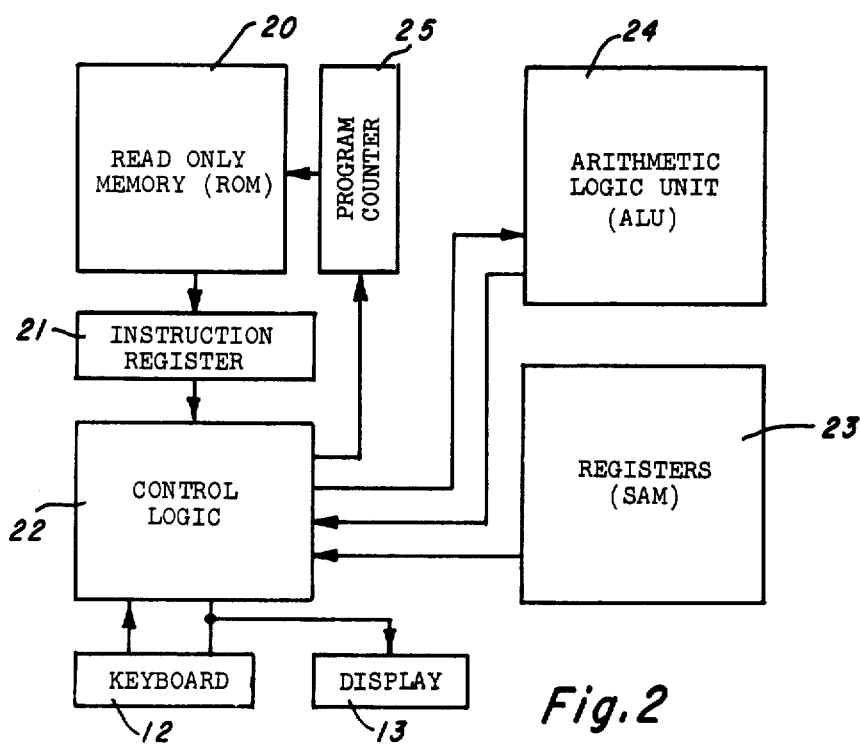
FIG. 2 is a simplified block diagram of the calculator system of the invention.

Referring to FIG. 1, an electronic desk-top calculator 10 of the type which may employ features of this invention is shown in pictorial form. The calculator 10 comprises a housing 11 having a keyboard 12 and a display 13. The display, in one embodiment, consists of thirteen or fourteen digits or characters, each provided by a Nixie tube, a liquid crystal display unit, an array of light emitting diodes or other display means. Ordinarily, the display would be of the so-called seven-segment or eight-segment variety, with provision for indicating a decimal point for each digit. The keyboard 12 includes the usual set 14 of number keys one through nine plus a zero key 15 and a decimal point key 16, along with twenty or so function keys 17, and twelve decimal point set keys or switches 18. A fixed decimal point position for the display 13 may be set by a thumb wheel, or a lever switch, in place of the switches 18. The function keys 17 include functions such as plus equal $\pm$, minus equal $\rightleftharpoons$, multiply $\times$, divide $\div$, clear all CA, along with a number of unique functions as will be described. Data or numbers are entered by the keys 14, 15, 16, and instructions are entered by the function keys which serve to call sub-routines from an internal stored program to execute the desired operations. Intermediate and final results of calculations are indicated on the display 13. Generally, the construction and operation of the calculator may be explained according to the block diagram of FIG. 2, but this diagram is not intended to be structurally definitive. The calculator includes a program memory 20 for storing the control program, this memory being a read only memory (ROM) comprised of several hundred or more, of multibit word storage locations. Instruction words are read out of the ROM 20 one word at a time into an instruction register 21, and are decoded and excuted by control logic 22. The control logic 22 is responsive to the fixed instruction words from the ROM 20, to the instructions entered from the keyboard 12, particularly the function keys 17, and also to the internal conditions of the calculator system. Data is stored in registers 23 which include basically a sequentially addressed random access memory organized as four data registers of sixteen digits each. The registers 23 also include two flag registers and a keyboard interface or special purpose register. All operations on the data entered into the registers 23 is carryed out in an arithmetic logic unit 24, which is of the bit parallel, serial digit type. Control logic 22 also operates a program counter 25, which is capable of addressing each of the addressable locations in the ROM 20, whereby the instruction stored in each location is read out into the instruction register. Usually the program counter is incremented by one for each instruction cycle, as controlled by timing means, so the instructions of a particular sub-routine stored in the ROM are read out in sequence. However, branch instructions appearing at the instruction register 21 are recognized by the control logic 22 and modify the sequencing of the program counter 25. Also seen in the block diagram of FIG. 2 is the visual display 13, which displays the contents of a register. Both the keyboard 12 and the display are scanned rather than continuously connected into the control logic, according to a feature of the invention.

Figure 3:
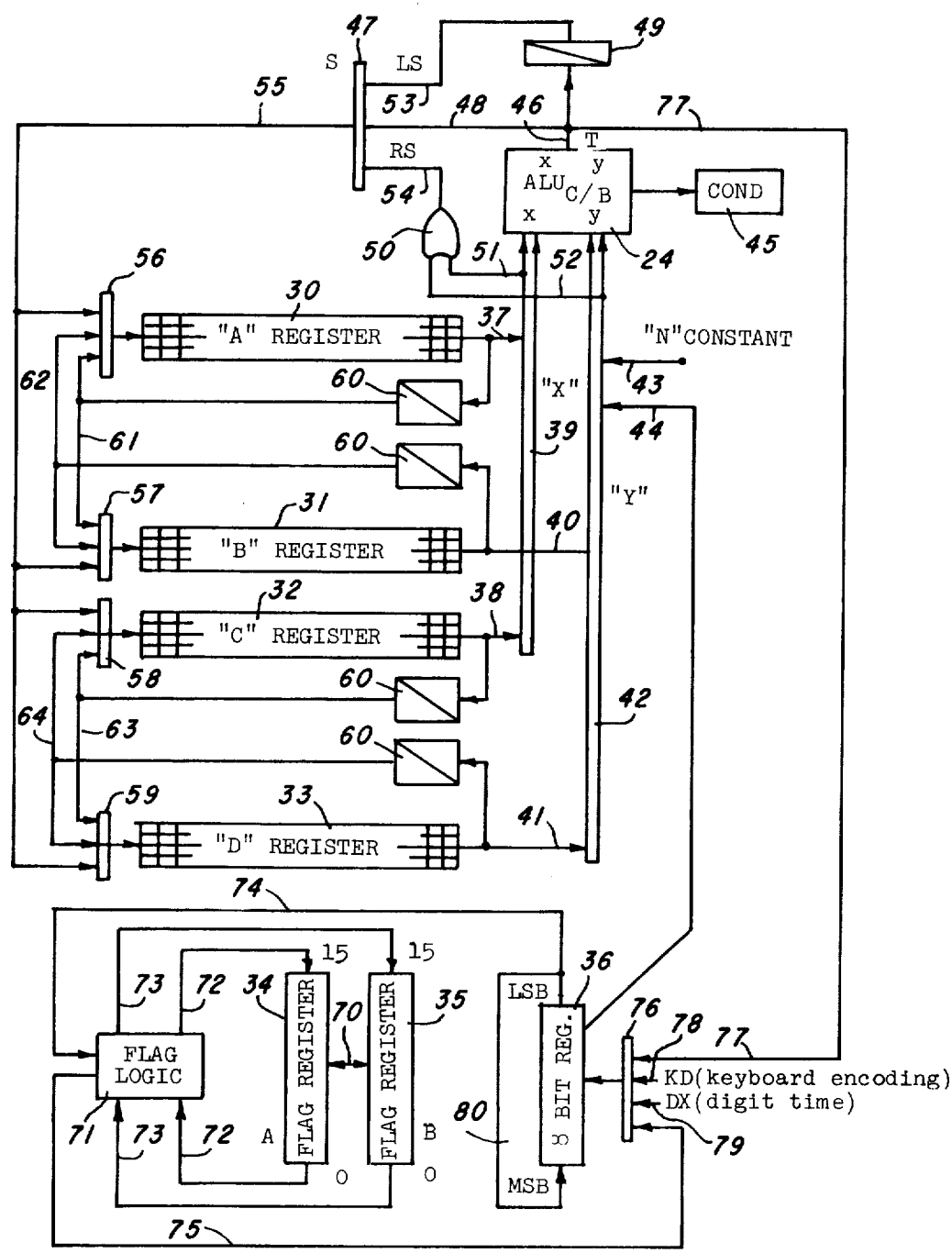
FIG. 3 is a more detailed block diagram of the registers and part of the logic of the electronic calculator of the invention.

Referring to FIG. 3, the data storage registers 23 are shown in more detail along with part of the arithmetic logic unit 24 are interconnecting data paths. No attempt is made to show the control logic, timing, or other features in FIG. 3. The calculator has four registers, 30, 31, 32, 33, for basic data storage, named the A, B, C and D registers. Each of these registers contains sixteen digits or characters, four bits per character, in binary coded decimal or hexidecimal format. Instead of the usual shift registers employed in most electronic desktop calculators for data storage, these registers 30-33 are implemented by a sequentially addressed read-write memory of the type set forth in co-pending U.S. patent application 163,683, now abandoned, assigned to the assignee of this invention, as described below. Two groups of sixteen flags are also available with flag registers 34 and 35, also referred to as FLGA and FIGB. An eight bit special purpose register 36, or REG8, is available for keyboard interface or flag transfer in groups.

The ALU24 of FIG. 3 is a four bit parallel binary or BCD adder. Outputs 37 and 38 from A and C registers 30 and 32 are connected to "X" bus 39, and outputs 40 and 41 from B and D registers to "Y" bus 42. Although shown as one line, the outputs 37, 38, 40 and 41, as well as the X and Y buses, are acually four parallel lines representing one, two, four and eight in BCD fashion; this is true of most of the data connections of FIG. 3. A predefined constant "N" can be logical "OR'ed" with the Y bus 42 at an input 43, or four least significant bits from REG8 register 36 may be likewise OR'ed with the Y bus at input 44. The inputs to the ALU24 at the X and Y buses thus may include the outputs of any of the main A, B, C or D registers, and REG8 contents, and a constant N. The ALU24 generates a carry/borrow signal which can be used to set a COND flip flip 45 to zero, and also for the arithmetic operation.

The output 46 of the ALU 24 is a T register which may be connected directly back through an S bus 47 by a line 48 with no shift or connected through a one bit delay 49 to the S bus 47 to produce left shift. Right shift is provided by taking the logical OR in a gate 50 from inputs 51 and 52 from the X and Y buses. The left and right shifted inputs 53 and 54 are applied to the S bus 47, the output 55 of which is connected as inputs of selector gates 56, 57, 58 and 59 for the A, B, C and D registers. Other inputs to the selector gates 56-59 include a recirculate path for each register; the recirculate paths include a one bit time or one state time delay 60 for each register. As will be described, the A, B, C and D registers do not "shift" in the usual sense of shift registers while recirculating, but instead a bit is taken out of one location in the SAM and returned to the same location. Also, the output is not just at one end as would appear in the block diagram of FIG. 3, but instead is from both ends. Recirculate and exchange are done at one end and ALU operations and shifting is done from the output at the other end. The selector gates 56-59 are thus actually several gates. The contents of the A and B registers may be exchanged, and likewise the contents of the C and D registers may be exchanged; for this purpose, the delayed output of the A register 30 is connected by a line 61 to the selector gate 57, and the output of the B register 31 is connected by a line 62 to the input of the A register 30. Similar cross connections 63 and 64 are provided for the C and D registers.

The A and B flag registers are each sixteen bit binary registers located in the SAM; the flags are one bit binary values which are used by the ROM program to store status information which can be examined or changed at a later time, typical flags being minus sign, error, overflow, etc. Addresses of zero through fifteen are used to access the flags. The A and B flags which have the same address are said to be adjacent, and can be exchanged, as indicated by a connection 70 in FIG. 3. Flag logic 71 permits flags to be recirculated by paths 72 and 73, and also permits entering information from the 8 bit register 36 into the flag registers 34, 35 by a line 74. Further, information in the flag registers may be entered into the 8 bit register 36 by a connection 75 from flag logic 71 to a selector gate 76 for the register 36. Other inputs to the selector gate 76 include a connection 77 from the T register output 46 of the ALU 24, an encoded keyboard K-D entry 78, and a digit time entry 79. The 8 bit register may also be recirculated by a path 80.

The Instruction Word

Each instruction word stored in the ROM 20 and read into the instruction register 21 consists of thirteen bits, $I_0$ thru $I_{12}$. If the word is for an operation, the left most bit $I_{12}$ will always be a 1; if the word is for a branch, $I_{12}$ will always be a 0. The formats for operation or branch are different, and are seen in FIG. 4A. The format for instructions includes: a three bit S or $\Sigma$ field, $I_0$ thru $I_2$; a four bit R field, $I_3$ to $I_6$; a subtract field, $I_7$; a four bit M field or mask field, $I_8$ to $I_{11}$; and the instruction/branch indication $I_{12}$. The format for branches includes: an eleven bit address field $I_0$ to $I_{10}$ (two bits being chip select and nine being a ROM address); a one bit condition field $I_{11}$; and a one bit instruction/branch indication $I_{12}$. The table of FIG. 4B gives the binary words used for S, R and M fields, for each possible value of S, R and M; thus, M5 would be 0101, M15 would be 1111, etc.

If $I_{12}$ is zero, the instruction word is for a branch, and the branch is conditional depending upon the value of bit $I_{11}$. If $I_{11}$ is zero, a branch will be executed if a condition code, COND, is zero; if $I_{11}$ is one in the instruction word, a branch is executed if COND is one. The address field $I_0$ to $I_{10}$, contains the ROM location or address, which is stored in the program counter 25 if the branch is taken. A branch will set the condition code COND to "1" if the next instruction to be executed is not a branch.

If $I_{12}$ is one, the instruction word is for an operation. Arithmetic and shift instructions are defined for an M field of Mo to M12, or binary 0000 to 1100 appearing on $M_a$ to $M_d$ as seen in FIG. 4B. This M0 to M12 field defines thirteen digit masks as shown in Table I at the end of the specification, where the masks are described by state times S0 to S15 which will be explained later. A constant N, also seen at 43 in FIG. 3, is generated at a certain state time along with the digit mask. The inputs and operation of the ALU 24 are specified by the R field and SUB. The input paths to the A, B, C and D registers, selection gates 56-59, are specified by the $\Sigma$ field. Again for the digit masks M0 to M12, Table I, the X and Y inputs to the ALU 24 and the operation performed are set forth in Table II for the various possible R fields. The capital letters, A, B, C, D in the Table indicate the main registers. Table III shows the operations performed for various $\Sigma$ fields. As may be seen, the hardware or control logic 22 responds to predetermined combinations of 0's and 1's in the instruction word to interconnect the system as desired and to perform the needed operations.

Timing

Figure 5A:
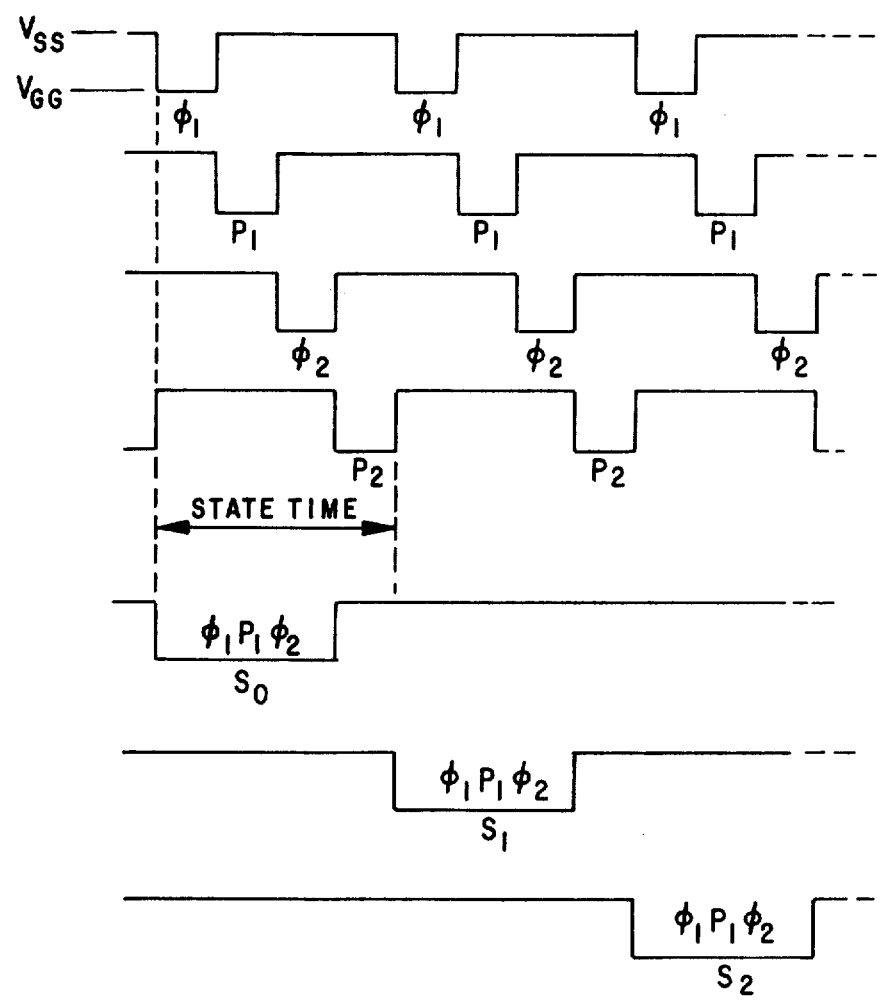

The entire system operates on two externally provided clocks $\phi_1$ and $\phi_2$ as seen in FIG. 5A, and two internally generated clocks P1 and P2. The frequency used in 250 KHz for $\phi_1$, $\phi_2$. The clock generators may be conventional and are not shown herein.

One set of clocks $\phi_1$, $P_1$, $\phi_2$, $P_2$ is referred to as a state time, and represents the time for one bit from each of the main registers A, B, C, D to be operated on in parallel by the ALU, etc. The BCD arithmetic used in the invention requires one full set of clock pulses for each digit, so sixteen sets or state times are needed to perform arithmetic operations on all sixteen digits in a register. Sixteen state times represent one D-time or instruction cycle, as seen in FIG. 5B.

Individual address lines in the registers 23 are energized only for three of the clocks $\phi_1$, $P_1$, $\phi_2$, rather than all four; these groups of three are also referred to as state times S0 to S15 as seen in FIG. 5A. A feature of the invention is the use of the same state times as generated to operate the address lines of the SAM register 23 to operate or time the remainder of the system.

D times generated directly from state times S0-S15 are used to scan the keyboard and the display. As seen in FIG. 5B, the D times count down, D15, D14, D13 ... D1, while the state times count up, S0, S1, S2 ... S15; this feature aids in the zero suppression technique since leading zeros to be suppressed are on the left or MSD first while the ALU must operate from right to left or LSD first. There are fifteen D times and sixteen state times.

The Keyboard

One embodiment of the invention uses a keyboard as seen in FIG. 6. This keyboard includes natural number keys 14 for one thru nine, a zero key 15 and a decimal point key 16. Twenty function keys 17 are included, as will be described; these are all push-bottons which stay closed only so long as depressed by the operator. In addition, a number of switches are included, such as mode switches 19 and rounding switches 90. The decimal point position is set by switches 18 which may be individual buttons as seen, or a thumbwheel; a floating point switch is also included.

A natural number key 14-15 enters the number punched into a register and displays it. The decimal point key 16 enters a decimal point. Only the first decimal point is protected.

The function keys 17 cause an internal change in the calculator such as performing an arithmetic operation, remembering an arithmetic operation, clearing registers, or changing the contents of registers. The specific operations caused by the function keys is set out in Table IV at the end of the specification.

The switches 18-19 are functional controls, like the function keys 17, but once they are closed they remain closed until manually opened. The decimal switches 18 enter a desired number of decimal places for the display at the end of a addition or subtraction calculation; multiplication and division is done in floating mode. A separate floating switch will override any decimal switch that is down. If no decimal switch 18 is set, the machine will always default to the floating mode.

The mode switches 19 include a $\Sigma$ or summation switch which causes memory accumulation to occur when $\pm$ or $=$ key is pushed. A constant switch K designates a constant multiplicand, i.e., the number entered or the result acquired (product or quotient) before the last multiply command is stored. In the case of division, the number entered immediately after the last divide command, is the constant divisor.

The rounding switches 90 permit selection of the rounding operation in three modes. Round up, RU or an arrow pointing up, means if the quantity to be discarded is non-zero, a one is added to the LSD retained. Round off, or 5/4, means if the quantity to be discarded is half or more than half, a one is added to the LSD retained, otherwise the LSD retained is unmodified. Round down, RD or or an arrow pointing down, means that the number is merely truncated below the LSD to be retained, and any quantity is discarded.

An overflow lamp near the display is turned on when the interger part of the result contains more than twelve digits. If the number of decimal places cannot be displayed in full, but the integer part of the result is less than twelve digits, this is not truly overflow, but is referred to as pseudo-overflow. For example, if the decimal point is selected at 5, and the calculated result is thirteen digits, or 123456789.1234, then the display drops the last "4" and shows 123456789.123 which should be 123456789.12340 according to the DPT setting; this is pseudo-overflow.

An intermediate result, as the term is used later, means the result of an intermediate calculation performed, not from a $+=$ or $-=$ key, i.e., not from any "equality" function key. For example, if the following is punched—$a \times b \times c \div d \div e +=$; then an intermediate result of ab will be obtained after the second "X", an intermediate result of abc after the first $\div$, and an intermediate result of abc/d after the second $\div$. A final result is obtained after $+=$, or abc/de in the example.

The decimal point mode (fixed point) and floating mode determine the size of the display (i.e., the number of decimal places displayed). They do not affect the integer part of the number. Insignificant zeros (trailing zeros) may be added or deleted to satisfy the number of decimal places displayed. For example, if the result is 12.411733410 and the round down switch is depressed, DPT 5 on switches 18 will cause 12.41173 to be shown, DPT 7 will show 12.4117334, DPT 10 will show 12.4117334100 or padded with one insignificant zero, DPT 11 will show the same as for DPT 10 and will be in pseudo-overflow since the decimal point will be at ten instead of eleven, and F or floating will show 12.41173341 losing one trailing zero.

Rounding the number determines only the value of the LSD displayed depending upon the value of the MSD deleted. DPT mode and rounding are independent of one another but bear a certain relationship. "Rounding" means doing what the rounding switch says; "no rounding" means truncation of the insignificant decimal places. In F or floating mode, no rounding occurs for intermediate or final results; in fixed point mode, no rounding occurs for intermediate results, but the final result is rounded according to the switch 90. An intermediate result is always in floating mode, and floating mode is always no rounding.

Table V gives operation examples for the calculator to be described, with the ROM program to be set forth. Other operating sequences are possible with different programs in the ROM. In the examples, E means lighting an entry overflow indicator lamp near the display on the calculator face. A letter or number within a rectangle means this is a final result.

Figure 7:
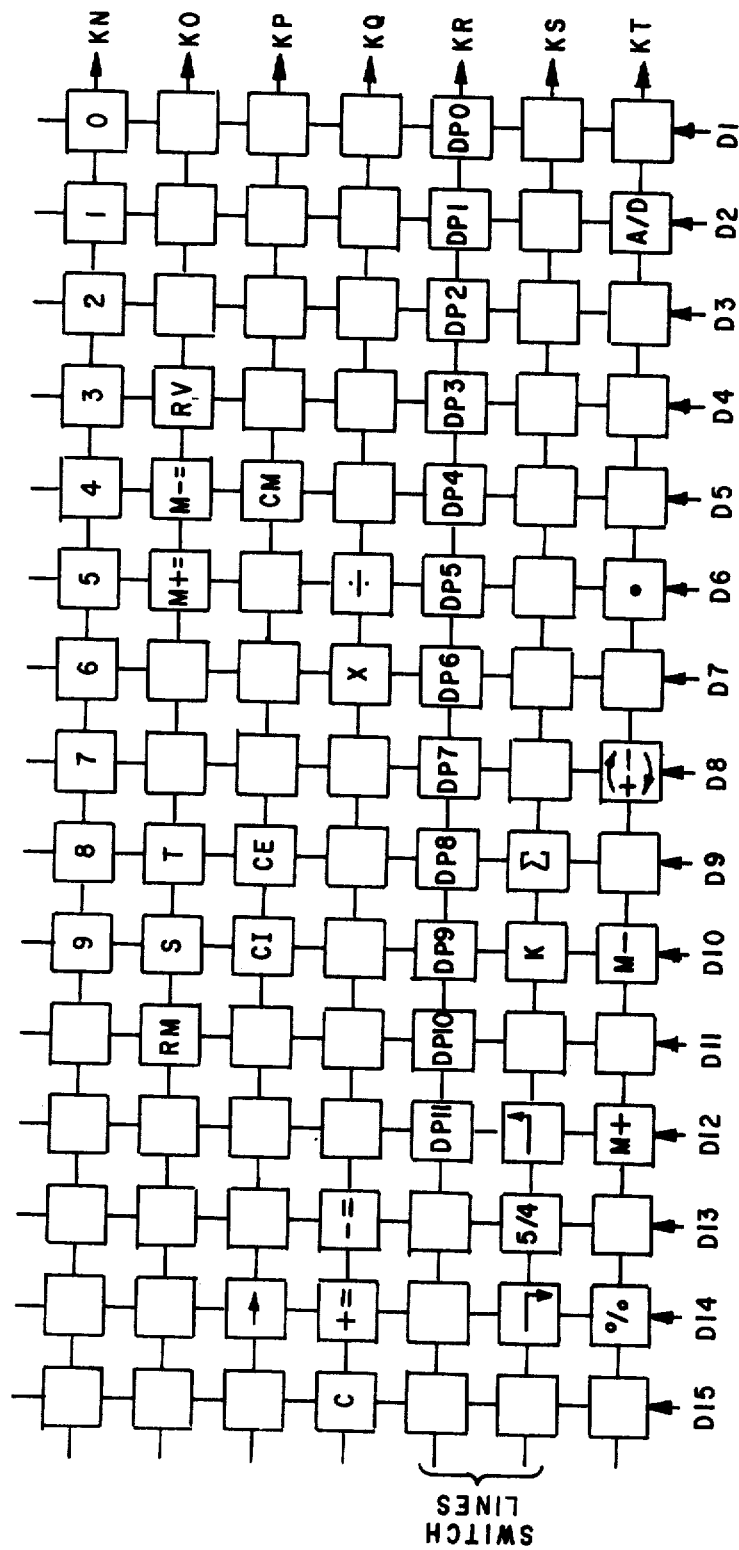
FIG. 7 is a representation of the keyboard input matrix.

In FIG. 7 there is seen a fifteen by seven matrix showing the keys from the keyboard arranged as scanned by the fifteen digit timing D1 to D15 signals, and as sensed on the seven outputs at KN to KT, from which keyboard information is entered into the system. If a "1" voltage appears on KQ at D7 time, then the X key is depressed, etc. The combination of a digit time and a sense line identifies a key, and these fifteen and seven line items are binary encoded within the machine to appear as four and three bits respectively; FIG. 8A shows the format for loading keyboard and digit time information into the register 36, with the code of FIG. 8B being used for K information. If a key at D10, KP is down after a keyboard scan, the register 36 will contain the word of FIG. 8C.

Detailed Description of Circuits

The system will now be described in detail with reference to FIGS. 9 and 10. The system was designed to be implemented with two MOS/LSI chips, one being the data chip of FIG. 9 and the other being the ROM chip of FIG. 10. All of the system is in the data chip except the ROM 20 and the program counter 25 which are in the ROM chip. The instruction register 21 is duplicated, in both chips.

The Instruction Register

Figure 9:
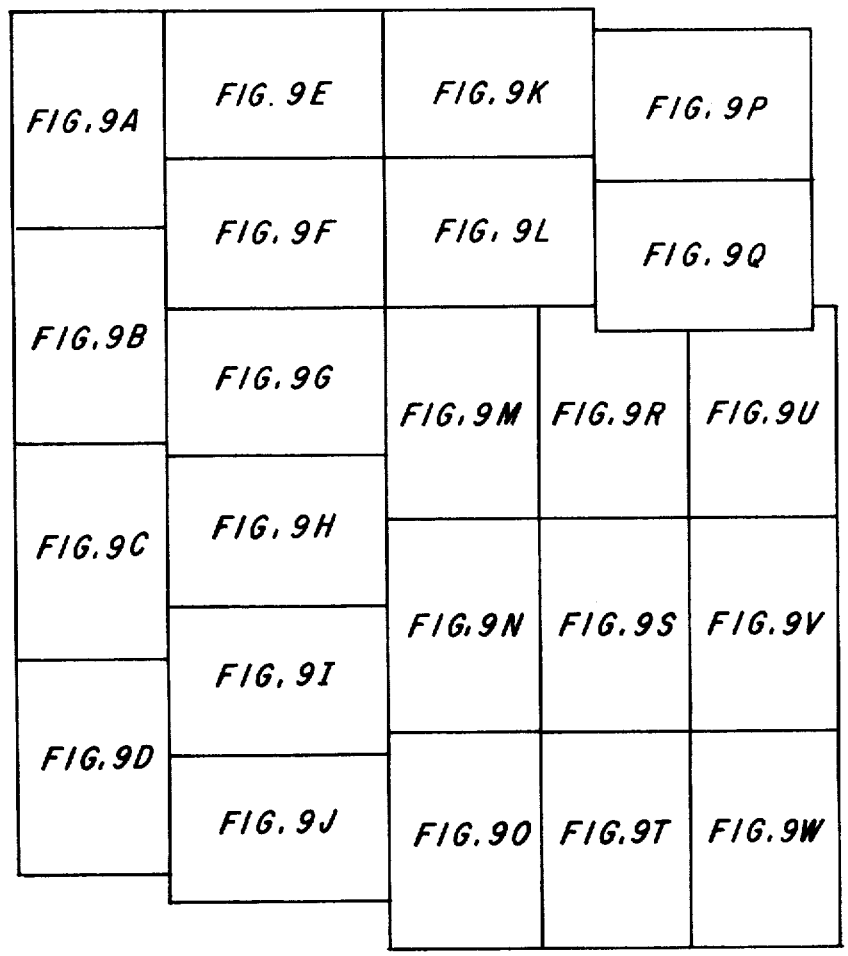
FIG. 9 is a diagram of the layout of FIGS. 9A–9W.
Figure 9A:
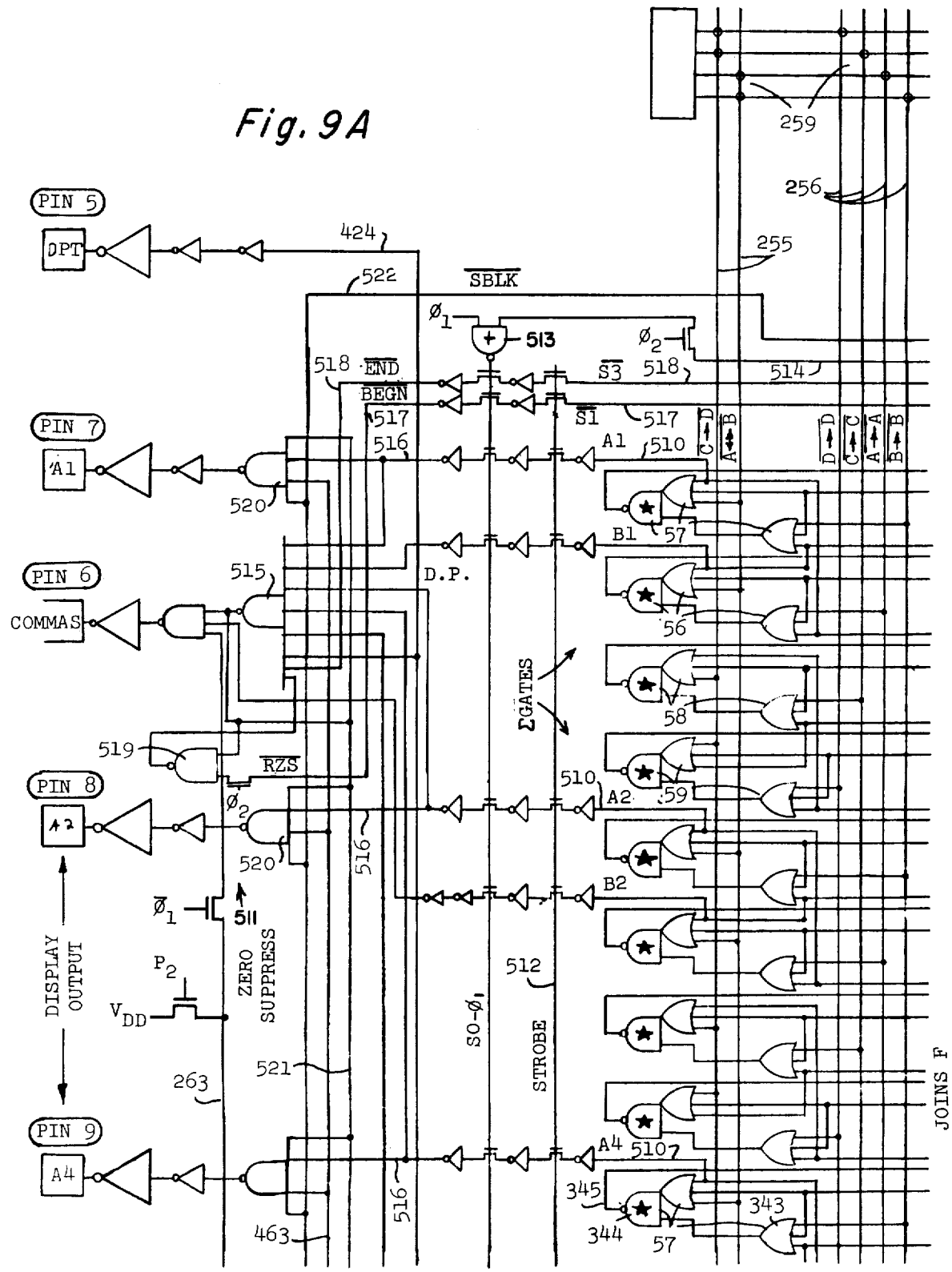
FIGS. 9A to 9W is a composite schematic diagram of the circuit of the "data chip" part of the system of the invention.
Figure 9B:
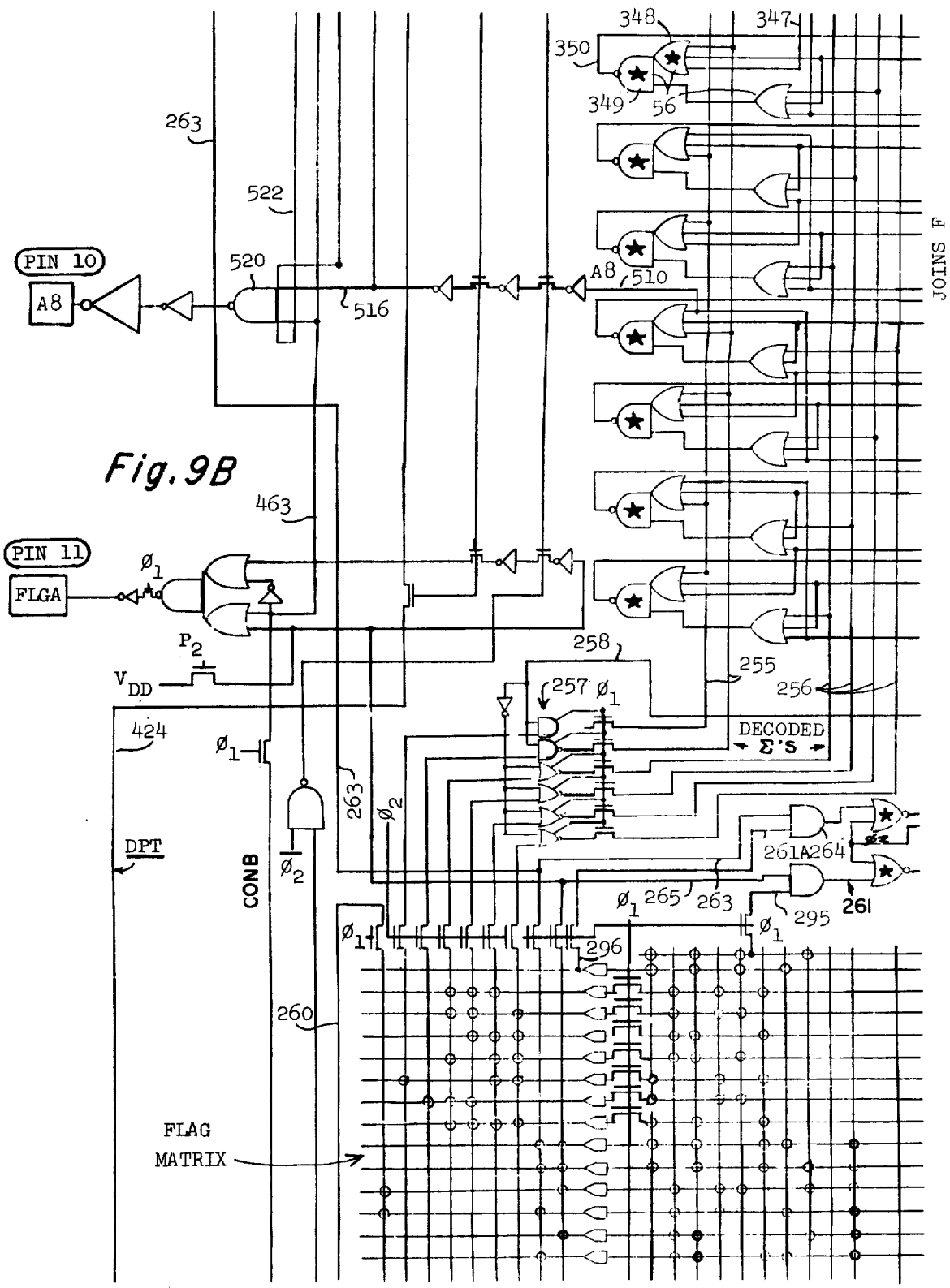
Figure 9C:
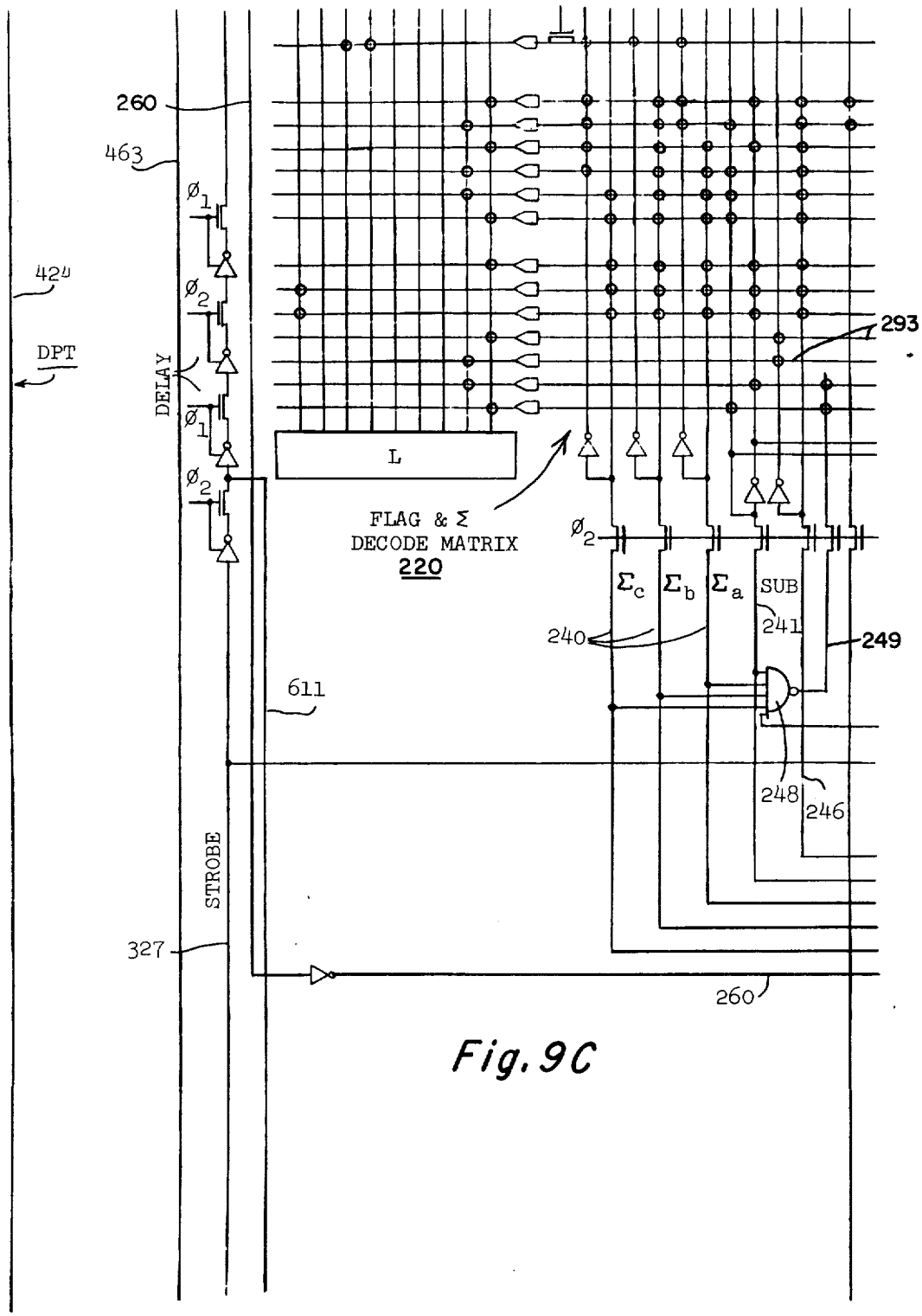
Figure 9D:
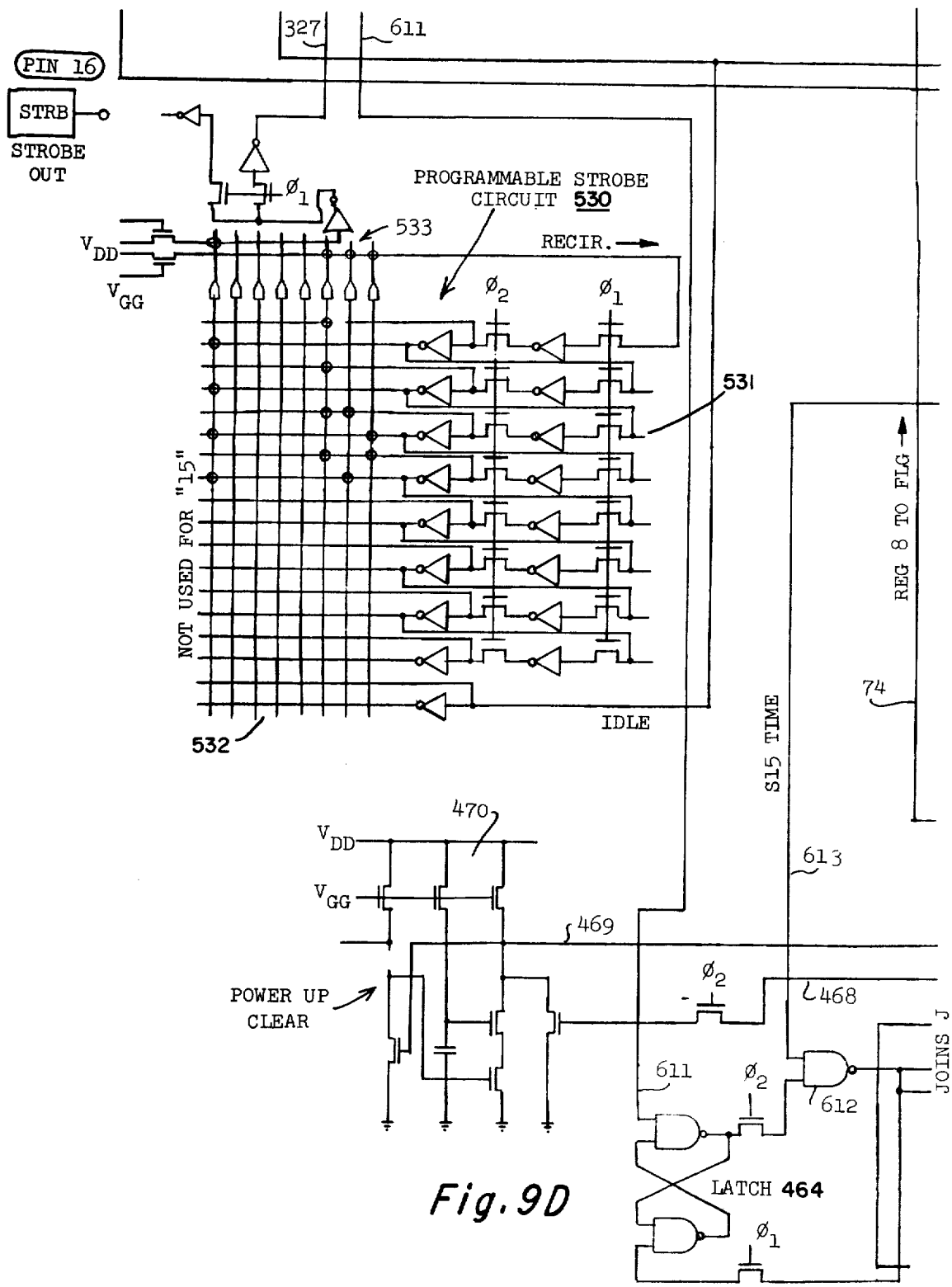
Figure 9E:
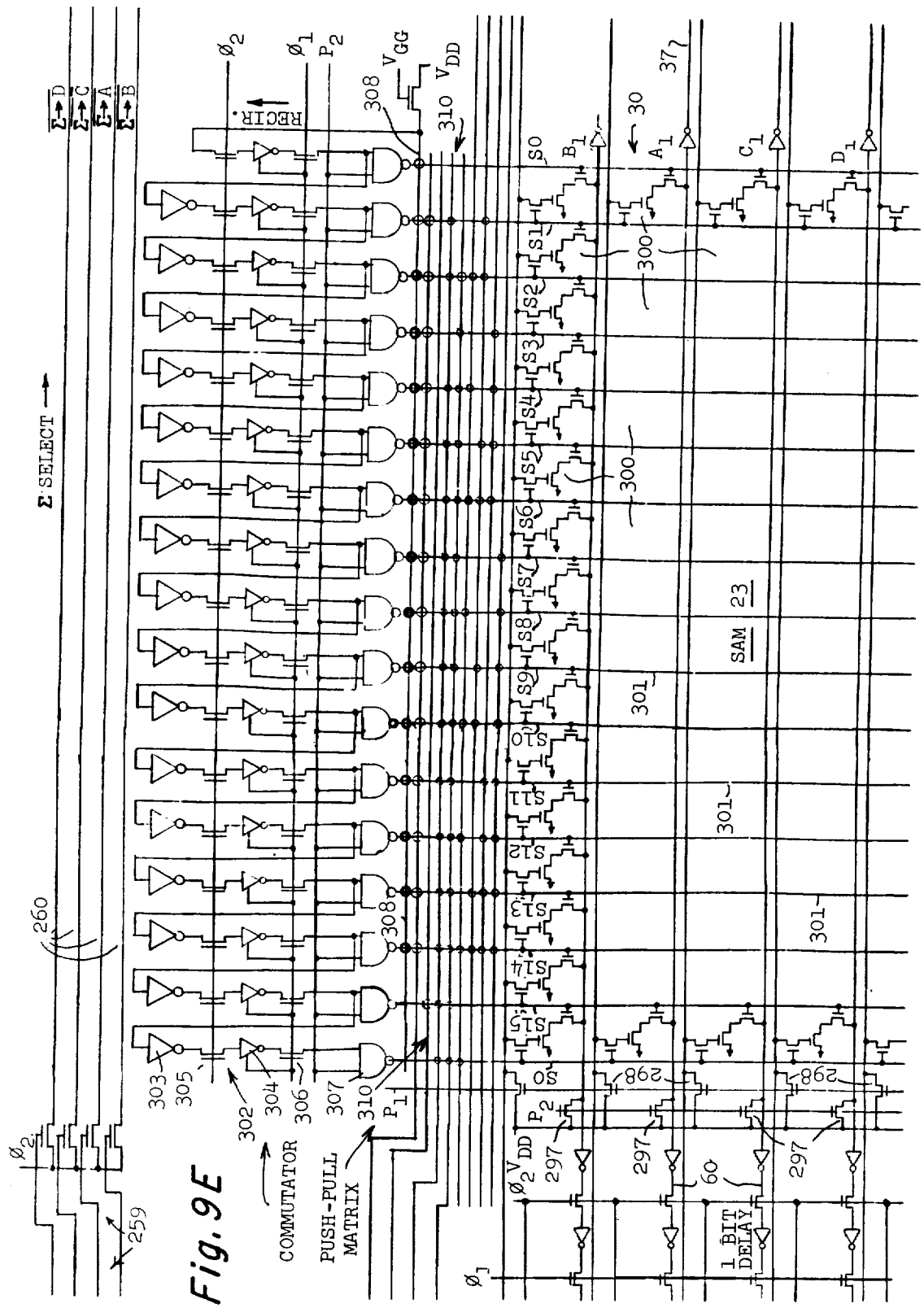
Figure 96:
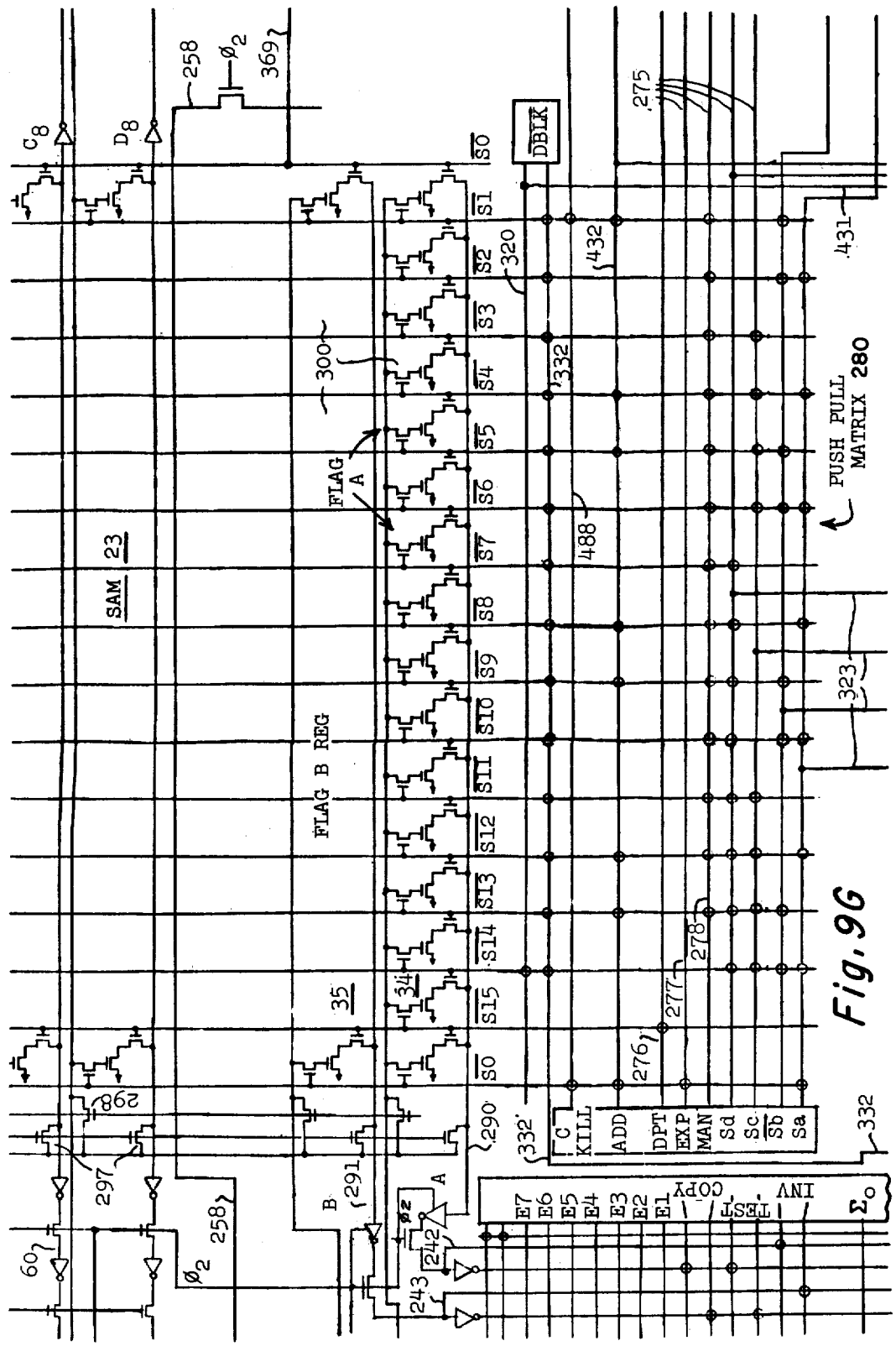
Figure 9H:
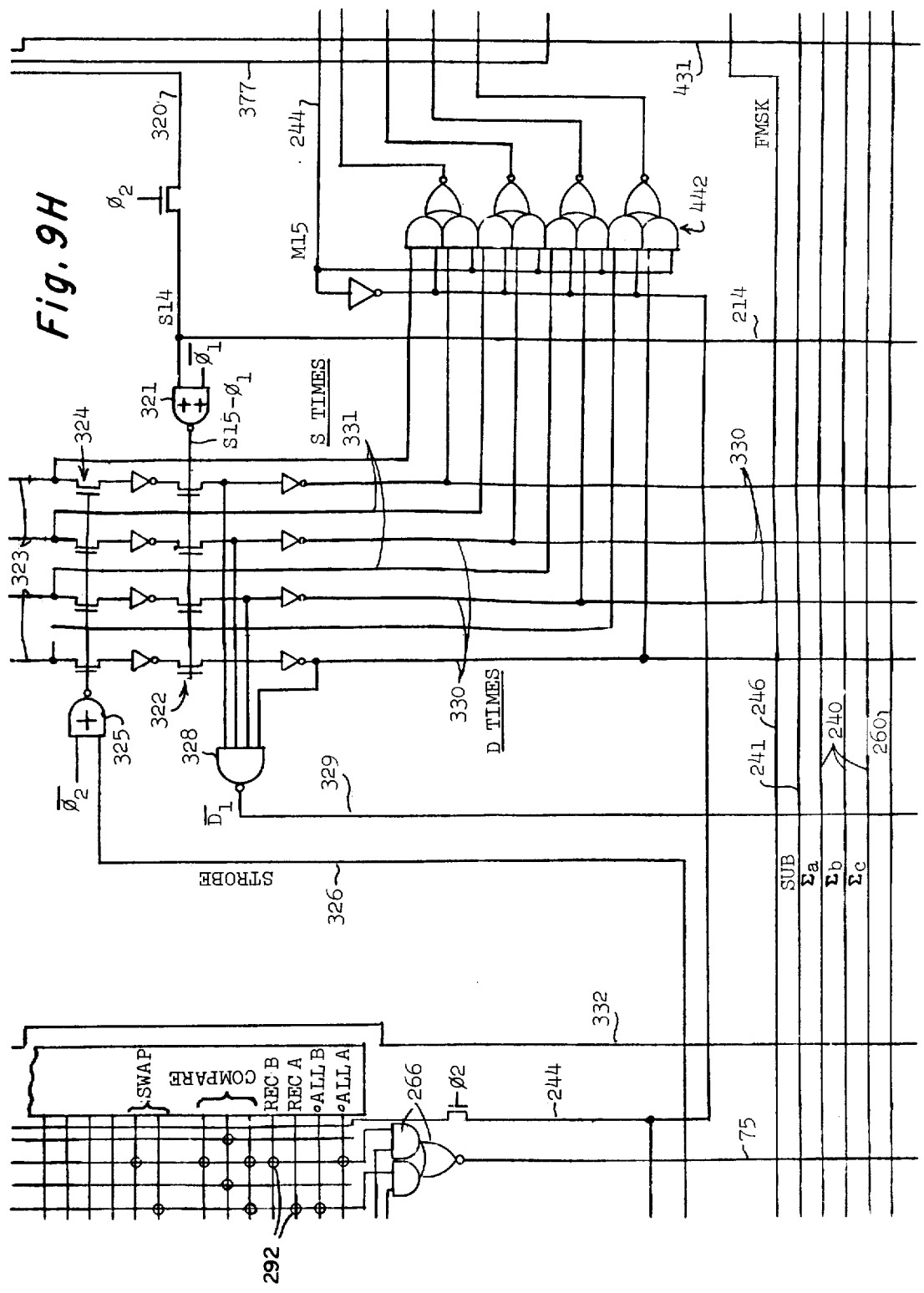
Figure 9I:
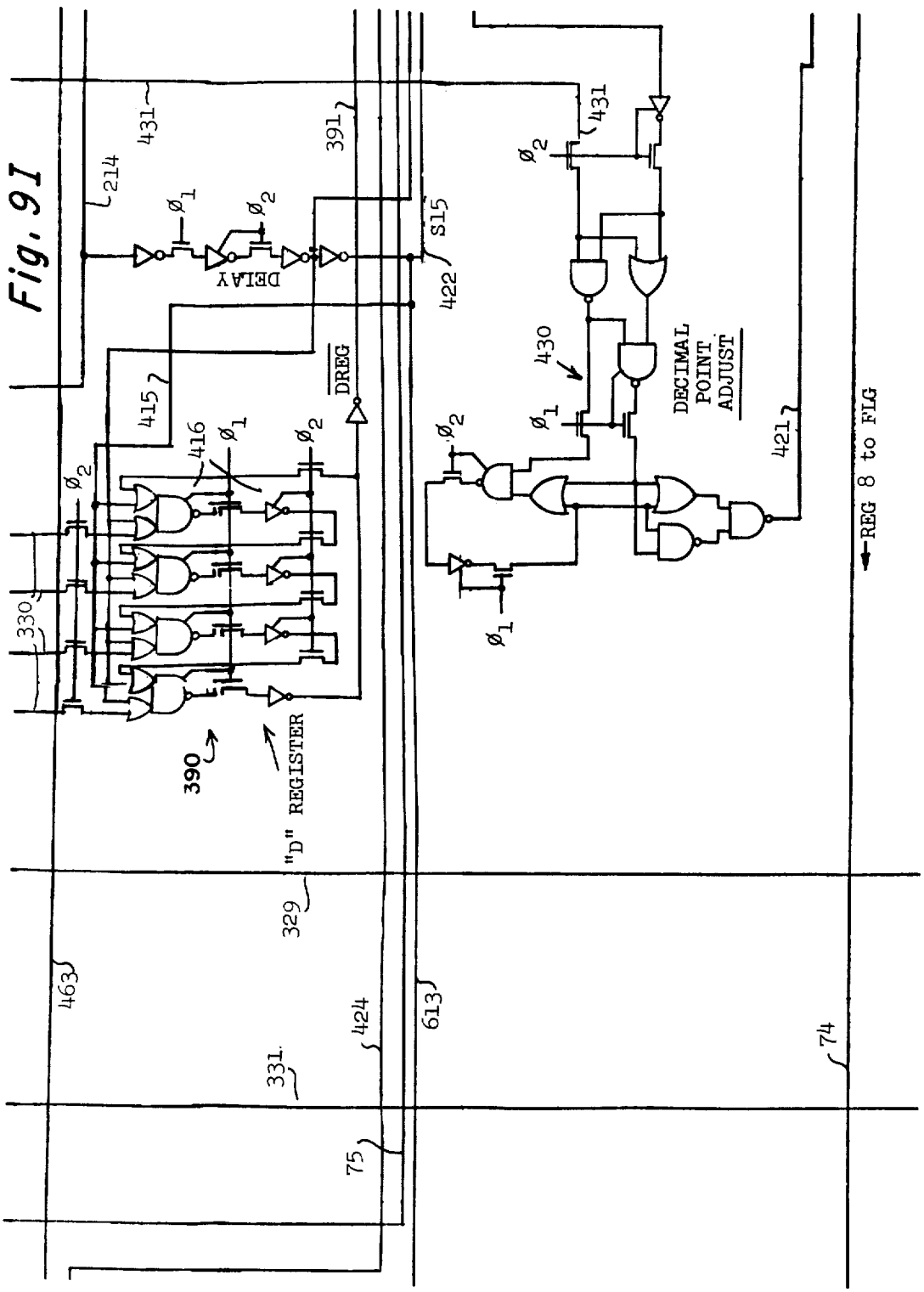
Figure 9K:
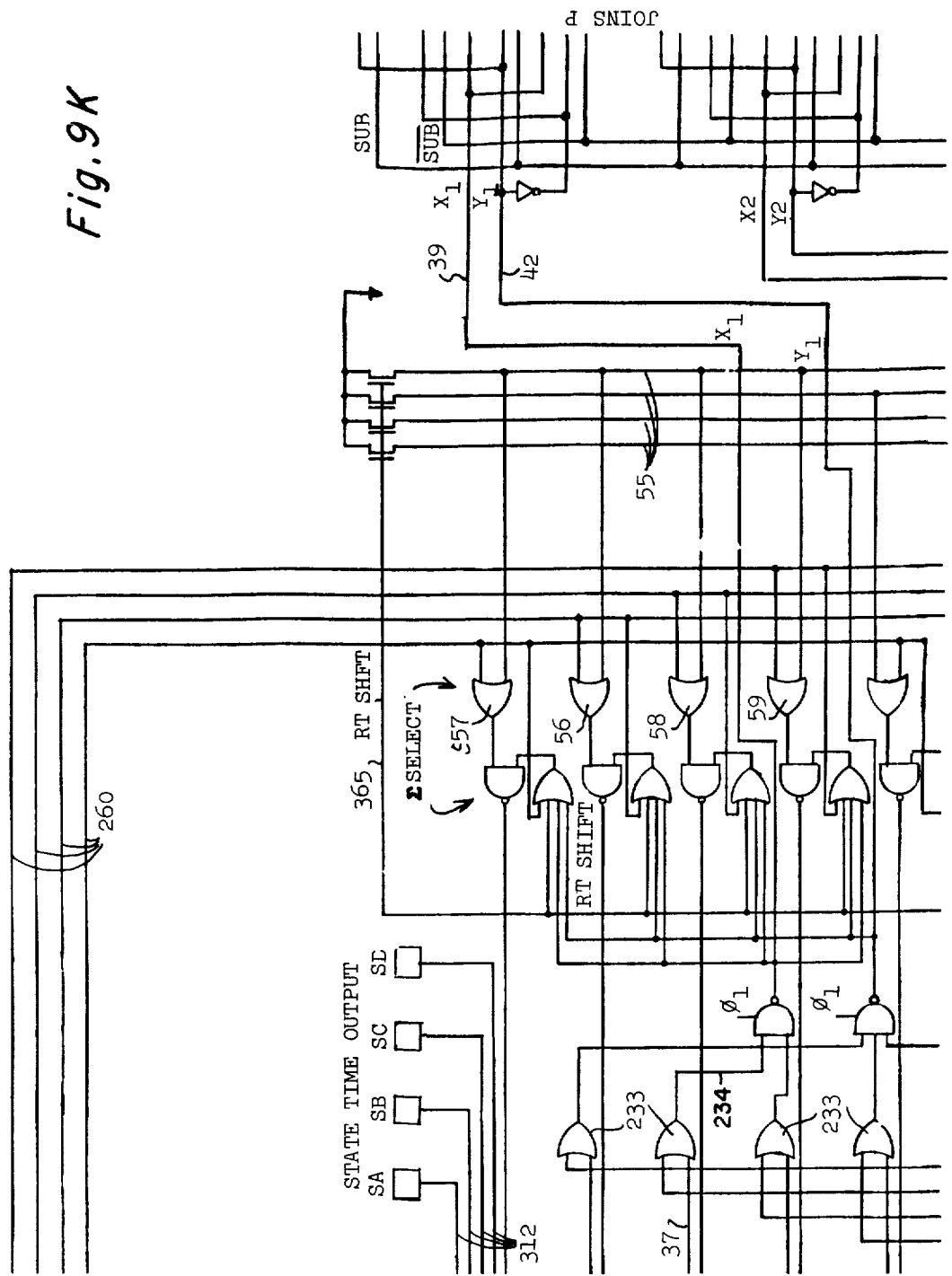
Figure 76:
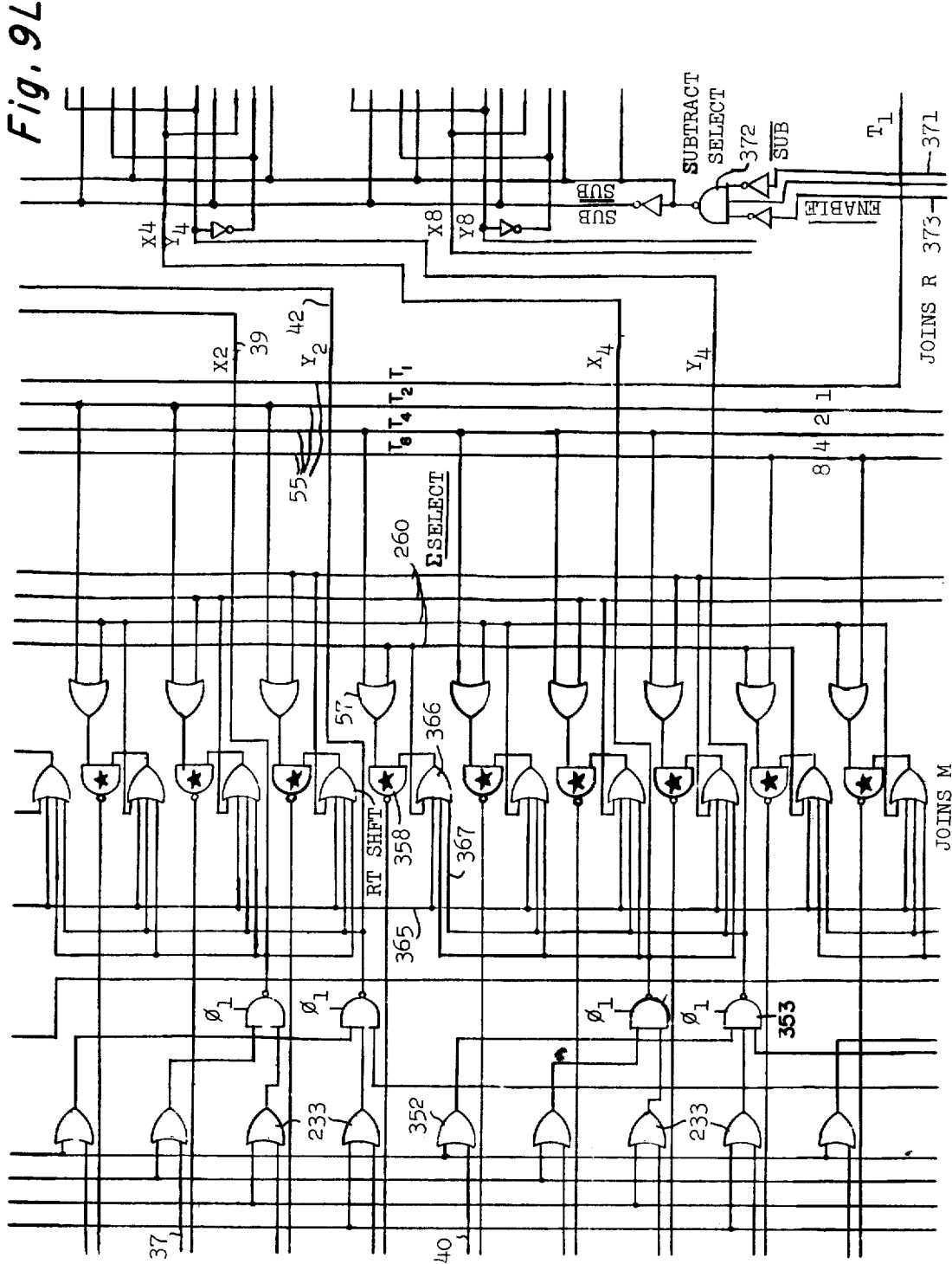
Figure 9M:
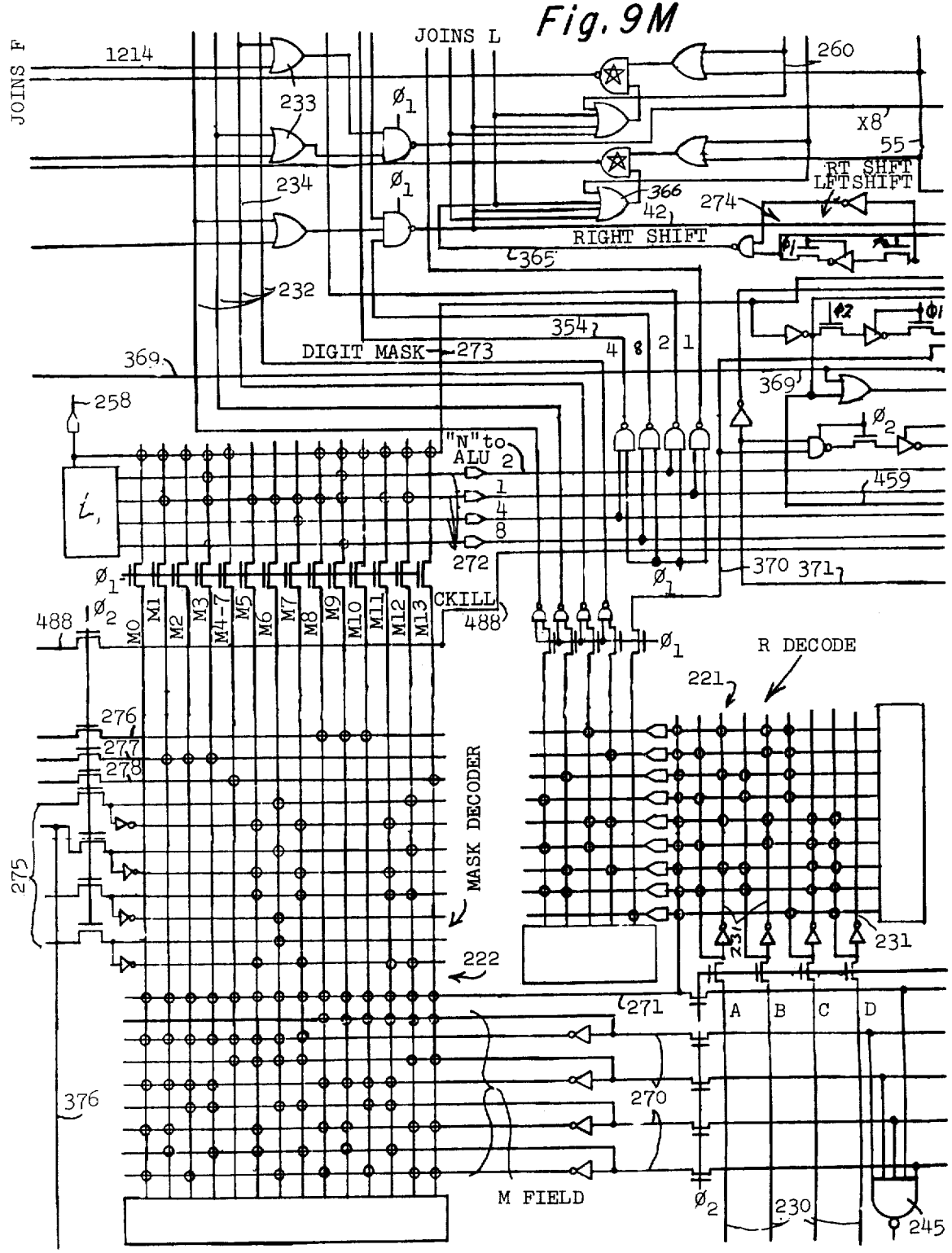
Figure 9N:
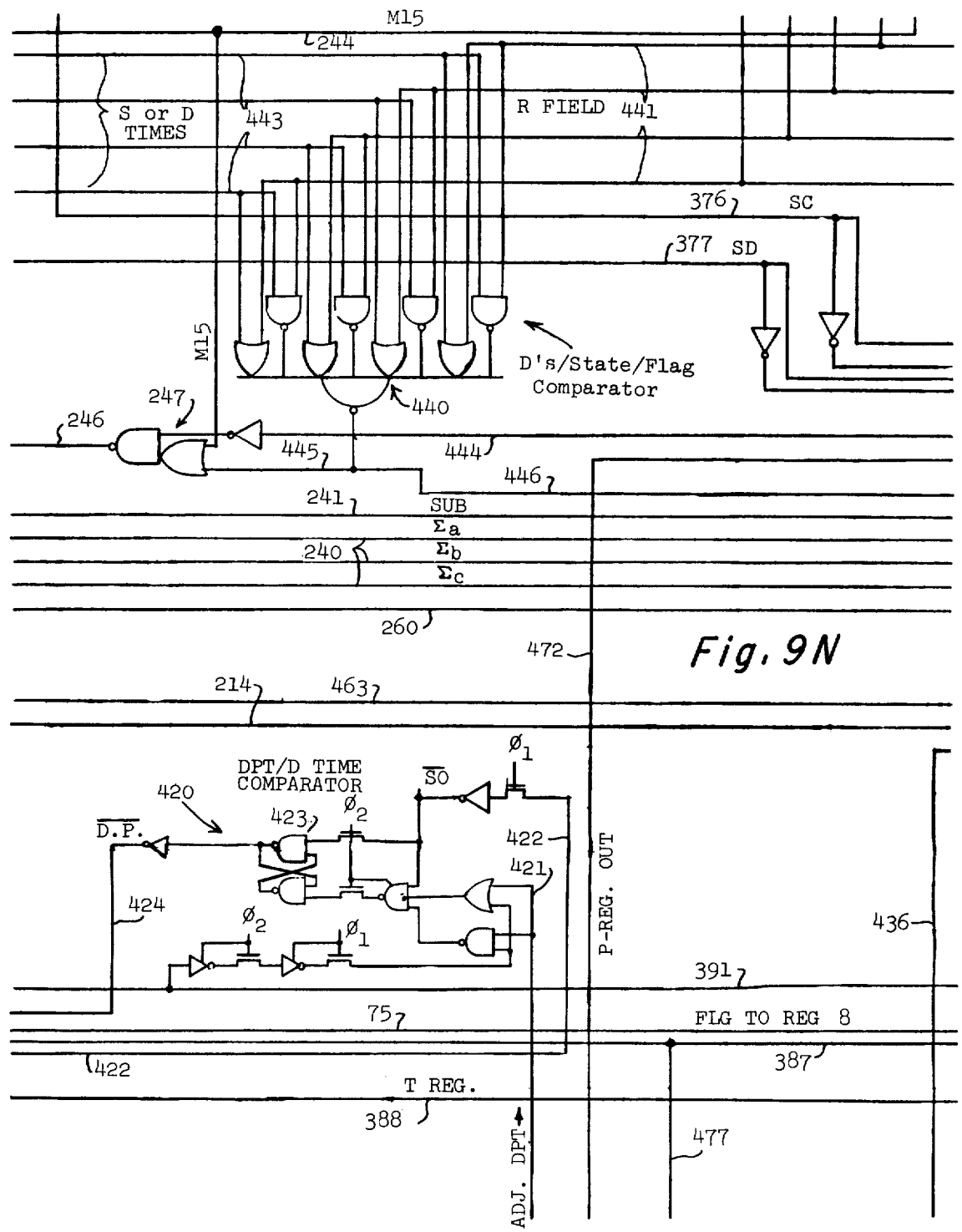
Figure 9P:
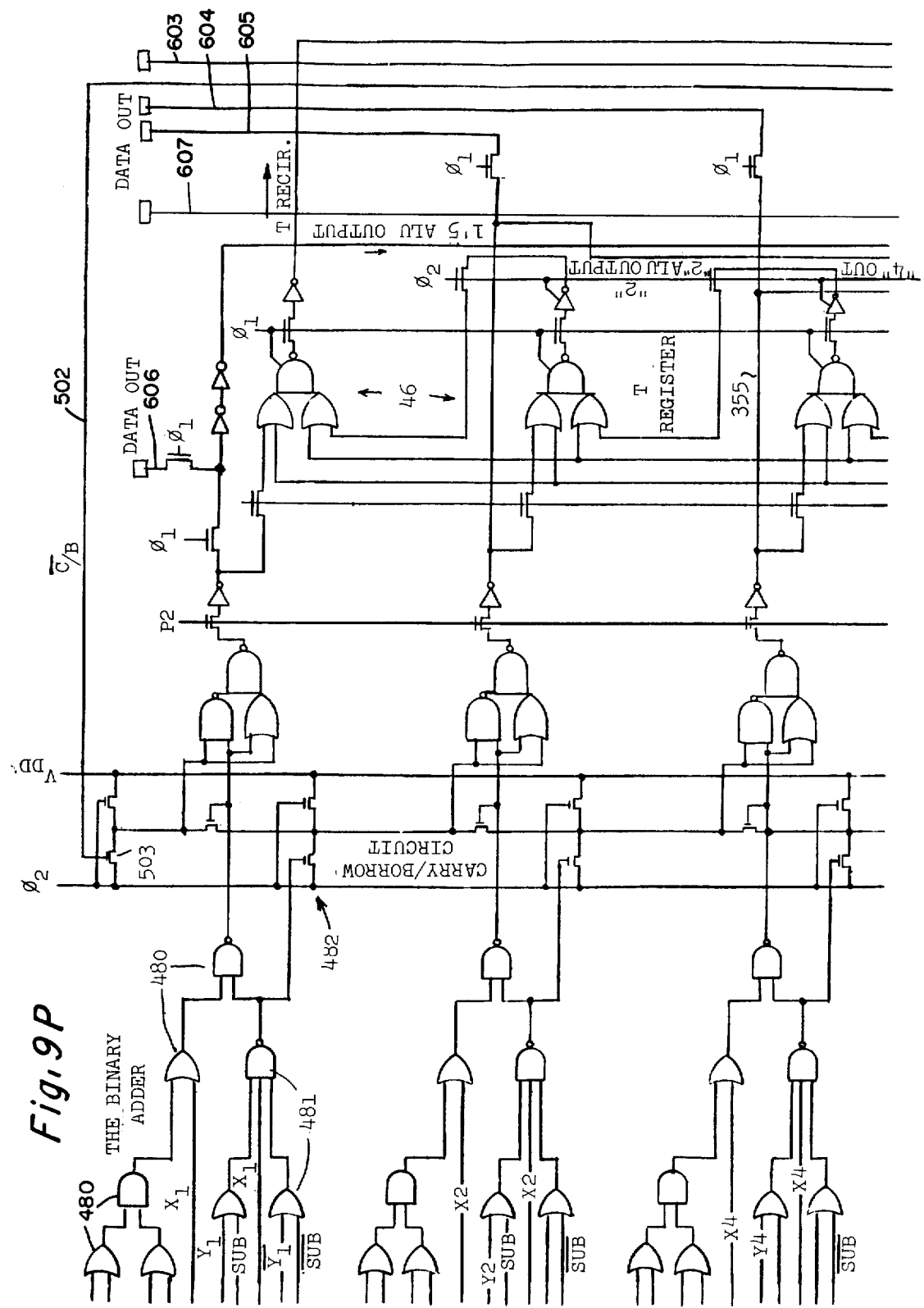
Figure 90:
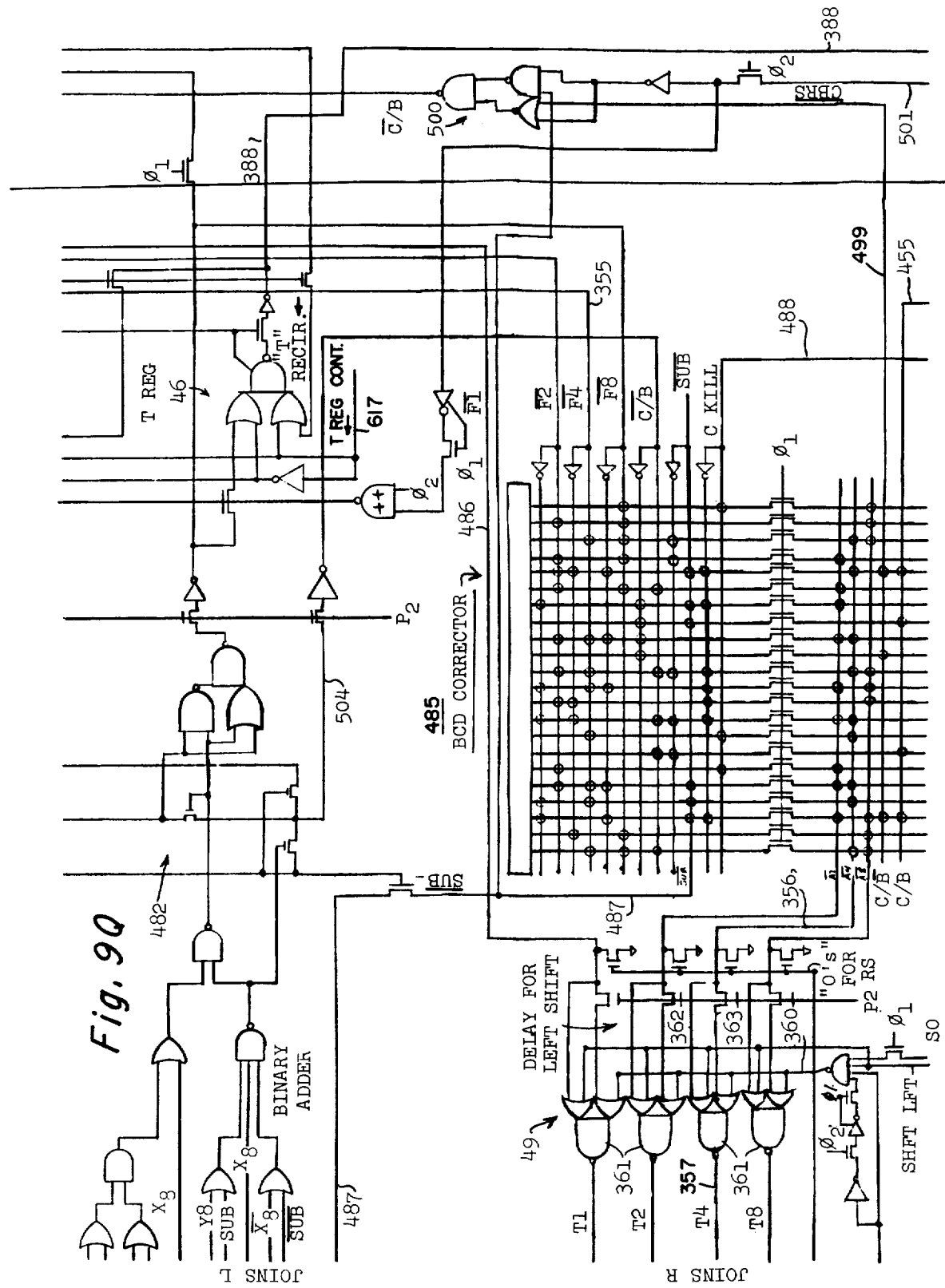
Figure 9R:
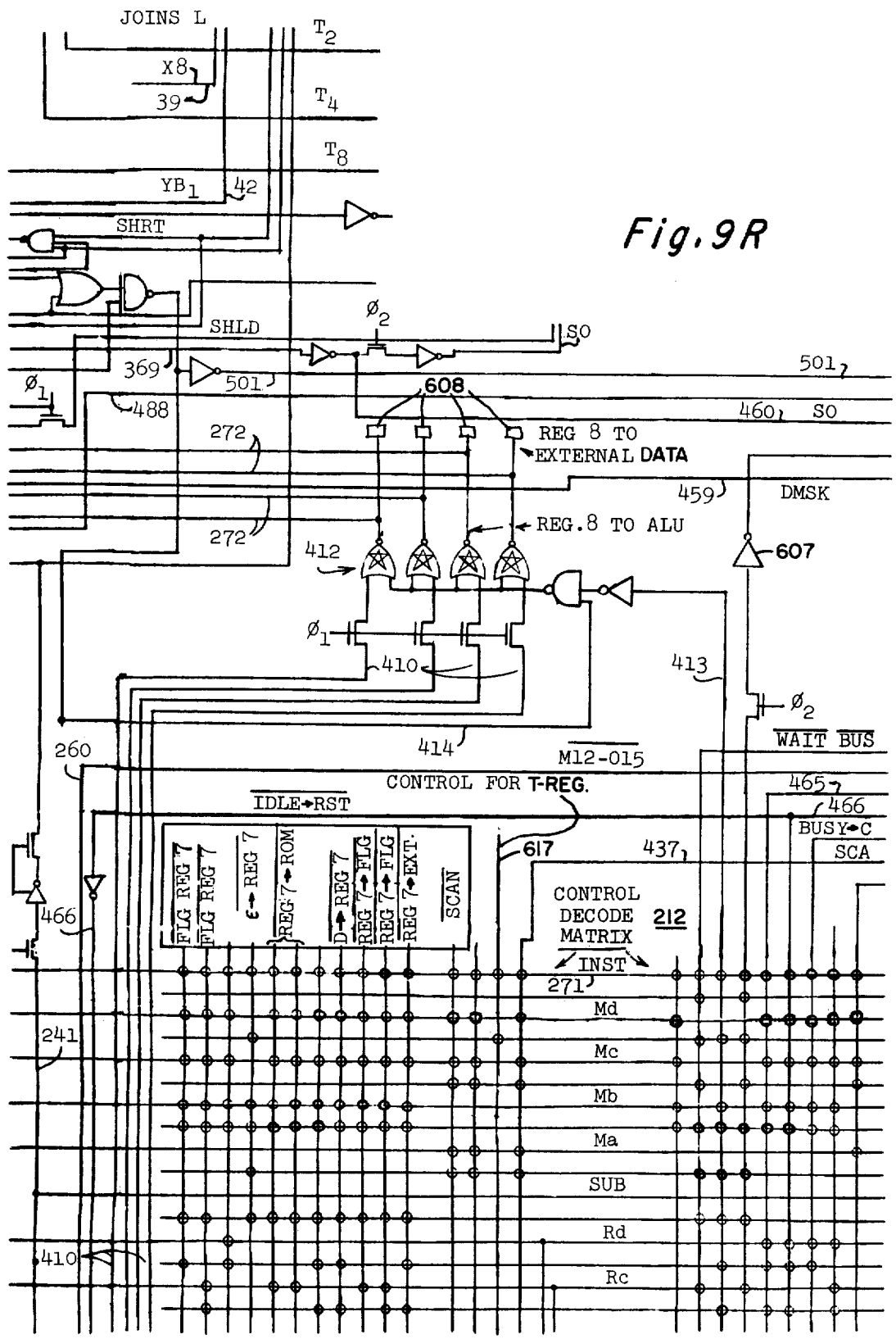
Figure 9S:
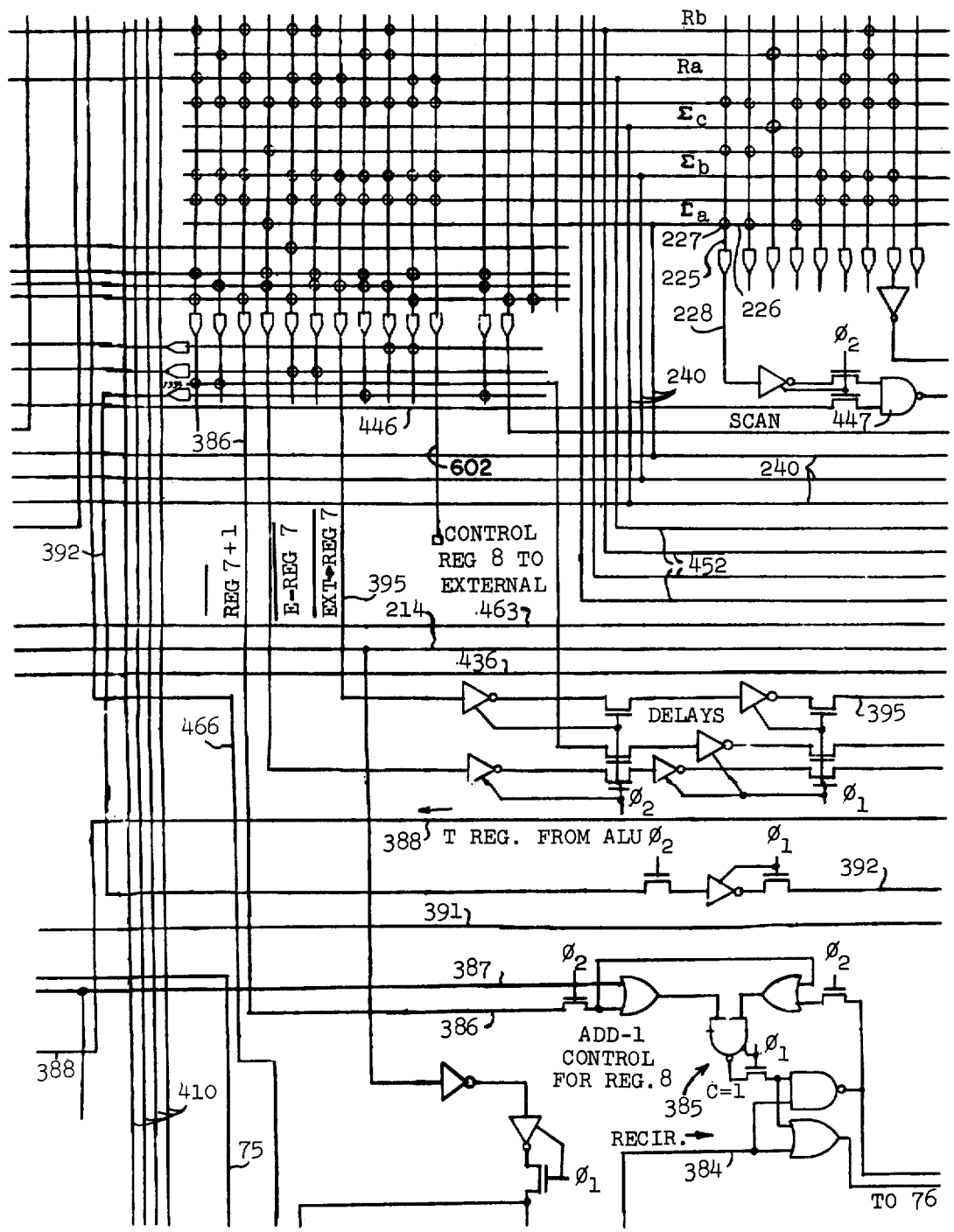
Figure 9T:
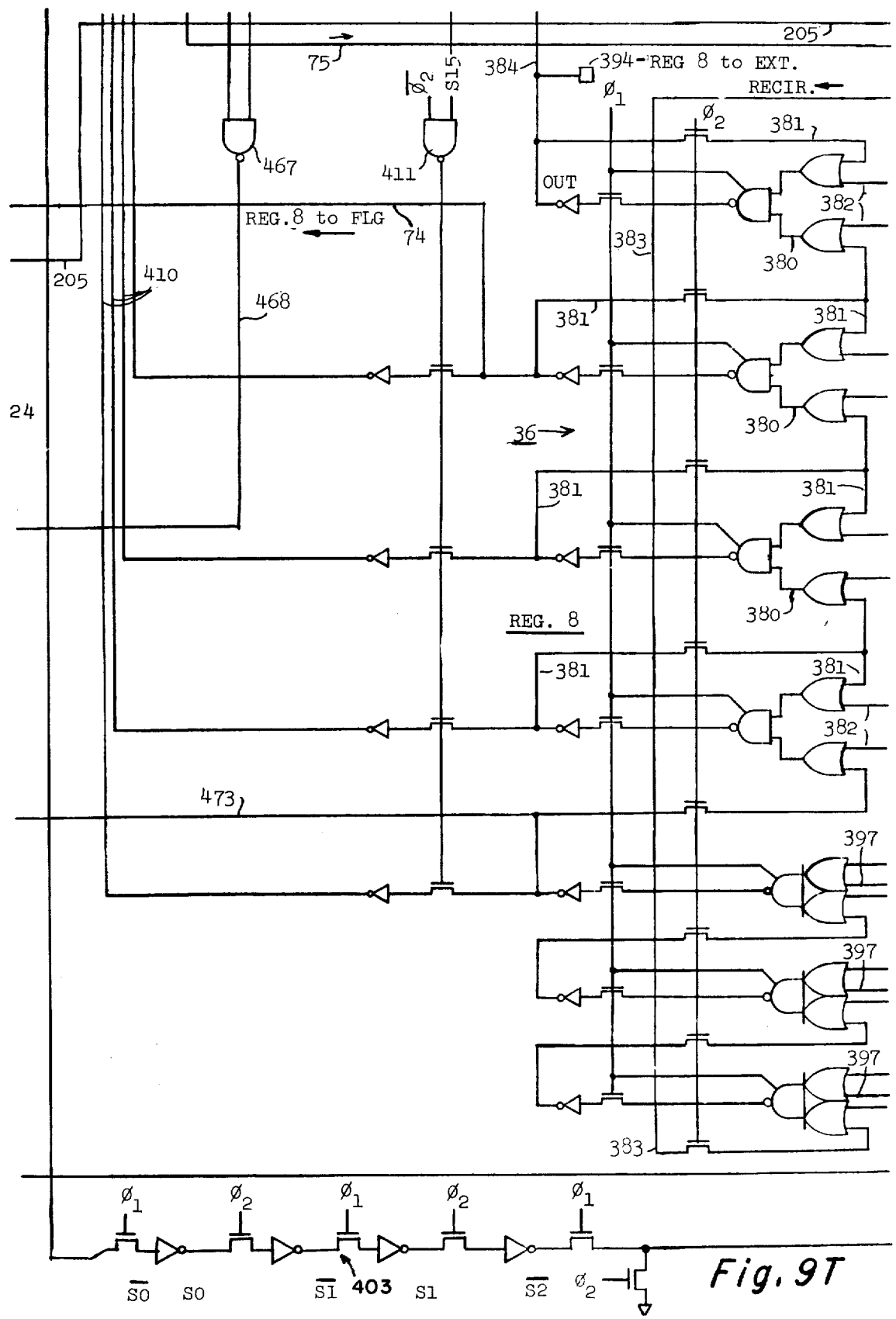
Figure 9U:
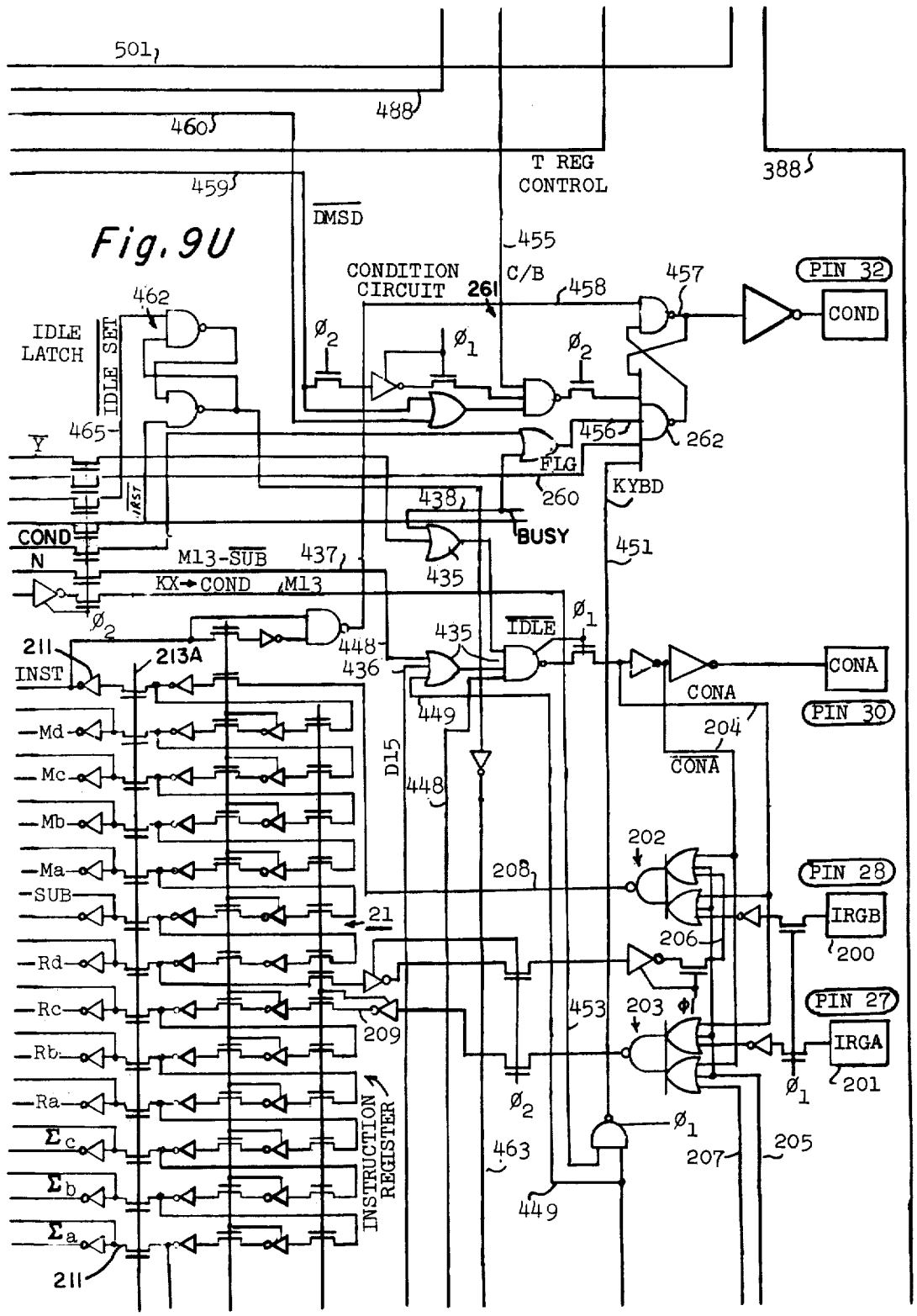

Referring to FIG. 9U, the instruction register 21 is seen to include a pair of inputs 200 and 201, also labeled PIN 27 and PIN 28, which receive the instruction word serially in two parts from the ROM chip. The instruction word of 13 bits is broken up into seven bits coming in on the input 200 and six bits coming in on the line 201; this is merely to save time in transferring the words serially, and has no other significance in the logic of operation of the system. The instruction word is fed from the inputs 200 and 201 through two selection gates 202 and 203, which are controlled by several inputs. One pair of inputs 204, called CONA and $\overline{\text{CONA}}$, mean that an "inhibit increment" command is or is not present. When present, a new word is not accepted, but instead the one in the register 21 is recirculated. Another input 205, when present, causes the instruction word to be blocked from reaching the instruction register so that all zeros will be produced in the register; this is when a P-REG or program register instruction is sent to the ROM chip. The input on line 205 is obtained from a P register output circuit, FIG. 9 "0", to be described below. Other inputs 206 and 207 are for recirculation from the instruction register 21, so the instruction word in the register will continue to recirculate when other conditions are met. The outputs of the gates 202 and 203 are fed by lines 208 and 209 serially into inputs of a thirteen stage recirculating shift register which is actually broken up into two separate registers of seven and six bits. The register is of conventional form, employing two inverters and $\phi_1$-$\phi_2$ switches in each stage. A fourteenth stage 210 is added at the end to introduce a delay so both parts of the register will be operating in synchronization. The thirteen outputs 211 of the instruction register 21 are labeled, as described elsewhere: Inst., M field, Sub, R field and $\Sigma$ field. The complements of these thirteen items are also included, so a total of twenty-six lines go into a control matrix 212, FIGS. 9R and 9S. The instruction word is being read in or is recirculating serially in two parts, so it is only at a particular time that the word in the register will have any meaning; thus, the contents of the register 21 are applied to the control matrix only when an output appears at a gate 213. One input to the gate 213 is a time signal S14 or state time 14 on a line 214. The time S0 to S13 is used for the register 21 to be filled in an instruction cycle. The state time S15 is occupied by the delay in decoding in the matrix 212. A new instruction word is thus presented for operation at the end of an instruction cycle, i.e., one instruction cycle is used to load a new word, then the operation commanded by that word can be carried out while another word is being loaded.

Decoding the Instruction Word-The Matrixes

The output of the instruction register goes to a control matrix 212 and also to a sigma and flat matrix 220, an R decode matrix 221, and M or mask decode matrix 222, as well as to other places as will appear. Each matrix is a programmable logic array of well known construction, described later with reference to FIG. 12. A vertical line such as a line 225 at the lower edge of the control matrix 212 represents a P diffusion, a horizontal line 226 (one of the $\Sigma$ lines) represents a metal stripe, and a circle 227 at an intersection represents a gate or thin oxide so that an MOS transistor is created. The other P diffusion line for drains is not shown. In some of the matrixes of FIG. 9, the P diffusion lines are horizontal and the metallizaion lines are vertical, of course. As an example, the transistor 227 formed at the intersection of lines 225 and 226 is part of a NOR gate, with the other inputs for the vertical line 225 being at $\overline{\Sigma}_b$, $\overline{\Sigma}_c$, $\overline{\text{Ma}}$, Mb, Mc, Md and Inst.; the presence of any of these changes the output on line 228, which incidentally is one of the inputs to the inhibit increment logic.

The R field of the instruction word is connected directly to inputs 230 of R decode matrix 221, FIG. 9M. That is, even though the Ra, Rb, Rc and Rd lines pass through the control matrix 212 at this point, the R field appears unaltered at the inputs 230. In addition, the Ra-Rd lines are inverted so that $\overline{\text{Ra}}$-$\overline{\text{Rd}}$ inputs 231 are also applied to the decode matrix 221. The four output lines 232 from the R decode matrix go to a set of sixteen gates 233, FIGS. 9K, L, M, which determine what main register output goes to the ALU. Thus, in order for the outputs 37 of A register 30 to pass through the gates 233, a line 234 in the R decode output 233 must be on. This would be true for various combinations of presence and absence of the signals in the R field of the instruction word, depending on how the decode matrix 221 is programmed.

The Σ field lines 240 are applied from the output of instruction register 21 to inputs of sigma and flag matrix 220, FIG. 9c, along with subtract or Sub line 241, and their complements. This matrix 220 receives the outputs from the flag registers 34 and 35 which appear at inputs 242 and 243 to the matrix 220, and also these inputs are inverted as are other inputs to the matrix. Another input 244 to the flag matrix is from a line 244 on which the complement of M15 appears. M15 is decoded at a logic gate 245, FIG. 9M, which receives as inputs the mask or M field, Ma-Md, from the instruction register 21. M15 is an indication that a flag operation is commanded, and is used in several places. Other inputs to the flag matrix include a flag mask indication on a line 246 which is generated at logic gates 247 as will be described. An input 74 to the flag matrix 220 is from an output of the recirculating special register 36 or REG8. Also, the lines 240, the Sub line 241, and the complement of M15, on line 244, all are connected as inputs to gate 248, the output of which is an input 249 to the flag matrix.

The function of the sigma and flag matrix 220 includes decoding the Σ field from the instruction register 21, and also controlling recirculation of the flags in the flag registers 34 and 35. The decoded Σ outputs from the matrix 220 appear on groups of lines 255 and 256, FIG. 9B, after going through logic gates 257. One input 258 to these gates 257 is an output from the mask decoder 222, and functions as a digit mask to specify what part of the data word is operated on, i.e., mantissa or what.

The decoded Σ outputs 255 represent an instruction (or its complement) to transfer data between A and B registers or between C and D registers. The decoded Σ outputs 256 represent a recirculation command for A, B, C or D registers. The outputs 255 and 256 are connected to the sets of selector gates 56, 57, 58 and 59 on the left-hand side of the SAM, FIG. 9A, to control recirculation or exchange of data in the main registers. These outputs 255 and 256 are further connected to a Σ decode array 259 which is another programmable logic array (with saturated loads) that produces four outputs 260 to control further sets of selector gates 56, 57, 58 and 59 for the A, B, C and D registers on the right-hand side of the SAM, FIGS. 9K, L, M; these selector gates control which one of the main registers receives the output 55 from the T register 46 in the ALU 24.

Figure 9V:
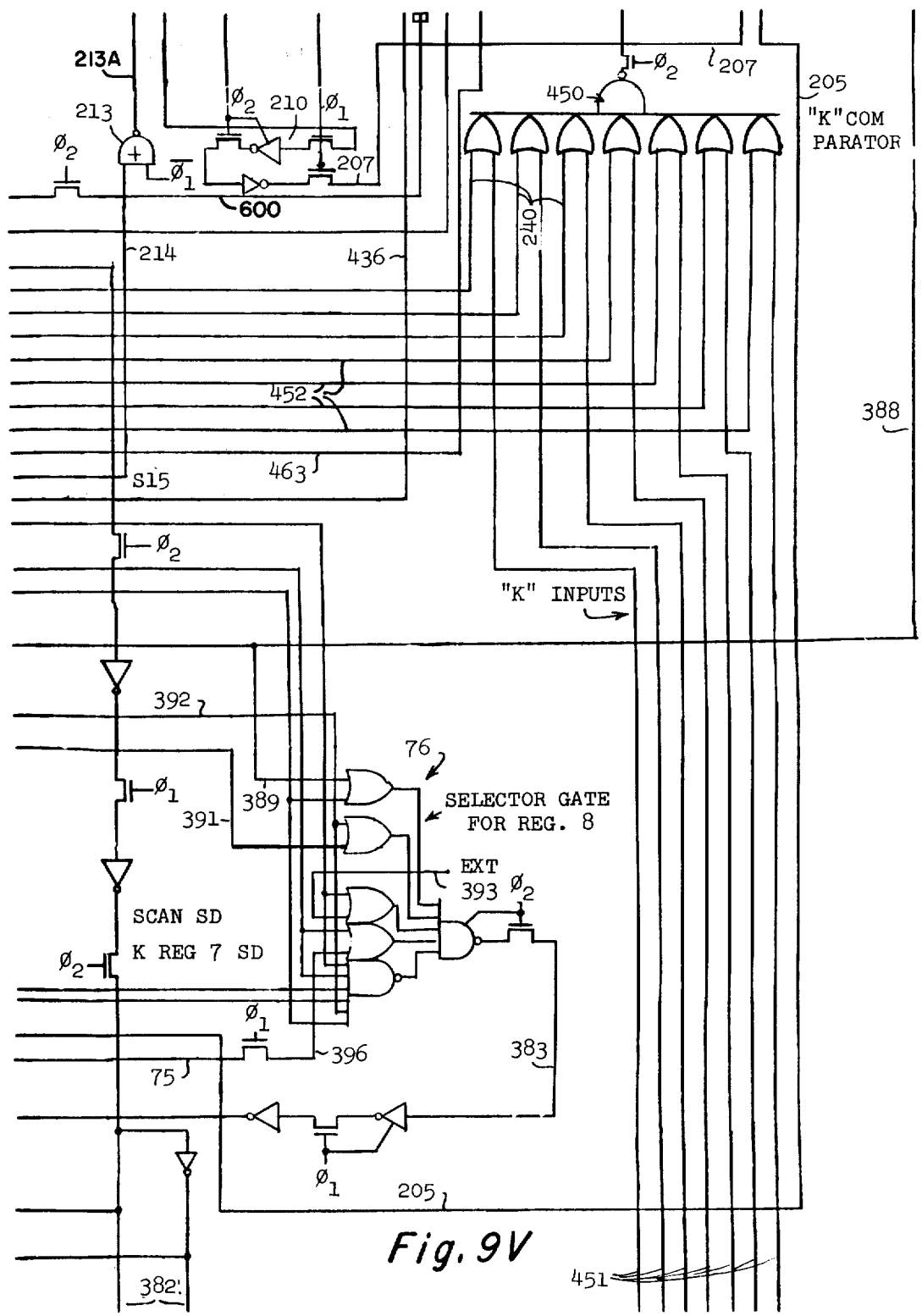

Other outputs from the flag matrix 220 include an output 260 which is inverted and connected back to a condition circuit 261, FIG. 9u, as one of the inputs to a gate 262 to indicate that two flags are the same. The condition circuit will be described later. Another output 263 goes to a gate at the chip output PIN 6, FIG. 9A, for comma indication and also to a set of gates 264 which control flag recirculate or exchange. An output 265 goes to the gates 264 and to selector gates for PIN 11 for flag A or FLGA output from the chip. The gates 264 also receive an output 261A from the matrix. The outputs of flag A and flag B registers, from the complements of lines 242 and 243, are connected through the flag matrix 220 and logic gates 266, FIG. 9H, to provide the connection 75 to the selector gate 76 for the 8 bit register 36, FIG. 9V; this input provides the flag register input to the register 36 or REG8. One or the other of flag A or flag B registers is selected by the Sub line 241, since Sub and its complement are inputs to gates 266.

The mask decoder or M decode matrix 222, FIG. 9M, receives the M field and its complements from lines 270 at the output of the instruction register 21, and also the Inst. bit on line 271. If the Inst. bit is a zero, the instruction is a branch rather than an operation so no output commands are to be given by the mask decoder and to accomplish this circles are seen at every intersection for this input line 271 in the matrix 222. Mask outputs include a set of four lines 272 which provide a constant or N input to the ALU 24, or the input 43 to the Y bus of FIG. 3. Other outputs include the digit mask 258 going to the Σ selector gates 257 as mentioned above, and the other end of this output is also connected by a line 273 to a logic group 274 which controls in part right shift, left shift, carry/borrow, reset, as will be explained; this permits the part of the word to be right shifted to be controlled by a mask. Further inputs to the mask decoder 222 are outputs 275 and their complements, from a push-pull matrix 280, FIG. 9G; these comprise encoded state times, or S0 to S15 encoded on four lines. Further, inputs to the mask decoder 222 from the push-pull matrix 280 include a decimal point or DPT indicator on line 276 which shows the line to be activated at S15, meaning S0 will be the programmed DPT time since the voltage on line 276 is gated into the matrix 222 on $\phi_2$ and lasts until the next $\phi_2$. Line 277 likewise defines the position of the exponent, here S0 or actually S1 time. And, line 278 defines the mantissa as S2 through S14 by circles at address lines S1 to S13.

The Sequentially Addressed Memory (SAM) and Push-Pull Matrixes

The main A, B, C and D registers are contained within a random access memory arrangement 23 which is operated in a manner similar to a set of shift registers, as set forth in co-pending application Ser. No. 163,683. The SAM 23 includes an A register 30 which is comprised of four separate rows $A_1$, $A_2$, $A_4$ and $A_8$, in BCD format. Likewise, the B, C and D registers each comprise four rows $B_1$, $B_2$, etc; these are interleaved to save space in interconnecting the registers on the chip. Each row includes sixteen cells 300 or one for each digit or character, with each cell being a conventional three-transistor RAM memory cell. All of the memory cells 300 in the SAM are exactly the same, and there are a total of 16×16 or 256 cells in the main A, B, C and D registers. The SAM also includes two flag registers 34 and 35, which are sixteen bit rows, or thirty-two more cells, for a total of 288 cells in the SAM. Vertical lines in the SAM are address lines 301 of which there are seventeen, these bit lines being driven by a commutator 302, FIG. 9E, made up of a seventeen stage (or sixteen and one half stage) ring counter which circulates a zero in synch with state times. Indeed, the commutator 302 generates the state times S0-S15 for use throughout the system. Only one of the address lines 301 is energized at any one time, and the energized line shifts from right to left in the order S0, S1, S2 . . . S15, S0, one at a time, producing the signals seen in FIG. 5A. Each stage of the commutator comprises two inverters 303 and 304, and two switches 305 and 306 driven by $\phi_2$ and $\phi_1$. The outputs of the commutator stages are coupled thru inverting gates 307 to the bit lines and to an OR gate line 308 in a push-pull matrix 310. A recirculate signal is coupled back to the beginning by line 308 when the zero propagating thru the commutator passes S14; thus, the S0 line of both edges of the SAM will be energized at the same time.

On top and on bottom of the SAM 23 are located a pair of push-pull matrixes 310 and 280 which function to generate a number of timing signals, as mentioned above. The combination of the SAM with the push-pull matrixes is an important feature of the invention. Four lines 312 as outputs of the matrix 310 provide an encoded indication of the sixteen state times S0-S15 for conveying to the ROM chip thru outputs SA, SB, SC, SD. Non-inverting buffers, not described in detail herein, are in series with these outputs. The lower push-pull matrix 280 includes seven output 275-278 to the mask decoder 222, as mentioned above, and also an output line 320 which generates an S14 indication which is gated at $\phi_2$ and then used to generate an S15-$\phi_1$ time indication in a gate 321. S15-$\phi_1$ is used to indicate the beginning of an instruction cycle in generating digit or D times; this indication is used to open a set of gates 322 which are in series with a set of four lines 323 connected to the lower four output lines of the push-pull matrix 280 on which appears S0-S15, the sixteen state times encoded on four lines. These encoded state times are strobed at gates 324 by the output of a gate 325 which receives $\bar{\phi}_2$ and a strobe signal as inputs. The strobe signal on line 326 is obtained from an output 327 from a programmable strobe counter as will be described. A strobe signal appears on line 326 every fifteen state times; so the encoded S time number allowed through the gate 324 will count backwards. Two inverters are in series with each of the lines 323; the inverted output of three of the lines and twice inverted output of the forth produces a $\overline{D1}$ indication at a gate 328, the output 329 from this gate being used to initiate a set of display scans in a display scanner as will be described. Encoded digit timing is provided on the lines 330 which are the state times from lines 323 as allowed through by the strobe $\bar{\phi}_2$ gate 324 and S15-$\phi_1$ at gate 321. Encoded state times are available at this point on lines 331. The state and digit times are used in several places as will be described.

The lines 330 or D time output will never read zero. Fifteen D times as seen in FIG. 5B, while the S time cycle through sixteen states. A strobe occurs every fifteenth S time. The lines 275 in matrix 280 are programmed to read out a number in binary which is one ahead of where the "0" is on the address lines; so, when the S0 line is actuated, the lines 323 are reading out a one instead of zero. This is seen in FIG. 5C, which is a table of when the gate 324 opens, when the gate 322 opens, and what appears on the lines 323, 319 and 330. No zero will be read out on lines 330; a zero will appear on lines 319 at S15-$\phi_2$ and will stay there until S14-$\phi_2$, but during this time S15-$\phi_1$ will not have occured to open the gates 322, thus the zero will not reach lines 330.

Another output from the matrix 280 is a line 332 which provides an input $\overline{DBLK}$ or digit blank to the output NAND gates of the display scan. The timing signal $\overline{DBLK}$ on line 332 begins at S1 and ends after S14, for each instruction cycle. This functions to blank the display during S0 and S15, i.e., the display is activated only S1 to S14. This is needed for some types of displays.

The operation of the SAM will now be described. When an energizing voltage or "0", a negative voltage, appears on the S0 address line, all of the MOS transistors 340 (looking now at the S0 cell for the B4 row in the B register) which act as the output switches for the memory cells 300 in the S0 vertical column will be made conductive, so the gate storage capacitor of a cell will, if it is charged negative, cause the transistor 341 of the cell to be also conductive, and the output line 342 will be grounded. Thus, if an "0" is stored, a "1" will appear on output line 342; "1" is ground or $V_{ss}$, "0" is a negative voltage or $V_{DD}$. This output line 342 is inverted at 339 so the output line 40 will be in "false" rather than "true" logic; bits are stored in false or complementary logic. The output from the left-hand end of the line 342 goes into a one-bit delay circuit 60. Each one-bit delay includes two inverters and $\phi_1$, $\phi_2$ switches. Depending upon the settings of the $\Sigma$ select gates 57, etc., this bit can be either recirculated, or passed through the ALU, left-shifted, right-shifted, etc. If the bit is to be merely recirculated the gates 57 are set by the then-present instruction word so it will pass through a complex gate 343, 344 to appear inverted on line 345, delayed by one and one half state times; that is, the bit leaves its storage capacitor on $\phi_1$ of a given state time, that state time proceeds through $\phi_1$-$P_1$-$\phi_2$-$P_2$ as in FIG. 5A as the bit propogates through the delay 60; the S0 address line becomes de-energized or goes to ground at the end of $\phi_2$, and S1 goes negative on $\phi_1$ of the next state time as the commutator 302 switches to the next stage to the left. On $\phi_2$ of this next state time, gate 343 is enabled by $\phi_2$ which is one of its inputs, so the bit can proceed to line 345. Back at the cell; the transistor 346 is now conductive, and the bit will be re-entered into the same cell it came out of. All bits in all cells 300 of this first vertical column S0 will be recirculated or refreshed during S0-S1 time, during every cycle, unless they are being transferred or operated on in the ALU, or shifted. If the bits in B register are being transferred to the A register, the gates 56 and 57 are activated by the decoded $\Sigma$ field appearing on lines 255 and 256 in such manner that the bit on output line 342 will not go through gate 343 but instead will go by line 347 through gates 348 and 349 to A4 input lines 350. As before, when line S1 comes on in the next state time, the bit will go back into a memory cell, but this time it will go into cell 351 in A4. In this manner during one instruction cycle or digit time, all of the sixteen bits in the B register may be transferred one at a time into the A register. The bit may instead go through the ALU; if the B line of the output lines 232 from the R decode matrix 221 is on, the bit will go through a complex NOR/NAND/INVERT gate 352, 353 to Y4 bus 42. The gate 353 can also pass a bit on line 354 if a constant N is to be entered into the ALU from lines 272, as described elsewhere; in such case the gate 352 would not pass the bit from B4. The bit on Y4, line 42 goes through the bit 4 path of the ALU 24 and the bit 4 path of the carry/borrow circuit, to appear on an output 355. Also, the bit could go into the T register 46. The output line 355 goes into the $\overline{F4}$ input of a BCD corrector matrix FIG. 9Q, as will be described, from which it appears as an output 356 which goes into a left shift circuit 49. If neither right or left shifted, it appears on T4 line 357 and then back through one of the $\Sigma$ selector gates, the B4 gate 57 as controlled by decoded $\Sigma$ lines 260, and through a right shift control gate 358 to reappear on line 345 and be re-entered into the same cell via the transistor 346, since S1 line is now on. The time required for this path is again one and a half state times. The gates labeled 57 and 358 are actually part of a complex open-drain NOR/NAND-/INVERT gate, rather than being separate.

The flag registers 34 and 35 operate in a manner similar to the A, B, C, D registers, except that the data in these registers cannot go through the ALU. Output from flag register A on a line 290, and output from flag register B on line 291, go into the flag matrix 220 via 242, 243 and inverted lines. Gates 292 to horizontal lines 293 provide a recirculation path to matrix outputs 263 and 265 as mentioned above. To swap or exchange a bit in flag A with a bit in Flag register B, lines have gates on the matrix output which are reversed, so exchange of flags is accomplished within the matrix, meaning that a proper combination of Σ, Sub, and FMSK inputs will determine to the matrix whether bits are recirculated or exchanged. Other inputs to gates 264 are the outputs 295 and 296 which function to clear all A flags or clear all B flags when a certain combination of Σ and Sub fields exists, along with inverted M15 on line 244.

All of the input and output lines for the SAM are precharged to $V_{DD}$ for each state time. All output lines such as line 342 are precharged at P2 by switches 297, FIG. 9E. During P2, all address lines are off, as seen from FIG. 5A. All input lines are precharged at P1 by switches 298. Significant input information does not have to be present until $\phi_2$ of each state time, so precharging at P1 does not interfere with the data. Precharging provides a DC power saving.

Left and Right Shift Circuits

The left shift circuit 49 functions to add a one state time or one bit delay to produce left shift. The control for left shift is a pair of lines 360 going to comples NOR/NAND/INVERT gates 361. When not energized for left-shift, the path of the bit on line 356 is via line 362, on which it appears at $\phi_1$, and no delay occurs; but where energized for left-shift, the path via line 362 is closed, and the bit is delayed until P2 before reaching line 363 then is allowed to pass through the lower part of the complex gate 361 at the next state time. The bit will then follow the same path as before, i.e., T4 line 357, Σ select gate 57 and gate 358 to B4 input line 345; however, the S0 and S1 bit lines have by now both gone off, and S2 is on, so the bit will be entered into memory cell 364, or the next one to the left.

Right shift occurs when a right shift command appears on a line 365, which goes to a right shift selector gate 366 which a NOR part of a complex gate. The bit described above, read out from B4, at the beginning of S0, goes through the path 342, 40, 352 and appears at the output of gate 353, from which it appears as an input 367 to gate 366. This gate is enabled. So, rather than being delayed one and a half state times, the bit appears immediately on B4 input line via gate 358; since S0 is still on, rather than S1, the bit cannot be re-entered into the same cell. Instead, the bit will be right shifted, and in this case, lost or discarded, because there are no cells to the right. If the bit had come out of one of the centrally located cells, it would go back into the one on its right during the same state time.

The shift commands are generated on a line 370 at the output of R decode matrix 221 when a predetermined combination of R inputs exists, in combination with the subtract command on line 371 which is derived via line 241 from the instruction register 21. Also, the digit mask on line 273 is an input to logic 274, and state 0 time from address line So in the SAM, via line 369. The logic arrangement 274 produces the right shift enable on line 365 and the left shift commands on lines 360, and also disenables the subtract command at a gate 372 via a line 373. The subtract instruction from the instruction register cannot be used directly because it also determines left shift and right shift.

The 8-Bit Special Purpose Register

The special purpose register 36, FIGS. 9T, V, W, operates as a recirculating shift register. It is comprised of seven conventional shift register stages 380, and one bit is provided in the output of selection gating arrangement 76. The upper four of the stages 380 can recirculate internally via paths 381, as determined by SCAN and $\overline{SCAN}$ control inputs 382. The lower three stages 380, which are the first three stages of the register, cannot recirculate internally, but the entire register can recirculate. Data from selection logic 76 may be entered into the lower three stages, serially, via a line 383 when the entire register is recirculating via a path 384, and an add-1 command can be inserted at this path in the appropriate time slot by add-one logic 385. The add-one logic receives an input 386 from control matrix 212 upon the occurrence of the appropriate instruction word, and also receives a timing signal via line 387 derived from S14 line 214. The input 386 from matrix 212 is also time related due to SC and SD inputs 376 and 377 which are applied to the matrix along with their complements. These are obtained from push-pull matrix 280; only SC and SD are needed since the time-related outputs of the control matrix 212 are all in quarters of a D time, i.e., four or eight S times.

Other possible inputs to the register 36 include the T register output from the ALU appearing serially on line 388 and going into the selection gates 76 via a line 389. Also, the serial output of D register or digit register 390 may be applied to the gate 76 via a line 391. The command for entering the D register into the 8 bit register 36 is applied to selection gate 76 via a line 392 which is an output from the control matrix 212. This output 392 occurs upon a selected instruction word, and is time related due to the SC and SD inputs to the matrix. External imputs may also be entered into the register 36 via input line 393, and the register outputed serially via line 394, but these connections are not used for the particular system described herein; external input would be controlled via line 935 from the control matrix 212. Data from the flag registers is entered at an input 396 which is the same as line 76 of FIG. 3.

Keyboard "K" information is entered into the register 36 in parallel to the lower three bits or stages via lines 397 from a keyboard encode matrix 400. The seven parallel K or keyboard inputs to the chip are provided by PIN 18 to PIN 25, which are applied to latch circuits 401 that function to hold a given key input for one D time or instruction cycle. The seven latch circuit outputs are encoded to three lines by the matrix 400, which is a programmed logic array. The keyboard is strobed, or the latches 401 set, by a timing signal on line 402 which is connected thru a delay arrangment 403 to the timing line 387, as was derived from S14 at line 214. In this manner, once every instruction cycle the K lines will be looked at and whatever they read will be entered into the latches 401 and a three line encoding of this is available on lines 397 to be entered into the lower three bits of special register 36.

A direct output from the keyboard KQ input latch 401 via line 404 provides hardware clear; the "clear all" key is thus connected by this path to by-pass everything so if the machine is stuck in a program loop and cannot scan the keyboard then the unconditional clear operation will still work. The line 404 along with D15 time on line 405 provide this function as inputs to a gate 406 in the P or program register output circuit as will be described.

When encoded keyboard data is coming into the lower three bits of register 36 in parallel via lines 397, the upper four bits recirculate upon themselves via 381 under control of commands on lines 382 from the control matrix. The four bits in the upper stages would be encoded D times from line 391, so a seven bit word is provided in the register which defines the keyboard input by D's and K's.

Four bits may be conveyed in parallel from the register 36 to the Y bus of the ALU 24 via lines 410, at S15-$\phi_2$ under control of gate 411, the lines 410 go into selector gates 412 which are controlled by an output 413 from the control matrix 212 and another command on line 414 from the left-right shift logic 274. The other output from register 36 is the line 74 going to flag logic 220 and thus to the flag registers.

The register 36 is used mainly for interfacing with the keyboard, but it also may be loaded from the flag registers, from the ALU, or from the digit time register, and it may be incremented by one. The contents of the register may be sent to the flag registers or the Y input of the ALU.

The Digit Register and Decimal Point Logic

The D register 390, FIG. 9I, receives the fifteen encoded D times or digit times in parallel on input lines 330 encoded in binary, and a delayed S14 time on input line 415, to drive a four stage shift register 416, from which D times are read out serially in four bits, on the line 391. The recirculation in the four bit register is under control of $\phi_1$ and $\phi_2$; a complete read out occurs four times within an instruction cycle, once very four state times, then a new D time is entered by lines 330.

One use made of the serial D time output is in a decimal point comparator 420, which has the D time output line 391 as one of its inputs and an adjusted decimal point or DPT value on line 421 as another input, and functions to compare the four bit number appearing serially on one line to the four bit number appearing serially on the other. The remaining input to the DPT comparator is an S15 time signal on a line 422. The comparator circuit includes a latch 423 which latches on when the DPT value and the D time is the same, and this produces an output via 424 which goes to PIN 5, DPT. This output is used by the display to energize a decimal point indicator at the selected digit.

The adjusted decimal point indication on line 421 going into the comparator 420 is generated in DPT adjustor circuit 430, which receives one input 431 from the push-pull matrix 280 and another input 388 from the T register. The line 431 has a recurring four bit number appearing serially on it, as programmed in the push-pull matrix; in the embodiment shown, this four bit number is a three, or 0011 in binary, and it is repeated four times every instruction cycle. The circles on address lines (intersections of line 432) S0, S1, S4, S5, S8, S9, S12 and S13 indicate that a 1 of produced on the line 432 at these S times, thus reading out "1-1-0-0-1-1-0-0...". This part of the matrix is thus programmed to generate a constant binary number 0011, and this constant is added to a binary number received a line 388 from the T register 46. The T register output is also a four bit serial number, as derived in the ALU, and in this case would be the position of the decimal point. The number "3" is added because the first two places are used for exponent and DPT in the main registers, and the DPT indicator on line 424 should appear before the digit for which the DPT is reached in the MSD to LSD display scan of D scan. So, if the number in the T register says the DPT should appear in the fifth place, as to display 1234.56789, a constant "3" added to this makes the DPT indicator to appear at output 424 at D8 rather than D5.

State Time/Digit Time/Flag Comparators

A comparator 440, in FIG. 9N receives, as one set of inputs, the R field on lines 441 from the instruction register; a flag operation occurs only when M15 occurs and this is present on line 244 as one input to logic arrangement 442, the output of which also appears as input lines 443 to the comparator 440. The complex logic gates 442 receive state times from lines 331 as one set of inputs, and receives D times from lines 330 as the other set of inputs. The output 443 of logic 442 is encoded state times when M15 is present, i.e., a flag operation is commanded, and is D times at all other time. The output 445 of comparator 440 will be a comparison of a particular flag from R field and a particular state time, and this goes into logic gate 247, the output 246 of which is the flag mask input to the flag matrix 220. The other input 444 to the gates 247 is an indication from control matrix 212 which means data from register 36 is being put into the flag registers. Flag indication M15 from line 244 is also applied to gates 247. The output of the comparator 440 is also applied by a line 446 to gate 447 going to the "inhibit increment" logic.

Inhibit Increment

A connection from PIN 30, FIG. 9U, to the ROM chip functions to prevent or inhibit the program counter 25 from being incremented—this is referred to as CONA or inhibit increment. This command is generated by a complex gate 435 which receives one input via line 448 from gate 447 just mentioned above, another input 449 from a comparator 450 to be described below, and a third input via line 436 inverted from the D15 line 405 in FIG. 9-O. A fourth input via a line 437 from the M field and Sub in the control matrix 212 indicates M13-$\overline{SUB}$. A busy signal from PIN 29 could be another input via line 438; this would be used if a printer were attached, and would indicate, for example, that the printer was still busy and the program counter should not be incremented until printing of previous data is completed.

The comparator 450 specifies a particular keyboard input and produces outputs to inhibit increment and also to the condition circuit 261 which produces COND, PIN 32. Inputs to the comparator 450 include the three bit $\Sigma$ field on lines 240, the seven K inputs on lines 451 from the keyboard matrix 400, and the four bit R field on lines 452 from the instruction register output. When the K field is the same as that specified by $\Sigma$ and R fields, the comparator 450 output on line 451 appears as an input to the gate 262 in the condition circuit 261.

The Condition Circuit

The condition circuit 261, FIG. 9U, further receives a carry/borrow input on line 455 from the BCD decoder, as well as a busy condition indication on line 456 (not used in this embodiment). The flag input 260 means that two flags are the same. A "condition" or COND output is used for branch instructions; the output is through a latch 457 operated by an Inst. output from the instruction register 21 appearing through a NAND gate on line 458. Inverted digit mask is applied to the C/B part of the condition circuit via line 459, and $\overline{S0}$ is applied via line 460.

Idle Latch

An idle latch circuit 462 produces an output on a line 463 which goes to PIN 11, FLGA output to the display. During a software loop which scans the keyboard for a key to be depressed, the A flags are displayed, thus the latch output to the flag display output. Also, this latch output goes to a latch 464, FIG. 9D, in the control for the display scan of FIG. 9J. During the idle loop, the A register is displayed, so idle latch enables the display. A "set idle latch" input 465 from the control matrix 212 sets the latch when specified by the program, and the latch is reset by an input 466 from the matrix. This "idle reset" command on line 466 is also applied to a NAND gate 467, FIG. 9T, which receives S15 as its other input (from 214); the NAND output is applied via line 468 to a power up clear circuit 470, FIG. 9D.

Power Up Clear

The power up clear circuit 470 assures that the machine is initiallized correctly. The program counter 25 is forced to zero. A "reset idle latch" at location "0" forces the machine out of location "0". The circuit 470, upon receiving the reset command on line 468, generates "0" on line 469 going to P register output circuit 471, FIG. 9-O. When power is turned on, all the register contents, values of flags, etc., are unknown and should be cleared or set to known values.

The Program Register Output Circuit

An output to the program register 25 in the ROM chip is provided at PIN 17. This output is controlled by circuit 471. When an address is to be sent to the ROM chip, a command is made to appear at output 472 from the control matrix 212. The address to be sent out is coupled from special register 36 via line 473 as an inverted input to NAND gate 474. When an address is sent, it always is eight bits long and starts with "0"; when the ROM chip sees a "0" at S4, it knows that the data chip is sending an address. The next seven bits are the address. A latch 475 is provided to keep putting out zeros to the end of the instruction cycle. The latch is set by an input 476 from the command input, and reset by an input 477 from delayed S14 line 387.

The Arithmetic Logic Unit

The ALU 24 comprises a binary adder made up of four sets of complex gates 480 and 481. The 480 sequence is a complex logic gate having SUB, $\overline{SUB}$, X, $Y_1$, $\overline{Y}_1$ inputs. The 481 sequence is NOR/NAND with the same five inputs. These function to add or subtract a binary number appearing on $X_1$ and $Y_1$ lines 39 and 42, and to produce a carry/borrow input to C/B circuit 482. The logic arrangement chosen was to provide fast operation, i.e., to allow the ALU operation to occur within one state time. The $X_2$-$Y_2$, $X_4$-$Y_4$ and $X_8$-$Y_8$ parts of the ALU are the same as $X_1$-$Y_1$. The data into the ALU is BCD, yet it is operated on as if it were binary, so to convert back to BCD a corrector matrix 485 is used. The "1" output, F1 on line 486, need not be corrected and so it bypasses the corrector. The F2, F4, F8 and C/B lines go through the corrector 485 which is a programmable logic array. Other inputs are SUB on line 487, and CKILL or corrector kill on line 488 which prevents the corrector from operating on S0 which is the decimal point location. So, DPT is carried in straight binary rather than BCD. CKILL on line 488 is generated in push-pull matrix 280, by a gate at SO. Outputs from the corrector 485 include 2, 4 and 8 inputs to the left shift selector 49, and C/B, $\overline{C/B}$ outputs on lines 455 and 499. The carry/borrow output goes to a C/B gate circuit 500 which keeps C/B from propagating over from prior bit. Inputs are SUB from line 487, and C/B reset on line 501 which is generated from a digit mask edge by shift control circuit 274. The output 502 from C/B gate circuit 500 is connected to a transistor 503 in the first bit of C/B circuit 482. The carry circuit operates as explained in co-pending applications Ser. No. 176,667 (TI 4658, TI-4660) C/B output is provided at 504, from which it is connected for BCD correction.

The Display Outputs and Zero Suppress

The contents of the A register 30 may be read out to PINS 7, 8, 9, 10, FIG. 9A, to a suitable display arrangement. The output lines of $A_1$, $A_2$, $A_4$ and $A_8$ appear on lines 510. These outputs are strobed into a zero suppress circuit 511 by a strobe line 512 which is energized once every fifteenth state time by a programmable strobe circuit as will be described, the same source as produced the strobe input 326 to D time generator gate 324. The time of occurrence of the strobe will thus count backwards, like S15, S14, S13 ... S1, S0; this provides zero suppress from MSD first. The $A_1$-$A_8$ bits strobed out are held and allowed into zero suppress upon S0-$\phi_1$ as determined by the output of gate 513 which is activated from a line 514 in the push-pull matrix 310, so all read-outs will start at the same state time. The zero suppress arrangement comprises an eight input NAND gate 515 which receives all of the $A_1$-$A_8$ inputs from lines 516 as four inputs as well as begin and end signals on lines 517 and 518 which are generated in matrix 310. Zero suppress is unconditionally ended by these signals so that the last digit will be displayed even if it is a zero; if the result is all zeros, the last one will be displayed. The lines 517, 518 can be programmed to begin and end at any desired points. The begin line goes through a gate 519 which operates as a latch with the gate 515. DPT indication on line 424 is also an input to gate 515. The first non-zero or decimal point reached sets the 515-519 latch, and the output of the latch is applied to four output NAND gates 520 via line 521, allowing everthing that follows to pass thru. The output NAND gates receive the $A_1$-$A_8$ data on lines 516, and also the line 463 idle set output as well as a blanking signal on line 522, derived from matrix 310, which controls which digits can be displayed, i.g., S1 to S14. The outputs from gates 520 are applied thru suitable non-inverting output buffers to PIN 7 to PIN 10 going to the display.

Commas may be generated by an algorithm and stored in $B_2$, from which they are outputed at PIN 6, upon the occurrence of a proper instruction word.

The Strobe Circuit

A strobe generator circuit 530 of FIG. 9D produces a strobe signal on line 327 and on PIN 16 once every fifteen S times. Depending upon the type of display elements used in the calculator, and how often they should be strobed, the circuit 520 may be programmed to produce a strobe at longer intervals, such as every thirty-one, or sixty-three, or one hundred twenty-seven S times. These are all one less than a multiple of sixteen so that the D times are counted backwards. The strobe circuit 530 comprises an eight stage recirculating shift register 531 of conventional form, along with a matrix 532 programmed in this case to count to fifteen along with an output matrix 533. The arrangement operates as a serial shifting counter that will count to (2N−1); only four stages are used so the embodiment shown counts to fifteen.

The Read Only Memory

Figure 10:
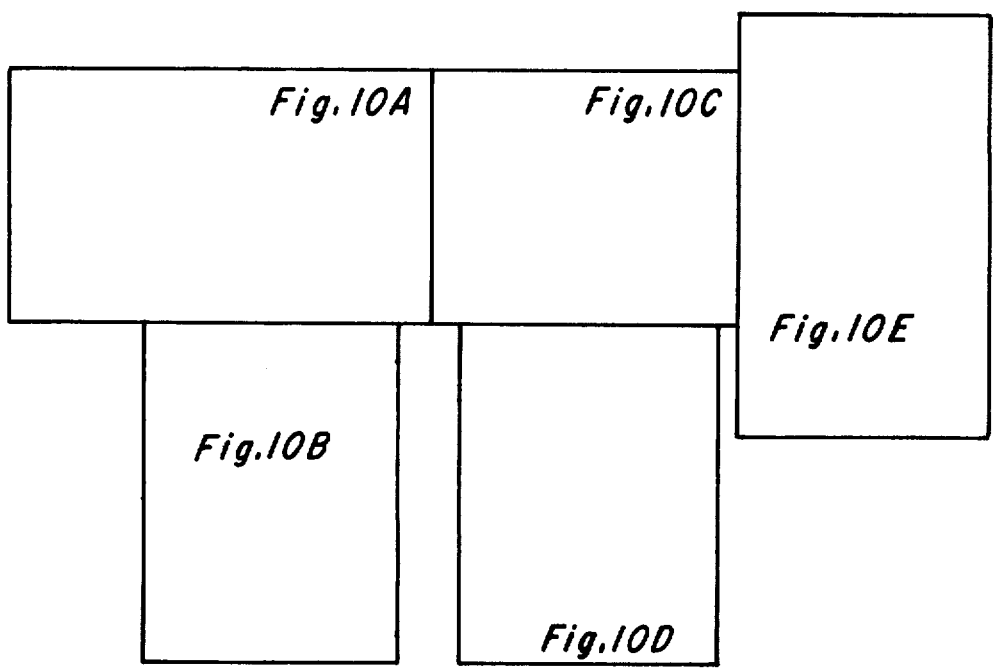
FIG. 10 is a diagram of the layout of FIGS. 10A–10E.
Figure 10A:
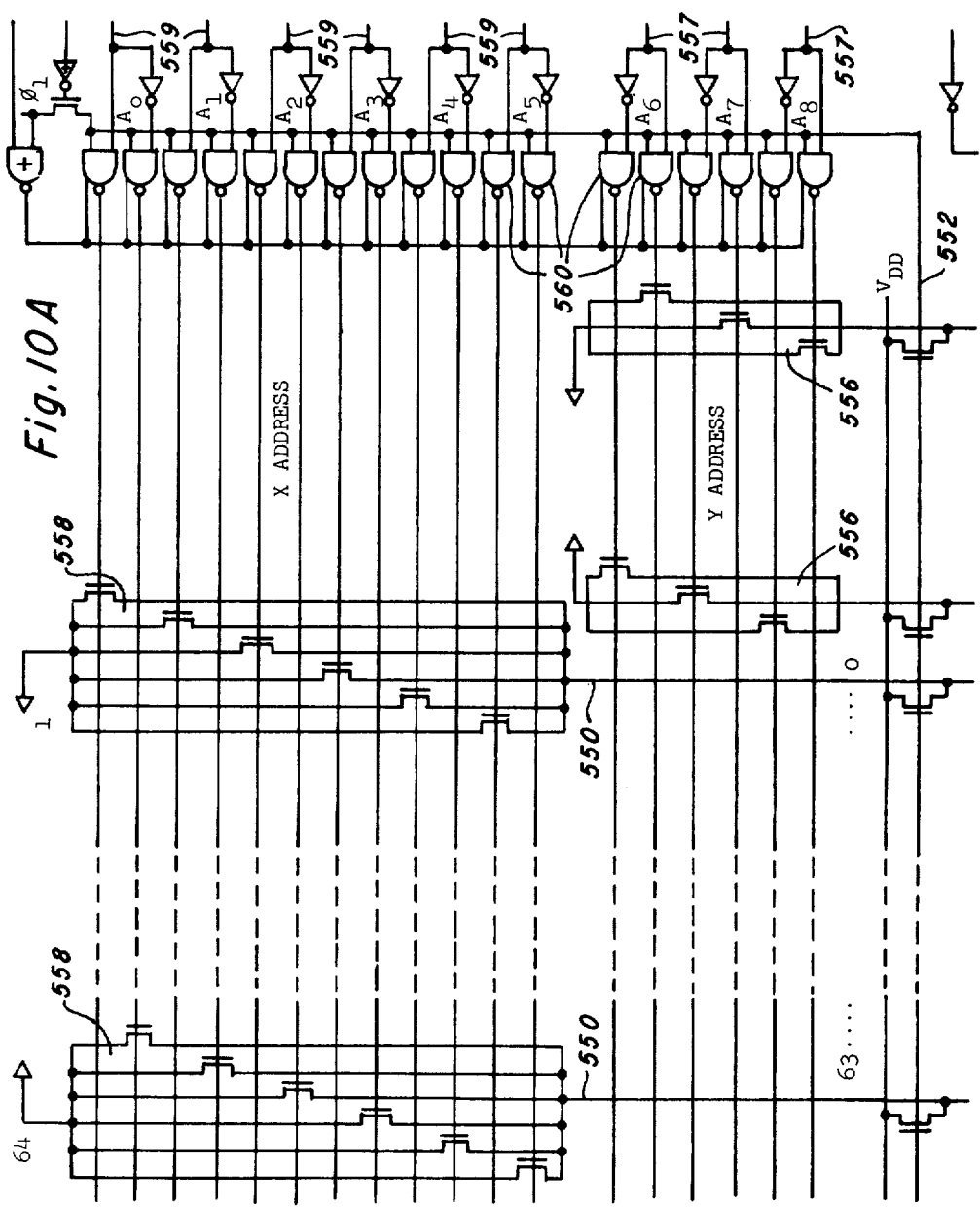
Figure 10B:
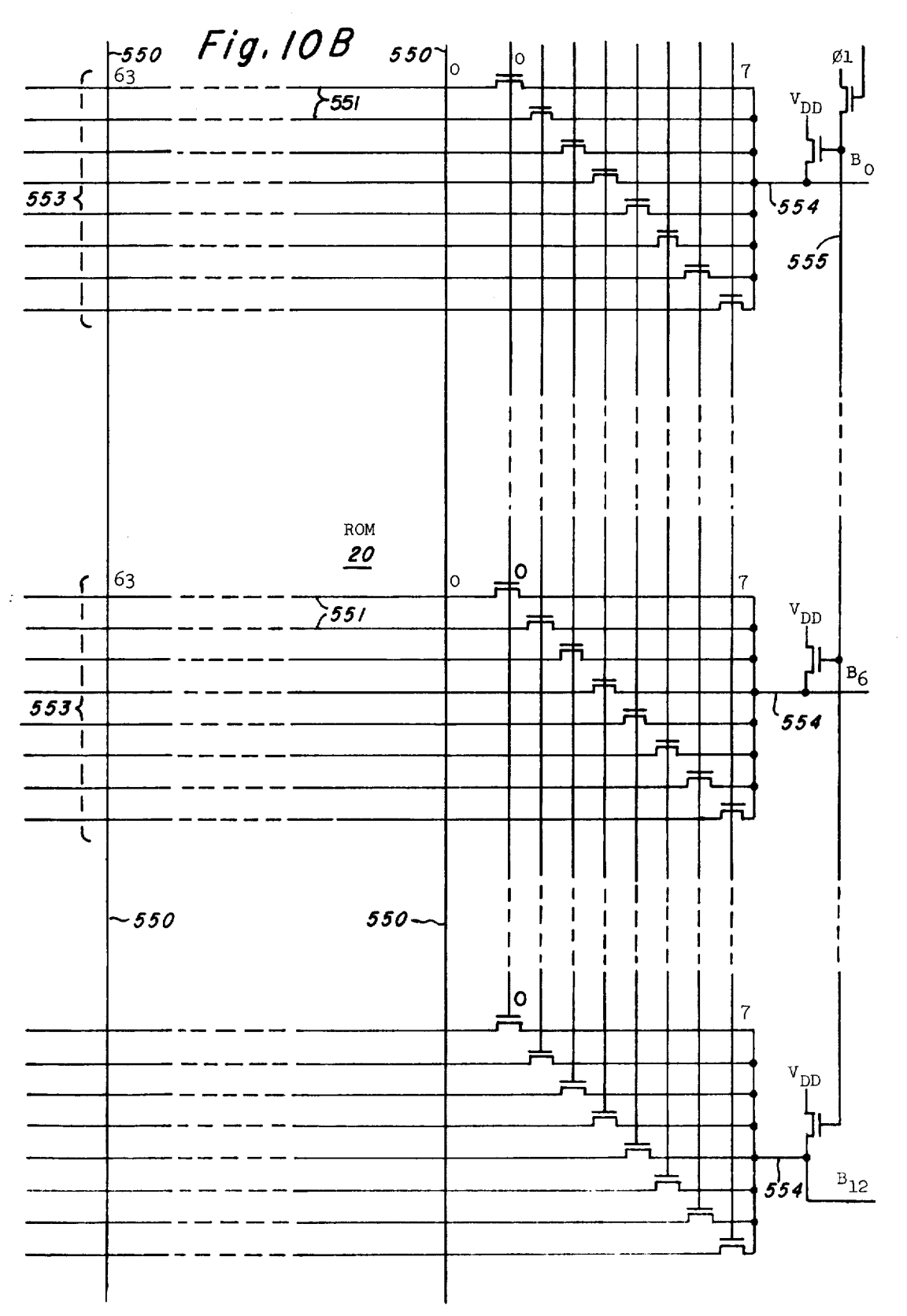
Figure 10C:
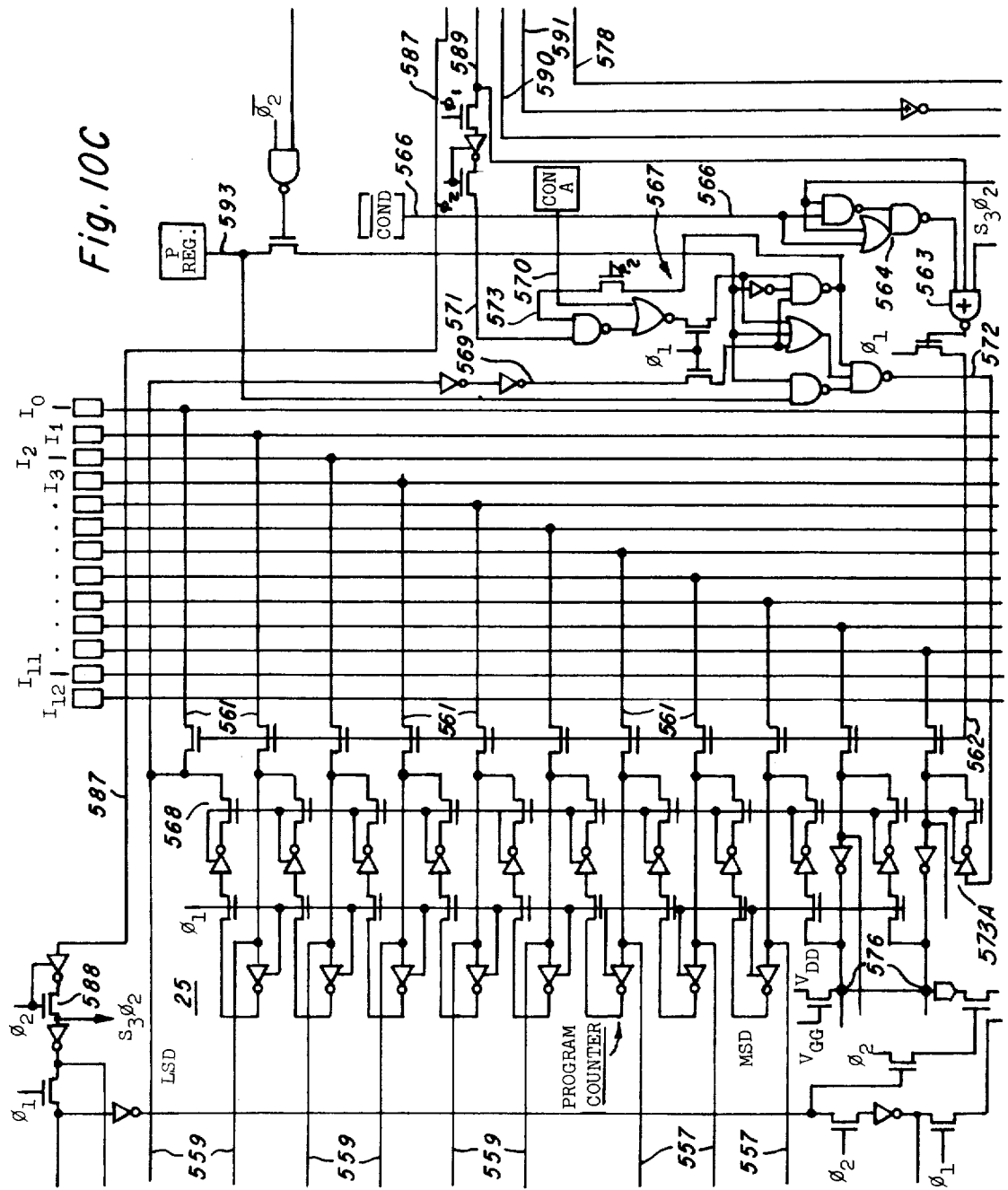
Figure 10D:
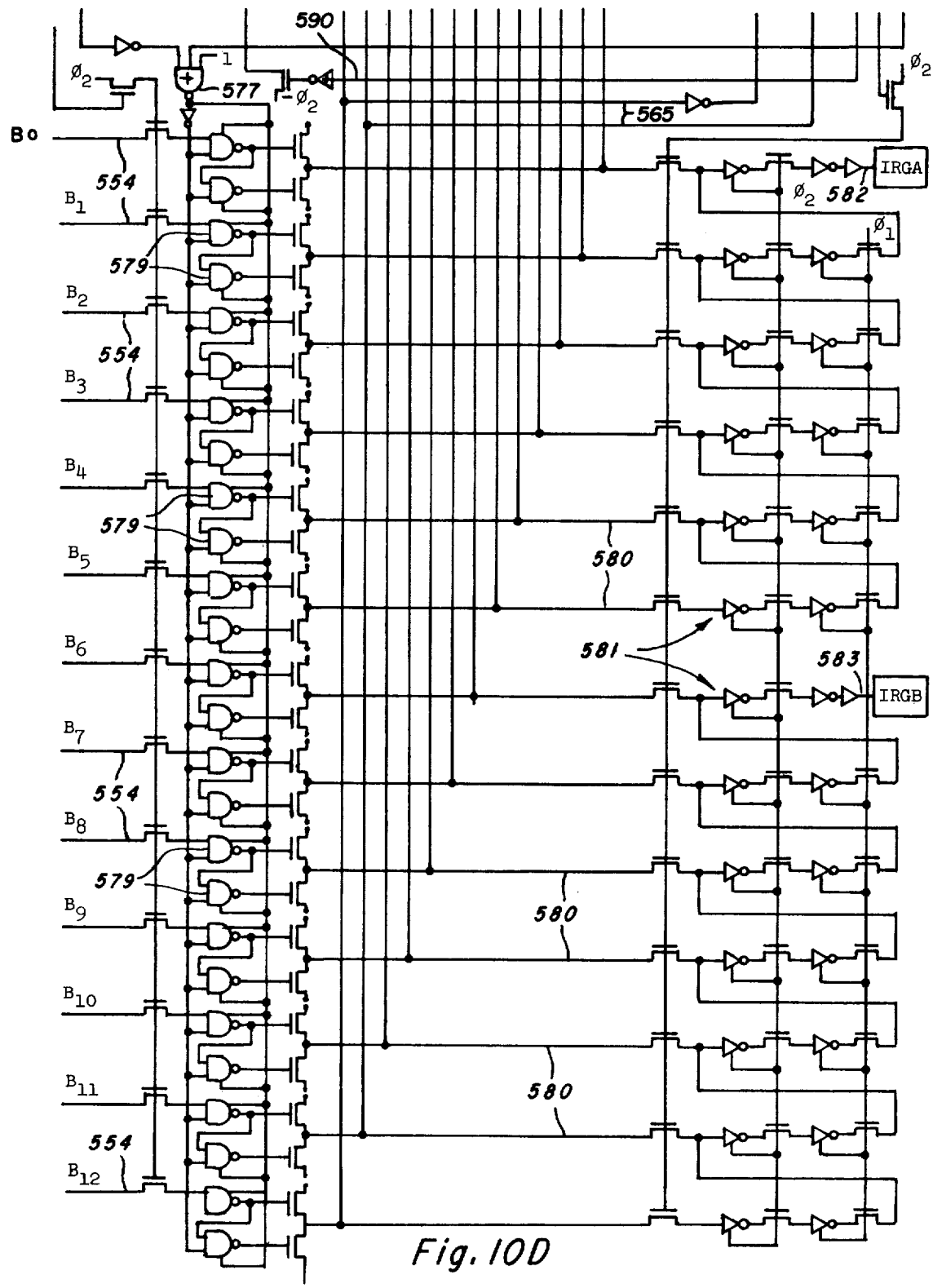

Turning now to the second chip, referred to as the ROM chip, FIG. 10, this device includes a ROM 20 made up of a 64×8×13 or 6656 bit read only memory for storing 512 thirteen bit instruction words. The ROM is programmed as set forth in U.S. Pat. No. 3,541,343, by thinning the oxide where a gate is needed. Sixty-four X address lines 550 are provided (only two are illustrated) and 104 Y lines 551. The X lines 550 are metal stripes and the Y lines 551 are P diffusions. The X lines are precharged to $V_{DD}$ at S4-$\phi_1$ via line 552. The Y lines are arranged in groups 553 of eight to provide thirteen outputs 554 (only three are shown); these output lines are precharged at S5-$\phi_1$ via line 555. Only one of the lines 551 in each group 553 is selected by means of Y address select arrangements 556, of which there are eight (only two are shown). These selector matrixes are driven from three Y address lines 557. The matrixes 556 change three line encoded to eight line unitary. Likewise, selector matrixes 558 select only one of the sixty-four X lines 550 for energization, based on the encoded six bit X address appearing on lines 559. Gates 560 save DC power by gating the X and Y addresses on for only a state time, rather than being on all the time.

The Program Counter

The program counter 25 comprises an eleven stage shift register from which the six address lines 559 and the three Y address lines 557 are outputed in parallel. The program counter operates by either being incremented by one for each instruction cycle, in which case it would cause the instruction words to be read out of the ROM 20 in numerical sequence, or secondly an instruction word can be forced into the counter from input lines 561, as for a branch. The lines 561 are connected into the program counter 25 and address lines 557, 559 via transistors gated by a line 562, which is controlled by gates 563 and 564. These gates receive inputs 565 from bits $I_{11}$ and $I_{12}$ which are used for branch/operation, and condition. An address would be forced in via lines 561 only for branch indicated on $I_{12}$, and if it is a conditional branch this would be indicated on the $I_{11}$ line. The condition is met or not met as indicated on the COND input 566, which is received from COND output of the data chip. So, line 562 goes negative only if a branch is ordered, and, if conditional, when the condition is met. An add-one operation is accomplished by a selector circuit 567, which receives the output of upper stage 568 in the program counter 25 via line 569, and CONA or inhibit increment on line 570. A time signal S3-$\phi_2$ is applied via line 571. The output 572 from this selector circuit is applied to the input of the lower stage 573A of the program counter. The program counter 25 recirculates through the Add-1 selector 567 least significant digit first, and at the time the LSD is going into the selector a one is added at a time controlled by the 8 input 571, if CONA or inhibit increment is not on. If a carry is generated, it is coupled back via line 573 to be added to the next bit. The system is designed to use more than one ROM chip if more than 512 words of stored instructions are needed, so that $I_9$ and $I_{10}$ lines are for chip select. These lines are applied to a logic array 576, the output of which is applied to a select gate 577. The other inputs to this gate are as S1 to S7 timing signal on line 578, and a "1" input which is expanded embodiment would be a CON-B input.

Output from ROM

The output of gate 577 enables a set of output buffers 579 which are in series with the thirteen ROM output lines 554, also labeled $B_0$ to $B_{12}$. The outputs of the buffers 579 are applied via lines 580 to a thirteen bit instruction register 581. This is a two part shift register which shifts the instruction word out via suitable buffers and two lines 582 and 583 going to IRGA and IRGB pins, and thus to the data chip inputs 200 and 201. If more than ROM chip is used, instruction words may be conveyed from one to the other, as for branching, via input/output pins $I_0$ to $I_{12}$ (these are not used in the embodiment described).

Timing Decoder

State times are conveyed from the data chip to the ROM chip via inputs SA,SB,SC,SD, which are applied along with their complements to a timing decoder 585 to regenerate state times S0 to S15. These are applied to a maxtix 586 which generates several time signals. One output 587 provides S3 to the gating generator 588 for input buffers 560 in the X and Y address inputs. An output 589 produces time inputs to the Add-1 selector and the gate 563. An S5 to S15 is generated on a line 590 for producing an eleven bit timing signal for operating the eleven stage shift register of the program counter 25. An S7 output 591 is used to gate the word on lines 580 into the instruction register 581. And, S1–S4 on line 578 is an input to gate 577 as mentioned above. An S4 signal is applied directly from timing decoder output 585 via line 592 to gate the P-REG input 593 into the selector circuit 567. The 7 bit word in the special register 36 of the data chip may be read into the program register 25 via the selector circuit 567; when the P-REG signal is present, Add-1 is ineffective.

The Display Scan

Figure 10E:
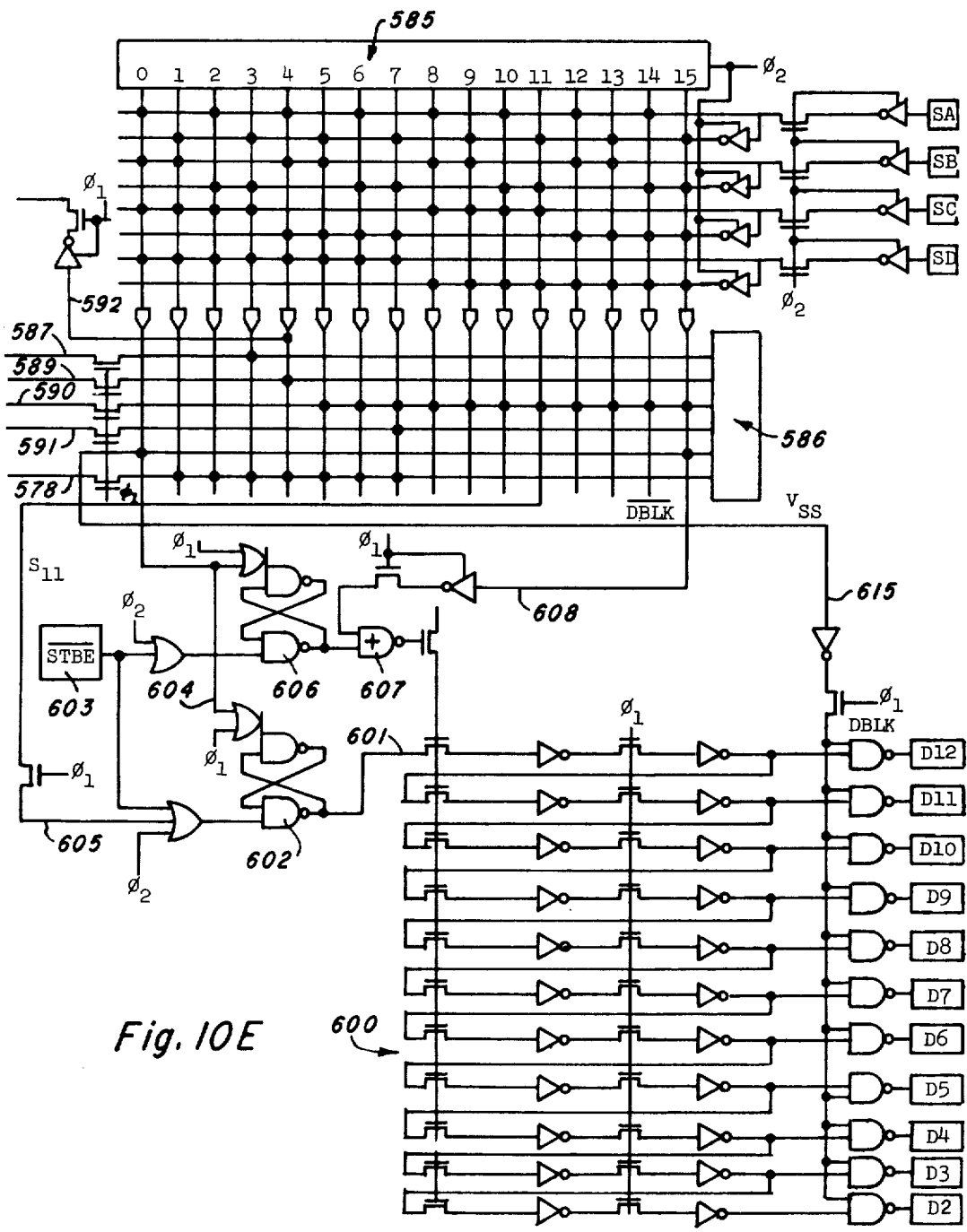

Merely for convenience in placement of pins for the integrated circuit packages, the embodiment of FIGS. 9 and 10 has the display scan split up into two sections, with D2 to D12 on the ROM chip and D13–D15 and D1 on the data chip. In FIG. 10E, the display scan outputs D12 to D2 are generated in an eleven stage shift register 600 which receives an input 601 generated in a latch 602 operated by a strobe input 603, S0 input 604, and S11 input 605. This latch operates with another latch 606 and gate 607 having an S15 input 608, to select a specific D time, e.g., D11, which is then shifted through the register to actuate D12 to D2 in sequence.

The display scan on the data chip, FIGS. 9D and 9J, uses for four stage shift register 610 which is started by a D1 signal on line 329. A latch 464 receives a delayed strobe input from 327 on line 611. S15 is applied to a NAND gate 612 via line 613, and the latched strobe signal is the other input. The register 610 is started by D1 and counts D15, D14, D13, then at this point the display scan of FIG. 10E takes over.

In both FIG. 9J and FIG. 10E, the outputs are blanked by lines 332 and 615 on S0 and S15, so that a gap will exist between D outputs; this is needed for some displays.

The Gate Circuits

Referring now to FIGS. 11A–11R, detailed views of the inverters, NAND and NOR gates, and complex gates used in FIGS. 9 and 10 are shown. FIGS. 11A and 11B are static and dynamic NAND gates, FIG. 11C is a "bootstrap" NAND gate, and FIG. 11D is an open drain, no load NAND. FIG. 11E is a unique bootstrap type gate which is the subject of another patent application. FIGS. 11F, G, H are static, dynamic and open drain NOR gates. FIGS. 11I, J, K, L are inverters of the static, dynamic, bootstrap and open drain types, respectively. FIGS. 11M to 11R are complex gates using only one load.

The Programmable Logic Arrays

Figure 12:
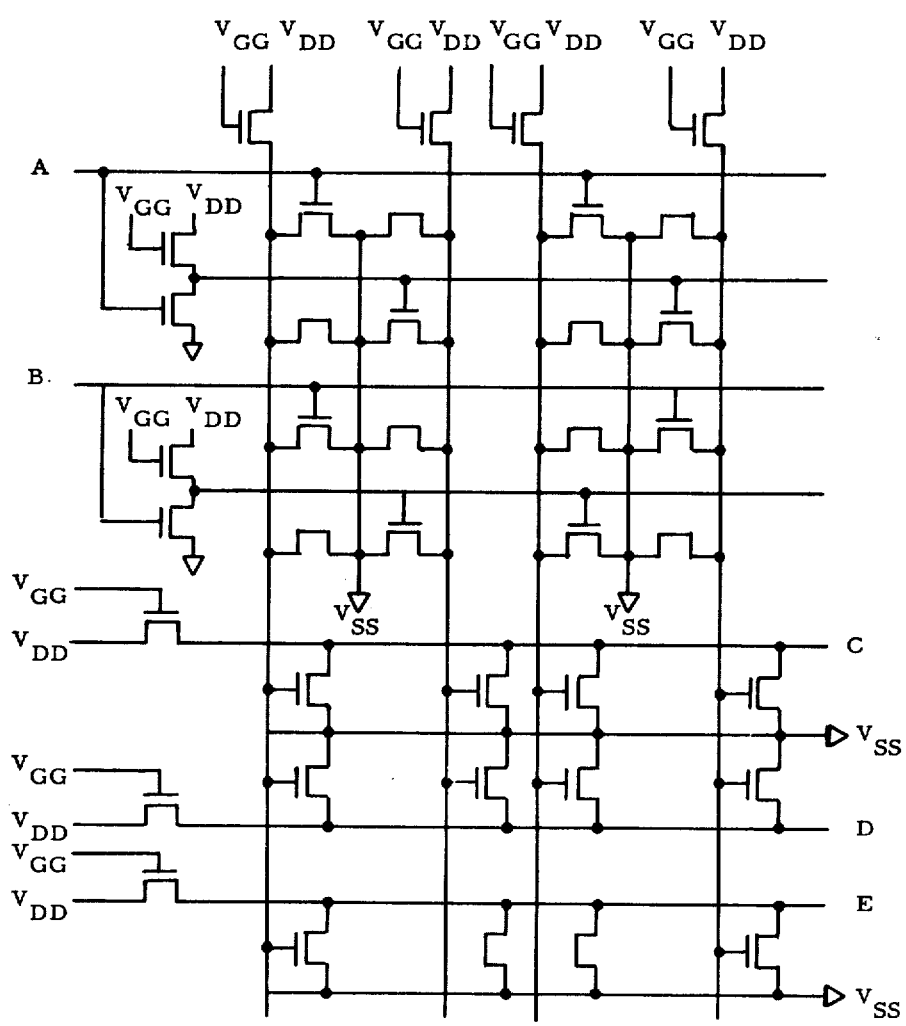
FIG. 12 is a detail view of a programmable logic array as used in the system of FIGS. 9 and 10.
Figure 13A:
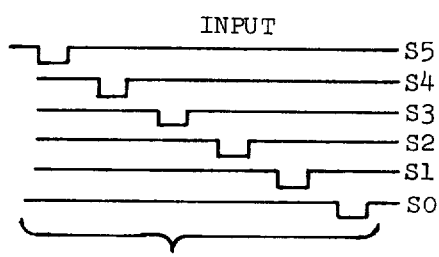
FIGS. 13A–13D show input and output signs, cell layout, and electrical diagram for a specific programmable logic array featured in the invention.
Figure 13B:
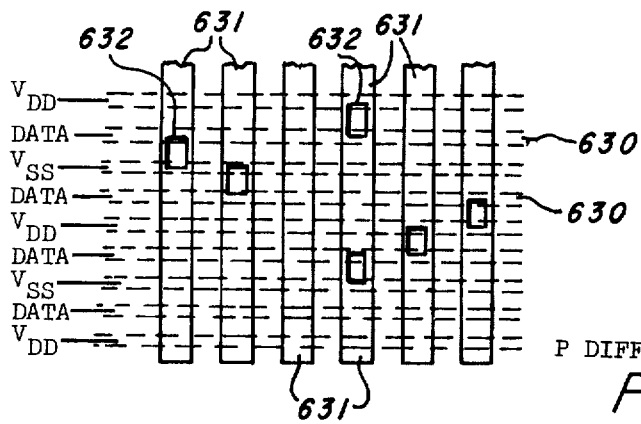
Figure 13C:
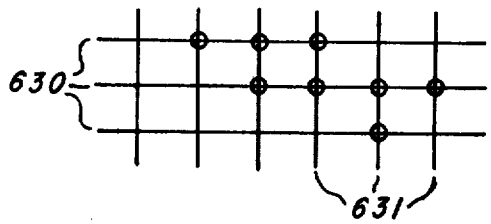
Figure 13D:
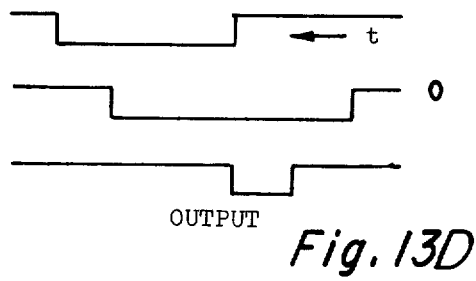

An example of a programmable logic array like those used in the decode matrixes of FIGS. 9 and 10, is shown in FIG. 12. A and B inputs are presented to the first half (decoder) of the PLA in both true and complemented polarities. In this example, four product terms, or decode outputs 620 are presented as inputs to a second (encoder) array. The circuits for the decoder gates and encoder gates are identical shunt gates; that is NAND gates. However, since NAND-NAND logic reduces to AND-OR logic, it is convenient to use sum-of-product notation to describe the PLA circuit implementation where the dependence of a particular product term on a particular input is indicated by a circle at that junction. The circles also correspond physical placement of MOS gates by a programmable gate mask used in fabrication of the MOS embodiment. PLA's are known in the art and need not be detailed herein.

The Push-Pull Matrix

FIG. 13 shows a push-pull matrix such as the matrix 280 or 310 in FIG. 9. This differs from a PLA in that it has no loads and uses no DC power. Output lines 630 for the PLA are P diffusions, represented by dashed lines. Input lines 631 are metallization, represented by solid lines. Gates are provided by thin oxide at locations 632, represented by rectangles. When an input line 631 goes to "0" or minus voltage, and a gate 632 is present, the output line 630 goes to $V_{DD}$ as a channel will be created. This output line will stay at $V_{DD}$ until another gate appears between 630 and $V_{SS}$, when it will go to ground. It is assumed that the lines 631 are being driven one at a time to a "0" voltage, from right to left, just as the matrix 280. The notation used in FIG. 9 for push-pull matrixes is that whenever an output line is to be at a logical "1", there is a circle; this is different from the physical embodiment. FIG. 13A shows the notation used for the embodiment of FIG. 13.

The Program Stored In The ROM

Table VI is a listing of the instruction words stored in the ROM 20 for a standard revision of the calculator of the invention, to produce the operation functions according to the examples of Table V. The first three digit column in Table VI counts the ROM locations (program counter outputs in hexadecimal code from $0.000_{16}(10)$ through $1FE_{16}(511_{10})$. The next eleven digit column reflects the binary code contents of the ROM at each of the locations of the first column; this is the word read into the instruction register including the $I_0$ to $I_{12}$ fields, and is executed by the system. The third column beginning with 0005 is merely line numbers for the printout. The remaining columns give programming labels by which some rountines are known, and instruction mnemonics, and comments relating to the operational meaning of the instructions, as appropriate.

Table VII is another listing of the program instruction words stored in the ROM, listed by ROM address. The words are in hexadecimal. Table VIII is a similar listing in binary instead of hexadecimal. Table IX is a layout of the ROM to produce the instruction words of Tables VI, VII and VIII, wherein each X is a gate in the MOS embodiment of the ROM.

Figure 14A:
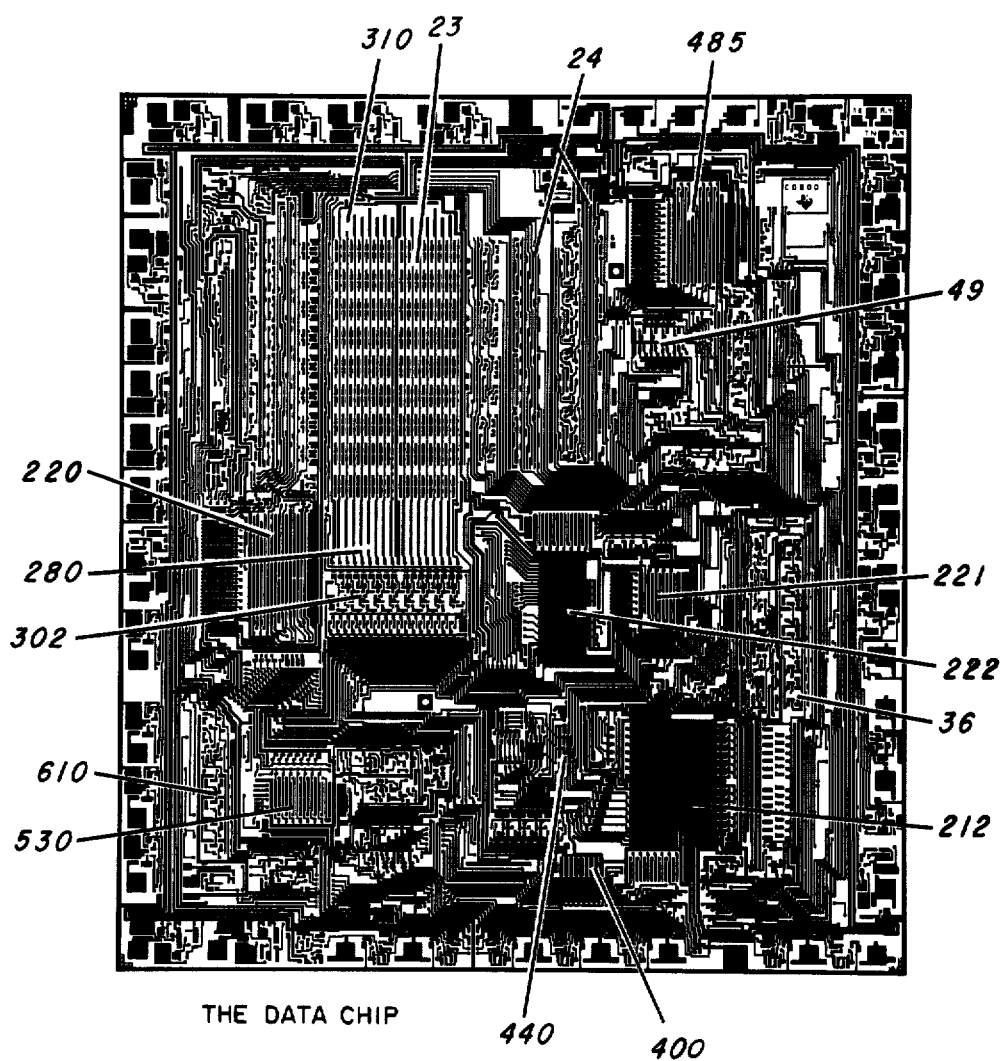
FIGS. 14A–14B show the layout of the semiconductor wafer for the "data chip" and "ROM chip", respectively.
Figure 14B:
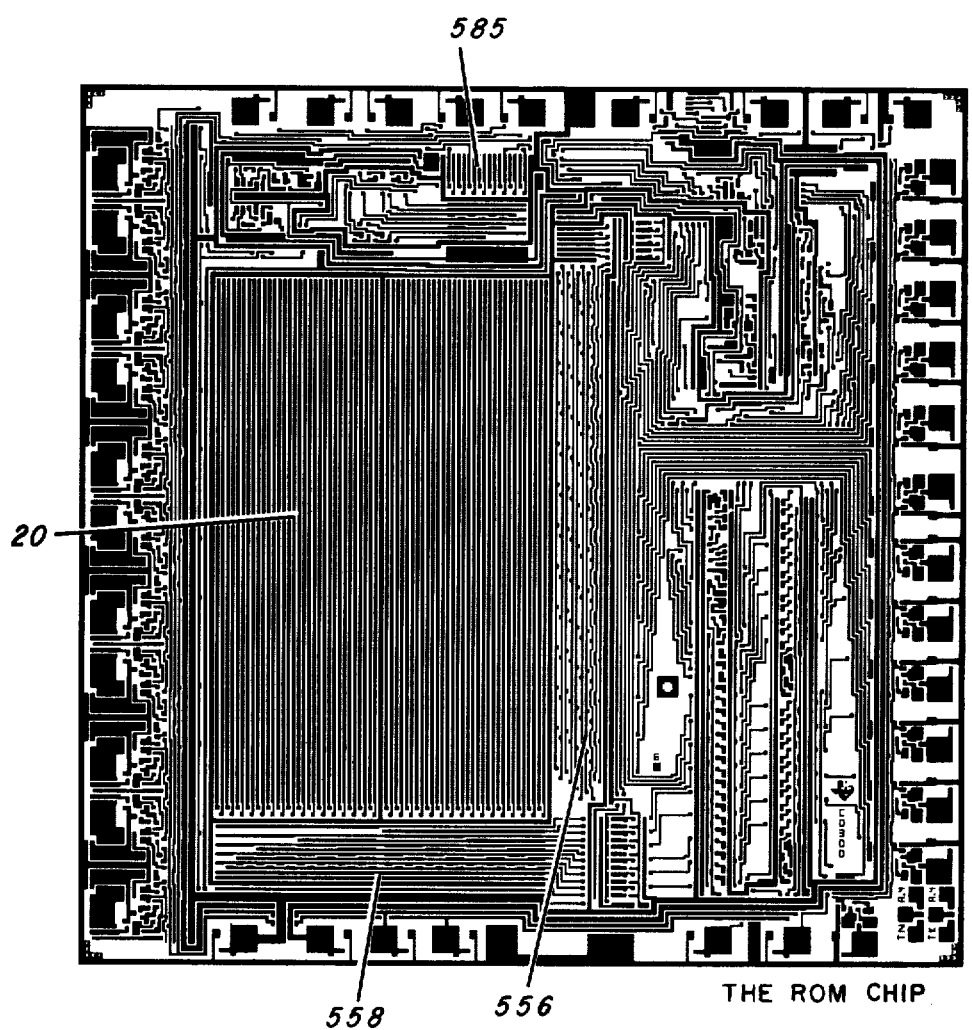

FIGS. 14A and 14B are top views of actual chip layouts for the data chip and ROM chip, respectively, as embodied in MOS/LSI. Various parts of the system, such as the main register 23, the ROM 20, and others, are labeled with the same reference numerals as in FIGS. 2, 3, 9 or 10.

Although the invention has been described with reference to a specific embodiment, various modifications of this embodiment as well as other embodiments of the invention will become apparent to persons skilled in the art. It is therefore contemplated that the appended claims will be construed in a limiting sense and will cover any such modifications or embodiments as fall within the true scope of the invention.

TABLE I

| M field | Mask | Constant N at state time |
|---|---|---|
| M0 | S0-S15 | none |
| M1 | S1 | 1 at S1 |
| M2 | S1 | none |
| M3 | S1 | 11 at S1 |
| M4 | S2-S14 | none |
| M5 | S2-S14 | 1 at S2 (LSD) |
| M6 | S2-S14 | 1 at S13 (MSD) |
| M7 | S2-S14 | 5 at S2 (LSD) |
| M8 | S0 | 1 at S0 |
| M9 | S0 | 11 at S0 |
| M10 | S0 | none |
| M11 | S2 | 1 at S2 (LSD) |
| M12 | S2-S14 | 1 at S14 (OV) |

TABLE II

| R | X input | Y Input | Operation | |
|---|---|---|---|---|
| R0 | 0 | 0 | no operation | |
| R1-R3 | | not used | | |
| R4 | A | N | A ± N | |
| R5 | 0 | B,N | ±(B + N) | |
| R6 | C | N | C ± N | |
| R7 | 0 | D,N | (D + N) | $\overline{SUB}$-add |
| R8 | A | B | A ± B | |
| R9 | A | D | A ± D | |
| R10 | C | B | C ± B | SUB-subtract |
| R11 | C | D | C ± D | |
| R12 | | | Shift A | |
| R13 | | | Shift B | $\overline{SUB}$-shift left |
| R14 | | | Shift C | |
| R15 | | | Shift D | SUB-shift right |

NOTE:
±denotes logical OR
$\overline{SUB}$ means SUB = 0
SUB means SUB = 1

TABLE III

| S | Operation |
|---|---|
| S0 | A↔B & Σ→C |
| S1 | T sent to I/O pins* |
| S2 | Exchange registers A and B |
| S3 | Exchange registers C and D |

TABLE III-continued

| S | Operation |
|---|---|
| S4 | ALU output S stored in register C |
| S5 | ALU output S stored in register D |
| S6 | ALU output S stored in register A |
| S7 | ALU output S stored in register B |

TABLE IV (1) Clear All $\boxed{C}$ :

clears the Display and the Constant registers and the Entry and Result Overflow signals. It has no effect on Memory Register.

(2) Clear Memory $\boxed{CM}$ :

clears the Memory Register and Result Overflow indicator.

(3) Clear Entry $\boxed{CE}$ :

clears the Display Register of a number just entered. If the number entered exceeded machine capacity, the Entry Overflow signal is cleared. If the Display Register contains a calculation result and Result Overflow, only Result Overflow is reset.

(4) Clear Indicator $\boxed{CI}$ :

clears display and any overflow lamp. $\boxed{CI}$ is effective on both number entry and calculation result.

(5) Right Shift $\boxed{RS}$ :

shifts the Display Register to right 1 digit, causing the Display Register to lose the least significant digit. If the Overflow indicator is on, it is now turned off. The RS key does not terminate a number entered. Therefore 12.34 $\boxed{RS}$ 56 is interpreted as 12.356 in the Display Register.

NOTE: All function keys except the above five will be locked in the case of Result Overflow.

(6) Change Sign $\boxed{CS}$ :

changes the sign of Display Register, from '+' to '−' and vice versa. The display may be a number entered or a previous result. CS key does not terminate a number entered. Therefore, 12.34 $\boxed{CS}$ 56 is interpreted as −12.3456 in the Display Register.

(7) Recall Memory $\boxed{RM}$ :

loads the content of the Memory into the Display Register. The previous content of Display ister is NOT saved.

(8) Reverse Key $\boxed{RV}$ :

exchanges the contents of the Display Register and the Constant Register; the number is displayed in floating mode, i.e., may lose trailing zeros.

(9) Percentage $\boxed{\%}$ :

moves the decimal point of the displayed number two places to the left (i.e., it divides the displayed number by 100). Digits that can not be displayed will be truncated (i.e., digits less significant than the first 12 digits). $\boxed{\%}$ does not terminate a number entered. Therefore, 12.34 $\boxed{\%}$ 56 is interpreted as 0.123456 on Display Register.

(10) Multiply $\boxed{\times}$ :

stores a multiply command for later use and executes a possible previous multiply or divide command. Previous add or subtract commands are not executed.

(11) Divide $\boxed{\div}$ :

operates the same as the multiply key except that a divide command is stored.

NOTE: Only the last $\boxed{\times}$ or $\boxed{\div}$ becomes effective if successive $\boxed{\times}$ and $\boxed{\div}$ are entered; i.e., $a \times \div \times \div \div \times \times \div b$ is interpreted as $a \div b$.

(12) Plus Equal $\boxed{+=}$ :

terminates a number entry and stores an add command. Any preceding arithmetic command is executed.

TABLE IV-continued

In the case of nonconstant operation without a prior number entry, $\boxed{+=}$ acts as no operation.

In the case of constant operation OR a prior number entry with a previous multiply (or divide), $\boxed{+=}$ acts as a constant multiplication (or division).

(13) Memory Plus Equal $\boxed{M+=}$:

performs a $\boxed{+=}$ operation and accumulates results to memory. Which function is performed first depends on the kind of key-in entries.

a.
        In the case of previous multiplication (or division), $\boxed{+=}$ function is done first and the result product (or quotient) is then accumulated to Memory Register.
    b. In the case of previous addition (or subtraction) the memory is accumulated algebrically first, then followed by addition (or subtraction) operation:
        i.e., a × b M += the display shows ab and the product ab is accumulated to memory
            a + E b M += the display shows a + b but only b is accumulated to memory

(14) Minus Equal $\boxed{-=}$:

behaves like the $\boxed{+=}$ operation except that the sign of the Display Register is changed with each $\boxed{-=}$ command

(15) Memory Minus Equal $\boxed{M-=}$:

performs $\boxed{-=}$ operation and memory accumulation.

The $\boxed{M-=}$ behaves like the $\boxed{M+=}$ except that a $\boxed{-=}$ function is performed instead of a $\boxed{+=}$ function.

(16) Subtotal $\boxed{S}$:

recalls the content of the Memory Register to display and retains memory. It saves previous display if previous display was NOT a number entry. Previous display is not saved if it was a number entry.

(17) Total $\boxed{T}$:

same as that of $\boxed{S}$ key; and in addition to it, Memory Register is cleared.

(18) Add-On, Discount $\boxed{A/D}$ will allow taking a percentage from a number in the calculator and indicate the resulting percentage on the display. A += (or -=) can be keyed-in to obtain the sum of (or difference of) the original and the percentage. A/D key operates in both constant and nonconstant mode.

(19) Memory Plus $\boxed{M+}$:

accumulates whatever is in display to Memory Register without performing a previous operation.

Successive use of $\boxed{M+}$ will accumulate to memory successively. Therefore, a × b += M+M+M+ will accumulate 3ab to Memory Register. However, a × b M+M+M+ accumulates 3b to Memory Register and multiply command is still is effect.

NOTE: $\boxed{RM}$, $\boxed{S}$, $\boxed{T}$ keys recall content of Memory Register to display the way it is in the Memory - i.e., not adjusting to Fix-Point mode or Floating mode.

(20) Memory Minus $\boxed{M-}$:

same as that of M+ key except that it subtracts the display from memory without changing the sign of display.

NOTE: The difference between M±= and M± is that M± do not perform an 'EQUALITY' function. Therefore, a × b M+= accumulates ab to Memory and a × b M+ accumulates b to Memory.

TABLE IV-continued

NOTE:

[M+], [M−], [RV] keys involve data transfers or arithmetic operations and the display will be in Floating mode.

Example:

|  |  | Display | Memory |
|---|---|---|---|
|  | 123.040 | 123.040 | 33.14 |
| D4 | M+ | 123.04 | 156.1800 |

Memory accumulation is always in Fixed-Point mode while M+, M− always displays original number in floating mode, which loses insignificant zeros.

CAUTION:

|  | Display | Memory |
|---|---|---|
| 12.34 | 12.34 | m |
| M+ | 12.34 | m + 12.34 |
| 56 | 12.3456 | m + 12.34 |

Since M+ does not terminate number entries.

NOTE:

[RV], [RM], [S], [T], [A/D] will be treated as a number entry but is NOT a number entry.

Function keys requiring a number entry will be effective.

Example:

|  | Display | Memory |
|---|---|---|
| c | c | m |
| × | c | m |
|  | m | m |
| [RM] |  |  |
| += |  | m |
|  | [mc] |  |

Example:

|  | Display | Memory |
|---|---|---|
| a | a | m |
| × | a | m |
| b | b | m |
| ÷ | ab | m |
| S | m | m |
| × | ab/m | m |
| c | c | m |
| += | abc/m | m |

NOTE: while M+, M− do not terminate a number entry, RM, S, T, CM terminate a number entry.

TABLE V

OPERATION EXAMPLES

The following operation examples are presented by key and display with accompanying remarks and explanation.

EXAMPLE NO. 1: Number Entry and its Limitations

| KEY | DISPLAY | COMMENT |
|---|---|---|
| C | 0 |  |
| 12.34.56.78 | 12.345678 | Only the first decimal point is protected. |
| CS | −12.345678 |  |
| 92 | −12.34567892 | Change sign does not terminate the number entry. |
| −= | 12.34567892 | −= key changes the sign and terminates the number entry. |
| 145.67 | 145.67 |  |
| % | 1.4567 |  |
| 89 | 1.456789 | % key does not terminate a number entry. |
| RS | 1.45678 | The least significant number is shifted out. |
| 92345 | 1.4567892345 | RS key does not terminate a number entry. |
| 6401 | 1.45678923456 E | An Entry overflow indicator truncates entry digits less significant than the first 12 digits. |
| % | 0.01456789234 E | Displaying not more than 11 decimal places. |
| % | 0.00014567892 E |  |
| % | 0.00000145678 E |  |
| RS | 0.0000014567 |  |
| RS | 0.000001456 | The number entry is not terminated since the last −= key. |
| CE | 0 | CE clears a number entry and entry overflow indicator. |

EXAMPLE NO. 2: K Switch

The following cases show six different uses of the constant mode switch K. K switch is on.

|  | KEY | DISPLAY REGISTER | CONSTANT REGISTER | OPERATOR | COMMENT |
|---|---|---|---|---|---|
| Case 1 | a | a | — | — |  |
|  | × | a | a | × |  |
|  | += | [a²] | [a] | [×] | Power multiplication |

TABLE V-continued
OPERATION EXAMPLES

| | | | | | |
|---|---|---|---|---|---|
| | += | [a³] | a | × | |
| | += | [a⁴] | a | × | |
| Case 2 | C | 0 | 0 | — | |
| | a | a | 0 | — | |
| | × | a | a | × | Continuous type of constant, multiplication with constant, multiplicand |
| | b | b | a | × | |
| | += | [ab] | [a] | [×] | |
| | += | [a²b] | a | × | |
| | += | [a³b] | a | × | |
| | C | 0 | 0 | — | |
| | a | a | 0 | — | |
| | × | a | [a] | [×] | |
| | / | a | a | [÷] | Only last operator is effective. |
| | b | b | a | ÷ | Continuous type of constant, division with constant divisor. |
| | += | [a/b] | [b] | ÷ | |
| | += | [a/b²] | b | ÷ | |
| | += | [a/b³] | b | ÷ | |
| Case 5 | C | 0 | 0 | — | |
| | a | a | 0 | — | |
| | × | a | a | × | |
| | b | b | a | × | |
| | += | [ab] | [a] | [×] | |
| | c | c | a | × | |
| | += | [ac] | a | × | |
| | ÷ | ac | a | ÷ | Updating the operator and the constant anywhere it occurs. |
| | d | d | ac | ÷ | |
| | += | [ac/d] | [d] | [÷] | |
| | e | e | d | ÷ | |
| | += | [e/d] | d | ÷ | |
| Case 6 | C | 0 | 0 | — | |
| | a | a | 0 | — | |
| | × | a | a | × | |
| | b | b | a | × | |
| | += | [ab] | [a] | [×] | |
| | c | c | a | × | Changing the operator and the constant as if working on a new problem. No clear key is required. |
| | ÷ | c | c | ÷ | |
| | d | d | c | ÷ | |
| | += | [c/d] | [d] | [÷] | |
| Case 7 | a | a | — | — | Any "complex power" multiplication of two numbers can be accomplished by using ×, |
| | × | a | a | [×] | |

TABLE V-continued
OPERATION EXAMPLES

| Case | | | | | | Notes |
|---|---|---|---|---|---|---|
| | b | b | a | × | | $\div, +=, -=$ keys while Constant mode on. |
| | $+=$ | [ab] | [a] | × | | |
| | $+=$ | [$a^2b$] | a | × | | |
| | × | $a^2b$ | $a^2b$ | × | | |
| | $+=$ | [$(a^2b)^2$] | [$a^2b$] | × | | |
| | $+=$ | [$(a^2b)^3$] | $a^2b$ | × | | |
| | $\div$ | $(a^2b)^3$ | $(a^2b)^3$ | [$\div$] | | |
| | $+=$ | 1 | [$(a^2b)^3$] | + | | |
| | $+=$ | [$[(a^2b)^3]^{-1}$] | $(a^2b)^3$ | + | | |
| | $+=$ | [$[(a^2b)^3]^{-2}$] | $(a^2b)^3$ | + | | |
| Case 3 | a | a | 0 | — | | Discrete type of constant multiplication |
| | × | a | a | × | | |
| | b | b | a | × | | |
| | $+=$ | [ab] | [a] | [×] | | |
| | c | c | a | × | | |
| | $+=$ | [ac] | a | × | | |
| | d | d | a | × | | |
| | $+=$ | [ad] | a | × | | |
| | C | 0 | 0 | — | | |
| | a | a | 0 | — | | |
| | $\div$ | a | a | $\div$ | | Discrete type of constant division. |
| | b | b | a | $\div$ | | |
| | $+=$ | [a/b] | [b] | [$\div$] | | |
| | c | c | b | $\div$ | | |
| | $+=$ | [c/b] | b | $\div$ | | |
| | d | d | b | $\div$ | | |
| | $+=$ | [d/b] | b | $\div$ | | |
| Case 4 | C | 0 | 0 | — | | |
| | a | a | 0 | — | | |
| | × | a | a | [×] | | |
| | b | b | a | × | | Updating the operator and the constant as the calculation goes along, in a chain. |
| | $\div$ | [ab] | [a] | [/] | | |
| | c | c | ab | / | | |
| | × | [ab/c] | [c] | [×] | | |
| | d | d | ab/c | × | | |
| | $+=$ | [abd/c] | [ab/c] | × | | |
| | e | e | ab/c | × | | |
| | $+=$ | [abe/c] | ab/c | × | | |
| | C | 0 | 0 | — | | |

EXAMPLE NO. 3: A/D Key

This example shows four different uses of the A/D key (one-touch, add-on, discount Key)

TABLE V-continued
OPERATION EXAMPLES

| | KEY | DISPLAY | COMMENT |
|---|---|---|---|
| Case 1 | C | 0 | |
| K off and in | a | a | The principal. |
| floating mode | × | a | |
| | b | b | |
| | A/D | ab/100 | Compute b % of a. |
| | −= | a − ab/100 | Result after taking out b% from principal. |
| | × | a − ab/100 | |
| | c | c | |
| | A/D | (a − ab/100) · C/100 | Compute c % of the result |
| | += | (a − ab/100) (1 + C/100) | Add c % of the result to the result. |
| in real numbers | C | 0 | |
| | 250.25 | 250.25 | Original price. |
| | × | 250.25 | |
| | 4.9 | 4.9 | 4.9% discount |
| | A/D | 12.26225 | The discount |
| | −= | 237.98775 | Sale price after discount. |
| | × | 237.98775 | |
| | 7.2 | 7.2 | 7.2% state sales tax |
| | A/D | 17.135118 | The state sales tax |
| | += | 255.122868 | Final price |
| Case 2 | | | |
| K on | C | 0 | |
| | a | a | |
| | × | c | |
| | b | b | |
| | A/D | ab/100 | Compute a % of b or b % of a. |
| | c | c | |
| | A/D | ac/100 | c % of a or a % of c. |
| | d | d | |
| | A/D | ad/100 | d % of a or a % of d. |

NOTE: There are 2 interpretations in case 2.
1. Taking b, c, d, percents of 'a' which is the principal, b, c, d, being 3 different principals, and 'a' is a fixed interest rate.
2. Taking 'a' percent of b, c, d, which are 3 different principals, and 'a' is a fixed interest rate.

| | KEY | DISPLAY | COMMENT |
|---|---|---|---|
| Case 3 | | | |
| K on | C | 0 | |
| | a | a | The principal. |
| | × | a | |
| | b | b | |
| | A/D | ab/100 | The interest paid (b %) |
| | += | a (1 + b/100) | The compound. |
| | c | c | |
| | A/D | ac/100 | (c %) |
| | += | a (1 + c/100) | |
| | d | d | |

TABLE V-continued
OPERATION EXAMPLES

|  | A/D |  | (d %) |
|---|---|---|---|
|  |  | $\boxed{ad/100}$ |  |
|  | += |  |  |
|  |  | $\boxed{a(1 + d/100)}$ |  |
| Case 4 |  |  |  |
| Taking a % of a % | a |  | Principal for the year. |
|  |  | $\boxed{a}$ |  |
| as in the | × | a |  |
| case of | b | b |  |
| profit sharing | A/D |  | b% of the principal "a" |
|  |  | $\boxed{ab/100}$ |  |
| K off | × | ab/100 |  |
|  | c | c |  |
|  | A/D |  | c% of b% |
|  |  | $\boxed{(ab/100)(c/100)}$ |  |

EXAMPLE NO. 4: Result Overflow
Lock out all keyboard entries except C, CE, CM, RS keys

| | KEY | DISPLAY | COMMENT |
|---|---|---|---|
| K on | C | 0 | |
| Round down | 200000000002 | 200000000002 | |
|  | × | 200000000002 | |
|  | 9 | 9 | |
|  | += | 1.80000000001 # | Result overflow. Result should be 1800000000018. #indicates |
|  |  |  | (1) Result overflow |
|  |  |  | (2) Exponent × $10^{12}$ |
|  |  |  | (3) Displaying only 12 digits and lowing least significant digits without rounding. |
|  | 5 | 1.80000000001 # | all keys except C, CE, CM, RS are locked (i.e., no effect). |
|  | += | 1.80000000001 # |  |
|  | RS | 1.8000000000 | RS key shifts number to right by 1 and turns off result overflow indicator. |
|  | 5 | 5 |  |
|  | += | 1.00000000001 # | Result overflow again. |
|  | CE | 1.00000000001 | CE removes Result overflow indicator but does not clear the display as this is not a number entry. |
|  | 6 | 6 |  |
|  | += | 1.20000000001 # |  |
|  | CM | 1.20000000001 | CM clears the Memory register and removes result overflow indicator. |
| Round off | 0.0919 | 0.0919 |  |
|  | += | 18380000000.1 | The original result is 18380000000.1838 display shows only 12 digits. This is NOT a result overflow. |
|  | C | 0 | Floating mode, no rounding |

EXAMPLE NO. 5: Addition, subtraction, multiplication and division

| | KEY | DISPLAY | COMMENT |
|---|---|---|---|
| K off | C | 0 |  |
| D2 | 21122112 | 21122112 | −= key changes the sign of display. |
| Round down | −= | −21122112.00 | 'Equality' function provides fixed-point mode. |
|  | 0.3 | 0.3 |  |
|  | += | −21122111.70 | Subtraction is the result of an addition to a negative number. This is characteristic of the +=, −= machine. |
|  | 11.4 | 11.4 |  |
|  | −= | −21122123.10 | −= key does not always perform a subtraction; In this case addition of 2 negative numbers. |
|  | += | −21122123.10 | Successive += entries without Number entry have no effect. |
|  | += | −21122123.10 |  |
|  | × | −21122123.10 |  |
|  | 0.002 | 0.002 |  |
|  | ÷ | −42244.2462 | Intermediate result, i.e., multiplication and division, are in floating mode. |
|  | 1 | 1 |  |
|  | −= | 42244.24 |  |
|  | 2 | 2 |  |
|  | × | 2 | × and ÷ do not recognize previous add or subtract |
|  | 1.2 | 1.2 |  |
|  | += | 2.40 |  |
|  | CS | −2.40 | Change sign changes the sign of the Display |

TABLE V-continued
OPERATION EXAMPLES

|   |   |   |
|---|---|---|
| 4 | 4 | Register. If it is a result of an operation CS is NOT part of a number entry. |
| × |   |   |
| 5 | 4 |   |
| += | 5 |   |
| C | 20.00 |   |
| CS | 0 |   |
|   | −0 | If it is a number entry, CS is part of the number entry. |
| 456.2 | −456.2 |   |
| C | 0 |   |
| 70.42 | 70.42 |   |
| ÷ | 70.42 |   |
| 3 | 3 |   |
| × | 23.4733333333 |   |
| 3 | 3 |   |
| += | 70.41 | This indicates the reason for having intermediate result in floating mode. |

EXAMPLE NO. 6: Arithmetic Series and Geometric Series

This example shows the power of constant-mode and summation-mode switches. Summation switch accumulates up-to-date the sum of N terms into the memory while the constant switch displays the $N^{th}$ term.

| | KEY | DISPLAY | CONSTANT | MEMORY | COMMENT |
|---|---|---|---|---|---|
| Case 1: | C | 0 | 0 | — | |
| K on | CM | 0 | 0 | 0 | CM clears the memory |
| Σ on | 2 | 2 | 0 | 0 | |
| floating | × | 2 | 2 | 0 | constant multiplicand |
| | += | 4 | 2 | 4 | $2^2$ |
| | += | 8 | 2 | 12 | $2^2 + 2^3$ |
| | += | 16 | 2 | 28 | $2^2 + 2^3 + 2^4$ |
| | . | . | . | . | |
| | . | . | . | . | |
| | . | . | . | . | |
| Case 2: GS | C | 0 | 0 | — | |
| K on or off | CM | 0 | 0 | 0 | |
| Σ on | 2 | 2 | 0 | 0 | |
| | × | 2 | 2 | 0 | no constant as K is up |
| | += | 4 | 2 | 4 | $2^2$ |
| | × | 4 | 4 | 4 | |
| | += | 16 | 4 | 20 | $2^2 + 2^4$ |
| | × | 16 | 16 | 20 | |
| | += | 256 | 16 | 276 | $2^2 + 2^4 + 2^8$ |
| | × | 256 | 256 | 276 | |
| | += | 65536 | 256 | 65812 | $2^2 + 2^4 + 2^8 + 2^{16}$ |
| | × | 65536 | 65536 | 65812 | |
| | += | 4294967296 | 65536 | 4295033108 | $2^2 + 2^4 + 2^8 + 2^{16} + 2^{32}$ |
| | × | 4294967296 | 4294967296 | 4295033108 | |
| | += # | 18446744.0737 | 4294967296 | 4295033108 | Result overflow, memory protected. |

EXAMPLE NO. 7: This shows the use of Memory-related keys

| | KEY | DISPLAY | MEMORY | COMMENTS |
|---|---|---|---|---|
| Case 1: | | | | |
| M+ and M− | C | 0 | — | |
| Keys | CM | 0 | 0 | CM key zeros the Memory. |
| | 9 | 9 | 0 | |
| | M+ | 9 | 9 | M+ key accumulates the display to Memory (A number entry). |

TABLE V-continued
OPERATION EXAMPLES

| | | | | |
|---|---|---|---|---|
| | M+ | 9 | [18] | Successive use of M+ key causes successive accumulation of display to memory. |
| | M+ | 9 | [27] | |
| | M− | | [9] [18] | M− key changes the sign of display, then accumulates the display to Memory; i.e., M− adds the compliment of display to Memory (consistency of the +=, −= machine) |
| | M− | | [9] [9] | |
| | CM | 9 | 0 | |
| | C | 0 | 0 | |
| | 2.305 | 2.305 | 0 | |
| | × | 2.305 | 0 | |
| | 4 | 4 | 0 | |
| | += | [9.22] | 0 | |
| | M+ | 9.22 | [9.22] | M+ key accumulates the display to Memory (a result). |
| | 2.24 | 2.24 | 9.22 | |
| D1, round off | M+ | [2.24] | [11.5] | M+ key accumulates the display to Memory as they were. Then it rounds both the display and the Memory and puts them in fixed-point mode. Therefore, 9.22 + 2.24 = 11.46 = 11.5  2.24 = 2.2 |
| Case 2: M+= and M−= keys | C | 0 | — | |
| | CM | 0 | 0 | |
| | 402 | 402 | 0 | |
| | × | 402 | 0 | |
| | 7005 | 7005 | 0 | |
| | M+= | [2816010] | [2816010] | M+= performs += and then M+ functions if it were ×or ÷ |
| | M+= | 2816010 | [5632020] | M+= performs M+ function if there were no previous operation. |
| | M+= | 2816010 | [8448030] | |
| | C | 0 | — | |
| | CM | 0 | 0 | |
| | 3 | 3 | 0 | |
| | += | 3 | 0 | |
| | 2 | 2 | 0 | |
| | M−= | [1] | [−2] | If the previous operation is NOT × or ÷, M±= accumulates only the display to Memory. The display shows the sum of those 2 numbers. M−= changes the sign of the display, then accumulates the display to memory, then does the addition. |
| | M+= | [1] | [−1] | |
| | M+= | [1] | [0] | |
| | M−= | [−1] | [−1] | Successive use of M±= key accumulates the memory successively. Display remains unchanged except for the sign in the case of M−= |
| Case 3 +=, −= keys with Σ on | C | 0 | −1 | |
| | CM | 0 | 0 | |
| | 3 | 3 | 0 | |
| | × | 3 | 0 | |
| | 2 | 2 | 0 | |
| | += | [6] | [6] | |
| | += | 6 | [6] | |
| | += | 6 | [6] | |
| Case 4 | | | | |

TABLE V-continued
OPERATION EXAMPLES

| | | | | |
|---|---|---|---|---|
| S, T, RM keys | C | 0 | 18 | |
| | CM | 0 | 0 | |
| Σ on | a | a | 0 | Doing the $\frac{(a-b)}{(d-c)}$ |
| | += | a | a | |
| | b | b | a | |
| | −= | | | |
| | | $\boxed{a-b}$ | $\boxed{a-b}$ | |
| Σ off | C | 0 | a − b | C does not clear the Memory. |
| | c | c | a − b | |
| | −= | −c | a − b | |
| | d | d | a − b | |
| | += | | a − b | |
| | | $\boxed{d-c}$ | | |
| | / | d − c | a − b | Entering a divide command |
| | RM | | a − b | Memory content is recalled after the display was stored to storage register |
| | | $\boxed{a-b}$ | | |
| | RV | | a − b | RV reverses the content of display and that of the Storage Registers |
| | | $\boxed{d-c}$ | | |
| | += | | a − b | |
| | | $\boxed{\frac{a-b}{d-c}}$ | | |
| | RM | | a − b | RM recalls memory without storing the original number in display |
| | | $\boxed{a-b}$ | | |
| | ÷ | a − b | a − b | |
| | += | | a − b | $\frac{(a-b)}{(d-c)}$ is lost, the storage register has (a − b) from RV |
| | | $\boxed{1}$ | | key and $\frac{(a-b)}{(a-b)}$ gives a 1. |
| | c | c | a − b | |
| | M+ | c | | |
| | | | $\boxed{a-b+c}$ | |
| | T | | 0 | Total brings out Memory to display. Memory is cleared. |
| | | $\boxed{a-b+c}$ | | |
| | C | 0 | 0 | |
| | CM | 0 | 0 | |
| A | 3.21 | 3.21 | 0 | |
| practical | M+ = | 3.21 | 3.21 | |
| Example | 4.35 | 4.35 | 3.21 | |
| | M+ = | 7.56 | 7.56 | |
| | 5.20 | 5.20 | 7.56 | |
| | M+ = | | | Total amount of non-taxable grocery items. |
| | | $\boxed{12.76}$ | $\boxed{12.76}$ | |
| | C | 0 | 12.76 | |
| | 7.19 | 7.19 | 12.76 | |
| | += | 7.19 | 12.76 | |
| | 8.00 | 8.00 | 12.76 | |
| | += | 15.19 | 12.76 | |
| | 9.24 | 9.24 | 12.76 | |
| | += | | 12.76 | Total amount of Taxable items. |
| | | $\boxed{24.43}$ | | |
| | × | 24.43 | 12.76 | |
| | 5.25 | 5.25 | 12.76 | |
| D2 | A/D | 1.28 | 12.76 | 5 ¼% State Sales Tax applied to taxable items. |
| Round off | += | | 12.76 | |
| | | $\boxed{25.71}$ | | |
| | M+ | 25.71 | | |
| | | | $\boxed{38.47}$ | |
| | T | | | Total amount purchased. |
| | | $\boxed{38.47}$ | $\boxed{0}$ | |

EXAMPLE NO. 8: Different uses of RV key

| | KEY | DISPLAY | STORAGE REGISTER | COMMENT |
|---|---|---|---|---|
| Case 1 | a | a | 0 | |
| K on | × | a | a | |
| | b | b | a | |

TABLE V-continued
OPERATION EXAMPLES

| | | | | |
|---|---|---|---|---|
| | += | ab | [a] | The constant-multiplicand |
| | c | c | a | |
| | −= | [−ac] | a | |
| | d | d | a | |
| | += | [ad] | a | |
| | RV | a | [ad] | RV changes the constant in constant mode operation |
| | e | e | ad | |
| | += | [ade] | ad | |
| | f | f | ad | |
| | −= | [−adf] | ad | |
| Case 2 | C | 0 | 0 | Doing the $\frac{d}{(a \times b) + c}$ |
| K off | CM | 0 | 0 | |
| | a | a | 0 | |
| | × | a | a | |
| | b | b | a | |
| | += | ab | a | |
| | c | c | ab | |
| | += | [ab + c] | ab | Computing the denominator first and then the division |
| | ÷ | ab + c | ab + c | |
| | d | d | ab + c | |
| | RV | [ab + c] | [d] | |
| | += | $\frac{d}{ab + c}$ | ab + c | |

EXAMPLE NO. 9: Uses of RV, RM, S and T keys

| | KEY | DISPLAY REGISTER | CONSTANT REGISTER | MEMORY REGISTER | COMMENT |
|---|---|---|---|---|---|
| K off | C | 0 | 0 | — | |
| D3 | CM | 0 | 0 | 0 | |
| Σ off | 3.10 | 3.10 | 0 | 0 | |
| | × | 3.10 | 3.10 | 0 | |
| | M− | [3.1] | 3.10 | [−3.100] | (1) Memory accumulation is always in Fixed-Point mode |
| | | | | | (2) M+, M−, RV keys display in floating mode, i.e., losing trailing zero |
| | | | | | (3) M− subtracts the display from the memory without changing the sign of display. |
| | | | | | (4) M+, M− do not change internal states, i.e., multiply is still in effect |
| | 4.2 | 4.2 | 3.10 | −3.100 | |
| | += | [13.020] | 3.10 | −3.100 | |
| | RV | [3.1] | 13.020 | −3.100 | (1) RV displays the number in Floating mode |
| | | | | | (2) RV key, like RM, S, T, A/D, acts as a number entry |
| | ÷ | 3.1 | 3.1 | −3.100 | |
| | 2 | 2 | 3.1 | −3.100 | |
| | M+= | [1.550] | 2 | [−1.550] | |
| D1 | 7.1 | 7.1 | 1.550 | −1.550 | |
| | × | 7.1 | 7.1 | −1.550 | |
| | RM | [−1.550] | 7.1 | −1.550 | (1) RM recalls the memory and displays it the way it is in memory, i.e., not Floating or Fixed-point mode. |

TABLE V-continued
OPERATION EXAMPLES

| | | | | |
|---|---|---|---|---|
| M+= | | 7.1 | | (2) RM acts as a number entry |
| | ⬚ −11.0 | | ⬚ −12.6 | |
| S | | −11.0 | −12.6 | Subtotal, like total, saves the displayed number only if it was not a number entry. |
| | ⬚ −12.6 | | | |
| ÷ | −12.6 | −12.6 | −12.6 | |
| 2.1 | 2.1 | −12.6 | −12.6 | |
| M+= | −6.0 | 2.1 | | |
| | | | ⬚ −18.6 | |
| 4.5 | 4.5 | −6.0 | −18.6 | |
| T | | −18.6 | ⬚ 0 | (1) T, like S, terminates a number entry but does not save the entered number. |
| | ⬚ −18.6 | | | |
| ÷ | −18.6 | −18.6 | 0 | |
| 4 | 4 | −18.6 | 0 | |
| += | | 4 | 0 | |
| | ⬚ −4.7 | | | |

EXAMPLE NO. 10: Property of M+, M− keys accumulating the display to memory register without changing internal states.

| | KEY | DISPLAY | MEMORY | COMMENT |
|---|---|---|---|---|
| DI | C | 0 | — | |
| K off | CM | 0 | 0 | (1) Memory Accumulation is always in Fixed-point mode |
| | 3 | 3 | 0 | |
| | × | 3 | 0 | (2) M+, M− keys are effective at any time i.e., after Number entry, function keys, ×, ÷, +=, etc. |
| | M+ | 3 | | |
| | | | ⬚ 3.0 | |
| | 4 | 4 | 3.0 | (3) Chain operation may be continued after M+, M− keys because internal states are not changed. |
| | += | | 3.0 | |
| | | ⬚ 12.0 | | |
| | 3 | 3 | 3.0 | |
| | × | 3 | 3.0 | |
| | M− | 3 | | |
| | | | ⬚ 0.0 | |
| | 4 | 4 | 0.0 | |
| | += | | 0.0 | |
| | | ⬚ 12.0 | | |
| | 3 | 3 | 0.0 | |
| | × | 3 | 0.0 | |
| | 5 | 5 | 0.0 | |
| | M− | 5 | | |
| | | | ⬚ −5.0 | |
| | += | | −5.0 | |
| | | ⬚ 15.0 | | |
| | 2 | 2 | −5.0 | |
| | M+ | 2 | | |
| | | | ⬚ −3.0 | |
| | × | 2 | −3.0 | |
| | 7 | 7 | −3.0 | |
| | += | | −3.0 | |
| | | ⬚ 14.0 | | |
| | 2 | 2 | −3.0 | |
| | × | 2 | −3.0 | |
| | 3 | 3 | −3.0 | |
| | += | | −3.0 | |
| | | ⬚ 6.0 | | |
| | M− | 6 | | |
| | | | ⬚ −9.0 | |
| | 4 | 4 | −9.0 | |
| | × | 4 | −9.0 | |
| | 5 | 5 | −9.0 | |
| | × | | −9.0 | |
| | | ⬚ 20 | | |
| | M− | 20 | | |
| | | | ⬚ −29.0 | |

TABLE V-continued

OPERATION EXAMPLES

|  | 7 | 7 | −29.0 |
|--|--|--|--|
|  | += | | −29.0 |
|  |  | 140.0 | |

EXAMPLE NO. 11: CAUTION

| | KEY | DISPLAY | MEMORY | COMMENT |
|---|---|---|---|---|
| | C | 0 | — | The Problem: While M+, M− keys do not change the internal states of the machine, number entry that is not terminated is still in effect. |
| | CM | 0 | 0 | |
| Round off | 1.23 | 1.23 | 0 | |
| | M+ | 1.23 | | |
| | | | 1.2 | |
| | 45 | 1.2345 | 1.2 | |
| | M+ | 1.2345 | | |
| | | | 2.4 | |

TABLE VI. PROGRAM LISTING

```
ROM LOC.   INST. WORD
                                          ------MASKS
000        *
001        ALL      EQU    0
002        EXP1     EQU    1
003        EXP      EQU    2
004        EXP11    EQU    3
005        MANT     EQU    4
006        MLSD1    EQU    5
007        MLD1     EQU    5
008        MMSD1    EQU    6
009        MLSD5    EQU    7
00A        OPT1     EQU    8
00B        OPT11    EQU    9
00C        OPT      EQU    10
                    LLSD1    EQU    11
                    OV1      EQU    12
                                          ------FLAGS
000        *
001        ATEMP1   EQU    0
002        ATEMP4   EQU    8
003        ATEMP5   EQU    11
004        AERR     EQU    13       OVERFLOW
005        AOV      EQU    7
006        ARV      EQU    12
007        AA/D     EQU    5        SIGN OF A
008        ASA      EQU    9
009        AMEMIND  EQU    15
00A        RFLT     EQU    16       FLOATING MODE FLAG
00B        ATEMP3   EQU    3
00C        ASEA     EQU    10       SIGN EXP OF A
00D        AEADV    EQU    4        EXP A OV
00E        ASC      EQU    1        SIGN OF C
00F        ASEC     EQU    2        SIGN EXP C
010        APREV1   EQU    14       PREV OP 1
011        APREV2   EQU    6        PREV OP 2
012        BTEMP2   EQU    27
013        BDATENT  EQU    20       DATA ENTRY(DISPLAY FLAG)
014        POPT     EQU    24       DEC PT
015        BSIGMA   EQU    28
016        BK       EQU    21       K-FLAG
017        BSR      EQU    25       SIGN OF R
                    BM+      EQU    29       M+ FLAG
                    BNUM     EQU    23       NAT NUM IF 0, DP NUM IF 1
```

| | | | | | | | |
|---|---|---|---|---|---|---|---|
| 010 | 1 1110 0100 1010 | | MSEH | EQU | 26 | SIGN EXP B | |
| 011 | 1 1110 **** **** | | PSD | EQU | 17 | SIGN OF D | |
| 012 | 1 1110 1001 1010 | | BSFD | EQU | 18 | SIGN EXP D | |
| 013 | 1 1110 1000 0000 | | BN+- | EQU | 19 | | |
| 014 | 1 1110 1010 1010 | | BCURR1 | EQU | 30 | CURR OP 1 | |
| 015 | 1 1111 0000 0000 | | BCURR2 | EQU | 72 | | |
| 016 | 1 1110 1010 1010 | | BPRE2 | EQU | 31 | | |
| 017 | | | * | | | | START |
| 000 | 1 1111 0100 0110 | | | ZIDL | | MAKING SURE ID LATCH IS RESET | |
| 001 | 0 1*** **** **** | | | BO | CLR | MAKING SURE THAT COND = 1 | |
| 002 | 1 1110 1001 1010 | | | FLBREG4 | | CLEAR DOES NOT CLEAR MEM FLAGS | |
| 003 | 1 1110 1010 0000 | CLR | | CLFB | | | |
| 004 | 1 1110 1010 1010 | | | REGFLB4 | | | |
| 005 | 1 1111 0000 0000 | | | CLFA | | | |
| 006 | 0 0000 0000 0000 | | | CLA | ALL | | |
| 007 | 1 0000 1000 0000 | | | CLC | ALL | | |
| 008 | 0 1*** **** **** | | | BO | K5 | ALWAYS BRANCH | |
| 009 | | | *------ | | | KEYBOARD ENTRY | |
| 00A | 1 1111 1010 0110 | | | TF | BDATENT | | |
| 00B | 1 1111 1010 1110 | KIA | | TF | BK | | |
| 00C | 0 **** **** **** | KLB | | BZ | OP6 | | |
| 00D | 1 1111 1110 1110 | K6 | | TF | BM+ | | |
| 00E | 1 1111 0110 0100 | | | BZ | OP43 | THE A += C M+= CASE | |
| 00F | 1 1101 1010 0001 | PREL | | ZF | ARV | | |
| 010 | 0 1*** **** **** | PRE | | CAK | MLSD1 | | |
| 011 | 0 0000 1000 0110 | | | BO | A2 | | |
| 012 | 1 1111 0100 1100 | A91 | | CLA | ALL | | |
| 013 | 1 1111 1011 1011 | | | ZF | ASA | | |
| 014 | 1 1111 1011 1011 | A0 | | SF | BNUM | SET A TEMP FLAG | |
| 015 | 0 1*** **** **** | RV2 | | BO | RV | RETURN TO A92, OR ALWAYS BRANCH IF RV KEY | |
| 016 | 1 1111 1101 1011 | M-= | | FF | ASA | | |
| 017 | 1 1111 1011 1011 | M+= | | SF | ATEMP5 | | |
| 018 | 1 1111 1110 1011 | M+=2 | | SF | BM+ | | |
| 019 | 0 0000 1000 0111 | | | BO | K7 | ALWAYS BRANCH | |
| 01A | 1 1111 1011 1011 | T | | SF | BCURR2 | TEMP | |
| 01B | 1 1111 1010 0110 | SU | | TF | BDATENT | | |
| 01C | 1 1110 1010 0010 | RM | | FLAREG8 | | | |
| 01D | 0 0000 0010 0100 | | | BD | RM2 | NUMBER ENTRY NOT SAVED FOR RM, ALWAYS BRANCH | |
| 01E | 1 1110 1010 1010 | | | AAKC | ALL | | |
| 01F | 1 1110 1001 1010 | RM2 | | REGFLA4 | | | |
| | | | | FLBREG4 | | | |

| | | | | | |
|---|---|---|---|---|---|
| C20 | 1 1111 0011 0010 | 0087 | | REGFLA9 | |
| C21 | 1 1111 0011 1110 | 0088 | | ADKA ALL | |
| C22 | 1 1111 0110 0011 | 0089 | | SF ARV | |
| C23 | 1 **** **** **** | 0090 | | TF BCUR02 TEMP | |
| C24 | 1 **** 1000 0101 | 0091 | C4 | OO OP3 RM,SY, TERMINATES NUMBER ENTRY |
| C25 | 1 0010 0000 0001 | 0092 | | CLD ALL | |
| C26 | 1 1111 1010 1010 | 0093 | | ZREG LSR 4 BITS ARE 0 |
| C27 | 1 **** **** **** | 0094 | | REGFLR4 | |
| C28 | 1 **** **** **** | 0095 | | BO OP3 ALWAYS BRANCH, T AND CM TERMINATES NUMBER ENTRY |
| C29 | 1 1111 7010 0110 | 0096 | CE | TF RDATENT |
| C2A | 1 1111 0110 1100 | 0097 | CI | ZF AFRR |
| C2B | 0 **** 1100 **** | 0098 | | BZ LOCK NO NUMBER ENTERED,CEONLY RESET OV FLAG,CI NEVERDO THIS |
| C2C | 1 1111 1100 0100 | 0099 | | ZF BDPT |
| C2D | 0 **** **** **** | 0100 | | BO PI ALWAYS BRANCH |
| C2E | 1 1111 0110 1100 | 0101 | RS | ZF AERR |
| C2F | 0100 1111 1100 | 0102 | | SRLA MANT |
| C30 | 1 1000 0000 1110 | 0103 | | SAKA DPT1 |
| C31 | 1 **** **** **** | 0104 | | BO LOCK |
| C32 | 1 1111 11*0 0100 | 0105 | K5 | ZF BDPT |
| C33 | 1 1010 1000 0100 | 0106 | LOCK2 | CLA DPT |
| C34 | 1 1111 0011 1100 | 0107 | CM2 | ZF AOV |
| C35 | 1 **** **** **** | 0108 | | BO LOCK ALWAYS BRANCH |
| C36 | 1 1011 0011 0011 | 0109 | DIV | SF BCURR2 |
| C37 | 1 1111 0011 0011 | 0110 | MULT | SF BCURR1 |
| C38 | 1 1111 0110 1110 | 0111 | | TF APREV1 |
| C39 | 1 **** **** **** | 0112 | | BO OP6 |
| C3A | 1 0110 0110 0011 | 0113 | | TF ARV |
| C3B | 1 1111 1100 1100 | 0114 | | BZ K1B |
| C3C | 0 1000 0000 1001 | 0115 | | BO K1A ALWAYS BRANCH |
| C3D | 1 1111 0100 1001 | 0116 | = | FF ASA CHANGE SIGN OF A |
| C3E | 1 1101 0101 0001 | 0117 | P= | WAIT 10 |
| C3F | 1 1111 0001 0001 | 0118 | | KTEST S SIGMA SWITCH DOWN |
| C40 | 1 1111 1111 0111 | 0119 | | BZ M+=? |
| C41 | 1 0000 0010 1111 | 0120 | K7 | TF ARV |
| C42 | 1 1111 0110 1110 | 0121 | | TF APREV1 |
| C43 | 1 0000 0000 1110 | 0122 | | RZ PREI |
| C44 | 1 1111 1010 0110 | 0123 | | TF RDATENT |
| C45 | 0 1000 0000 1010 | 0124 | K1 | BO K6 A NUMBER HAS BEEN ENTERED |
| C46 | 1 1111 1110 1100 | 0125 | | TF BM+ |
| C47 | 1 1111 1110 1100 | 0126 | | ZF BM+ |
| C48 | 0 **** **** **** | 0127 | | BO OP12 |

| | | | | | | |
|---|---|---|---|---|---|---|
| 04A | 1 1111 •••• 1110 | | 0128 | | TF | ATEMP5 | |
| 04B | 0••• 1111 1110 1••• | | 0129 | | BZ | OP43 | |
| 04C | 1 1111 1010 1100 | | 0130 | OP12 | ZF | BK | |
| 04D | 1 1111 1011 0111 | | 0131 | OP1 | XF | APREV1 | |
| 04E | 1 1111 1011 0111 | | 0132 | | XF | APREV2 | |
| 04F | 1 1111 1011 0011 | | 0133 | OP3 | SF | BDATE1T | |
| 04F | 1 1111 1100 •••• | | 0134 | | ZF | BDPT | |
| 050 | 0 1••• 1111 0110 | | 0135 | | BO | LOCK | ALWAYS BRANCH |
| 051 | 1 0101 1111 0100 | | 0136 | M9 | SRLC | MANT | |
| 052 | 1 0101 1011 0001 | | 0137 | | CCK | MLSD1 | |
| 053 | 0 •••• •••• •••• | | 0138 | | BZ | M8 | |
| 054 | 1 0101 1111 0100 | | 0139 | | SRLC | ALL | |
| 055 | 1 0101 1011 0001 | | 0140 | | CCK | MLSD1 | |
| 056 | 1 0101 1111 0100 | | 0141 | | SLLC | ALL | |
| 057 | 0 •••• •••• •••• | | 0142 | | BZ | M9A | |
| 058 | 1 0100 0110 0110 | | 0143 | | SRLA | MANT | |
| 059 | 1 1011 0110 0110 | | 0144 | M5 | SCKC | MANT | |
| 05A | 1 0100 1011 0001 | | 0145 | | BZ | LLSD1 | |
| 05B | 0 •••• •••• •••• | | 0146 | | BZ | M9 | |
| 05C | 1 0100 0101 0110 | | 0147 | | AABA | MANT | |
| 05D | 1 0101 0101 0110 | | 0148 | | BO | M5 | |
| 05E | 1 0100 1110 0110 | | 0149 | | SRLA | MANT | |
| 05F | 1 1000 0110 1111 | | 0150 | | SAKA | DPT1 | |
| 060 | 0 1000 1010 0111 | | 0151 | | SRLS | MANT | |
| 061 | 1 1000 0100 1001 | | 0152 | | AAKA | OV1 | |
| 062 | 1 1000 0010 1111 | | 0153 | A/D | BO | M5 | ALWAYS BRANCH |
| 063 | 1 1000 0010 0110 | | 0154 | | ARKA | DPT1 | |
| 064 | 1 1111 0110 •••• | | 0155 | | SF | ARV | |
| 065 | 1 1000 0000 1111 | | 0156 | OP | BO | PRE | ALWAYS BRANCH |
| 066 | 1 1111 1100 0011 | | 0157 | OP | SF | BDPT | |
| 067 | 0 1••• •••• 1101 | | 0158 | | BO | P2 | ALWAYS BRANCH |
| 068 | 1 1111 0100 1101 | | 0159 | CS | FF | ASA | ALWAYS BRANCH |
| 069 | 1 1111 •••• 1101 | | 0160 | | BO | LOCK | ALWAYS BRANCH |
| 06A | 1 1111 0100 1101 | | 0161 | M– | FF | ASA | |
| 06B | 1 1111 1011 1011 | | 0162 | | SF | BCURR2 | |
| 06C | 1 1111 1011 1011 | | 0163 | M+ | SF | RM+– | |
| 06D | 0 •••• •••• •••• | | 0164 | | BO | OP43 | ALWAYS BRANCH |
| 06E | 1 1000 0010 0110 | | 0165 | ( | AAKA | DPT1 | |
| 06F | 1 1001 1010 0001 | | 0166 | ) | CAK | OPT11 | |
| 070 | 0 •••• •••• •••• | | 0167 | I2 | BZ | (3 | |
| 071 | 1 1000 1010 0110 | | 0168 | | SAKA | DPT1 | |

| Addr | Binary | | | Op | Operand | Comment |
|---|---|---|---|---|---|---|
| 0172 | 1 0100 1110 0110 | | | SRLA | MANT | |
| 0173 | 0 1000 0110 1111 | | | BO | C2 | ALWAYS BRANCH |
| 0174 | 1 1110 0010 0110 | | (3 | AAKA | DPT | |
| 0175 | 0 1*** **** **** | | | BO | LOCK | ALWAYS BRANCH |
| 0176 | *----PRENORMALIZING A NUMBER---- | | | | | |
| 0174 | 1 1111 0101 0110 | A13 | | TF | ASEA | |
| 0175 | 0 1*** **** **** | | | BO | A7 | |
| 0176 | 1 0001 1010 0001 | A5 | | CAK | EXP1 | |
| 0177 | 0 0*** **** **** | | | BZ | A6 | EXP OF A IS ZERO |
| 0178 | 1 0001 1010 0110 | | | SAKA | EXP2 | |
| 0179 | 0 0*** **** **** | | | BO | A2 | ALWAYS BRANCH |
| 017C | 1 1020 0010 0110 | A3 | | AAKA | DPT1 | |
| 017D | 1 0110 1010 0001 | | | CAK | MMSD1 | |
| 017E | 1 1000 0111 1100 | | | BO | A13 | |
| 017F | 1 0100 0100 0110 | | | SLLA | MANT | |
| 0180 | 1 1111 1101 1110 | A2 | | TF | BTEMP2 | A TEMP FLAG |
| 0181 | 0 0*** **** **** | | | BZ | M23 | |
| 0182 | 1 0001 1010 0001 | | | CAK | DPT11 | |
| 0183 | 0 0110 0111 1100 | | | RZ | A3 | |
| 0184 | 1 0110 1010 0001 | | | CAK | MMSD1 | |
| 0185 | 0 0*** **** **** | | | BO | A9 | |
| 0186 | 1 0100 0100 0110 | | | SLLA | MANT | |
| 0187 | 1 1111 0110 0110 | A1 | | TF | ASEA | |
| 0188 | 0 0*** **** **** | | | BZ | A7 | |
| 0189 | 0 1000 1000 0101 | | | BO | A5 | ALWAYS BRANCH |
| 018A | 1 1111 0101 0100 | A6 | | FF | ASEA | |
| 018B | 1 0001 0010 1100 | A7 | | AAKA | EXP1 | |
| 018C | 0 1000 1000 0101 | | | BO | A2 | NO C/B |
| 018D | 1 1111 0010 0011 | | | SF | AEAOV | |
| 018E | 0 0*** **** 0101 | | | BO | A2 | ALWAYS BRANCH |
| 018F | 1 1111 1110 1101 | A92 | | TF | BPRE2 | |
| 0190 | 0 1111 1101 1101 | | | FF | BPRE2 | |
| 0191 | 0 1000 1111 1111 | | | BO | PRE | |
| 0192 | 1 1111 0200 1111 | | | TF | BSIGNA | |
| 0193 | 1 1111 1110 1110 | | | TF | AA/D | |
| 0194 | 1 1111 1010 1100 | | | ZF | AA/D | |
| 0195 | 0 0*** **** 1110 | | | BZ | A/S | |
| 0196 | 1 1111 0110 0110 | | | TF | APREV1 | |
| 0197 | 0 *** **** **** | | | BZ | M/D | |
| 0208 | *----ADD OR SUBTRACT---- | | | | | |
| 0209 | 1 0010 0011 0001 | A/S | | CREG | EXP | |

| Addr | Bits | | Label | Op | Arg | Comment |
|---|---|---|---|---|---|---|
| C99 | 1 1111 0101 0111 | | 0210 | CF | ASEA | |
| C9A | 1 1 0101 **** | | 0211 | BO | AS2 | UNLIKE SIGN EXP |
| C9B | 1 1100 0001 | | 0212 | CAB | EXP | |
| C9C | 1*** **** | | 0213 | BO | AS3 | |
| C9D | 1 1111 1111 0010 | | 0214 | EXAB | ALL | |
| C9E | 1 0010 1100 0010 | | 0215 | XF | ASA | |
| C9F | 1 1111 1100 1111 | | 0216 | AS3 | SABC | EXP |
| CA0 | 1 0010 0101 0110 | | 0217 | | TF | ASEA |
| CA1 | 1*** **** | | 0218 | | BO | AS4 |
| CA2 | 1 0000 0000 0010 | | 0219 | | EXAB | ALL |
| CA3 | 1 1111 1100 1111 | | 0220 | | XF | ASA |
| CA4 | 1 0001 1011 0100 | | 0221 | AS4 | SCKC | EXP1 |
| CA5 | 0*** **** | | 0222 | | BZ | AS5 |
| CA6 | 1 1101 1111 1111 | | 0223 | | SRLB | MANT |
| CA7 | 0 1101 1010 0100 | | 0224 | | BO | AS4 | ALWAYS BRANCH |
| CA8 | 1 1111 1101 0110 | | 0225 | | TF | BSER |
| CA9 | 0*** **** | | 0226 | AS2 | BZ | AS6 |
| CAA | 1 0000 0000 0010 | | 0227 | | EXAB | ALL |
| CAB | 1 1111 1100 1111 | | 0228 | AS7 | XF | ASA |
| CAC | 1 0101 0111 1011 | | 0229 | | XF | ASEA |
| CAD | 1 1111 1010 0001 | | 0230 | AS6 | CAK | MLSDI |
| CAE | 0 0000 1010 1010 | | 0231 | | BZ | AS7 | MANT OF A IS ZERO |
| CAF | 1 0010 0100 0100 | | 0232 | | AABC | EXP |
| CB0 | 0*** **** | | 0234 | | BZ | AS1 | IF HAVE C/8 YOU LOOSE THIS NUMBER, A IS THE ANSWER |
| CB1 | 0 1000 0101 0100 | | 0234 | | BO | AS4 | ALWAYS BRANCH |
| CB2 | 1 1100 0001 **** | | 0235 | | CAB | MANT |
| CB3 | 1*** **** | | 0236 | | BO | AS9 |
| CB4 | 1 0000 0000 0010 | | 0237 | | EXAB | ALL |
| CB5 | 1 1111 1100 1111 | | 0238 | | XF | ASA |
| CB6 | 1 0101 0111 1011 | | 0239 | AS9 | CF | ASA |
| CB7 | 0*** **** | | 0240 | | BZ | AS8 |
| CB8 | 1 0100 1100 0110 | | 0241 | | SABA | MANT |
| CB9 | 1*** **** | | 0242 | | BO | AS1 | ALWAYS BRANCH |
| CBA | 1 0101 0100 0110 | | 0243 | | AABA | MANT |
| CBB | 1 0010 0100 0110 | | 0244 | AS8 | REGC | EXP |
| CBC | 1 0010 0101 0110 | | 0245 | AS1 | TF | RCURR2 | COMING FROM M- |
| CBD | 1*** **** | | 0246 | | BO | M85 |
| CBE | 1 1111 0010 1101 | | 0247 | | FF | ASC |
| CBF | 1*** **** | | 0248 | | RO | M85 | ALWAYS BRANCH |
| | | | 0249 | *----- | MULTIPLY OR DIVIDE ----- |
| CC0 | 1 0000 0000 0010 | | 0250 | M10 | EXAB | ALL |

| Addr | Binary | Label | Op | Arg | Comment |
|---|---|---|---|---|---|
| 0CC1 | **** **** **** | 0251 | | BO | M11 | ALWAYS BRANCH |
| 0CC2 | 1111 0011 1111 | 0252 | K/D | TF | APREV2 | |
| 0CC3 | 1111 1111 1100 | 0253 | | BO | M1 | * |
| 0CC4 | 1111 1101 1111 | 0254 | | TF | BK | K-FLAG |
| 0CC5 | 1111 1101 0000 | 0255 | | BZ | M10 | CONSTANT IN B |
| 0CC6 | 0111 1111 1111 | 0256 | | XF | ASA | |
| 0CC7 | 0000 0001 1001 | 0257 | | XF | ASEA | |
| 0CC8 | **** **** **** | 0258 | M11 | CAK | MLSD1 | ZERO DIVISOR |
| 0CC9 | 0000 0010 0010 | 0259 | | BZ | OVERFLOW | |
| 0CCA | 1111 1111 1111 | 025C | | EXAB | ALL | |
| 0CCB | 1111 1111 1111 | 025D | | ZF | BK | |
| 0CCC | **** **** **** | 025E | | WAIT | 11 | |
| 0CCD | 1111 1111 1111 | 025F | | KTESTS | | LOOKING FOR K-SWITCH |
| 0CCE | 1111 1011 1011 | 0264 | | BO | M22 | K UP |
| 0CCF | 1011 0101 1110 | 0265 | | SF | BK | K DOWN |
| 0CD0 | 1111 1111 1011 | 0266 | | CF | ASA | |
| 0CD1 | 0100 0100 0111 | 0267 | M22 | ZF | ASA | |
| 0CD2 | 1111 1111 1011 | 0268 | | BZ | M2 | |
| 0CD3 | 1011 0101 1011 | 0269 | | SF | ASEA | |
| 0CD4 | 1111 1011 1011 | 0270 | M2 | CF | ASEA | |
| 0CD5 | 0101 0101 0111 | 0271 | | BO | M20 | UNLIKE EXP SIGN |
| 0CD6 | **** **** **** | 0272 | | TF | APREV2 | |
| 0CD7 | 0010 0100 0110 | 0273 | M21 | RZ | N3 | |
| 0CD8 | 1111 1111 1111 | 0274 | | AARA | EXP | |
| 0CD9 | **** **** **** | 0275 | | BO | M41 | |
| 0CDA | 1111 0001 0001 | 0276 | M41 | SF | AEAOV | |
| 0CDB | 0**** **** **** | 0277 | | CAK | MLSD1 | TAKES CARE OF 0/A,A*0,0*0 |
| 0CDC | 0100 1100 1100 | 0278 | | BZ | M3 | |
| 0CDD | 0100 1111 1111 | 0279 | | AAKC | MANT | |
| 0CDE | **** **** **** | 0280 | | CLA | MANT | |
| 0CDF | 1111 0011 1111 | 0281 | | TF | APREV2 | |
| 0CE0 | 1000 0101 1111 | 0282 | M6 | BO | M5 | * |
| 0CE1 | 0100 0101 0001 | 0283 | | CCR | MANT | |
| 0CE2 | 0100 1101 1001 | 0284 | | BZ | M7 | |
| 0CE3 | 1111 1111 1111 | 0285 | | SCBC | MANT | |
| 0CE4 | 1111 1111 1110 | 0286 | | AAKA | MLSD1 | |
| 0CE5 | 1111 0111 0011 | 0287 | | BO | M6 | ALWAYS BRANCH |
| 0CE6 | 1000 1111 0110 | 0288 | M84 | AAKA | OPT1 | |
| 0CE7 | 1110 0110 1111 | 0289 | M8 | APKC | ALL | |
| 0CE8 | 1111 1111 1010 | 0290 | | FLBXFGR | | |
| 0CE9 | 1110 1111 1010 | 0291 | | REGFLA4 | | |

| | | | | | |
|---|---|---|---|---|---|
| 0F... | 1111 1111 1111 1111 | 0292 | | TF | BCURR1 |
| 0FB | 1111 1111 1010 1111 | 0293 | | BO | M83A |
| 0FC | 1111 1110 1100 0110 | 0294 | | ZF | BK |
| 0FD | 1111 1111 1011 1111 | 0295 | M83A | TF | ARV |
| 0FE | 1111 1010 1010 1111 | 0296 | | BO | M83 |
| 0FF | 1111 1111 1011 1111 | 0297 | | TF | BK |
| 0F0 | **** **** **** **** | 0298 | | BZ | MR3B |
| 0F1 | 1111 0111 0100 0100 | 0299 | | ZF | APREV1 COME FROM A/D |
| 0F2 | 1100 1011 0011 0001 | 0300 | | CCK | OV1 |
| 0F3 | 0101 1011 1111 0110 | 0301 | | BZ | M85 |
| 0F4 | 1111 **** **** **** | 0302 | | SRLC | MANT |
| 0F5 | 1100 1010 1111 0110 | 0303 | M85 | CAK | MLSD1 |
| 0F6 | 1111 1010 0001 0001 | 0304 | | BO | POST |
| 0F7 | 0110 1000 0000 0000 | 0305 | | CLA | ALL |
| 0F8 | 1111 0100 0100 1101 | 0306 | | ZF | ASA |
| 0F9 | 1111 **** **** **** | 0307 | | BQ | POST ALWAYS BRANCH |
| 0FA | 0011 0010 0011 **** | 0308 | | TF | APREV2 |
| 0FB | 1101 1101 **** **** | 0309 | M20 | BZ | M21 |
| 0FC | 1100 1000 0100 1101 | 0310 | | CAR | EXP |
| 0FD | 0101 1110 0011 0001 | 0311 | | BQ | M3 |
| 0FE | 1111 **** 0101 0101 | 0312 | | FF | ASEA |
| 0FF | 0010 1110 1100 0100 | 0313 | M3 | SABC | EXP |
| 100 | 1111 1011 1001 0001 | 0314 | | BO | M4 |
| 101 | 0010 1100 0010 0110 | 0315 | | EXAB | ALL |
| 102 | 0011 1100 1100 0101 | 0316 | | SABC | EXP |
| 103 | 0010 1100 0010 0110 | 0317 | | EXAB | ALL |
| 104 | 1111 0011 0011 **** | 0318 | | TF | APREV2 |
| 105 | 1111 1011 1001 0101 | 0319 | | BO | M4 * |
| 106 | 1111 **** 0101 0101 | 0320 | | FF | ASEA |
| 107 | 1111 0101 1100 0100 | 0321 | M4 | ACKA | EXP |
| 108 | 1111 1011 0011 0001 | 0322 | | BO | M41 ALWAYS BRANCH |
| 109 | 1100 1010 1010 0001 | 0323 | | CAK | OV1 |
| 10A | 1000 1110 1110 0110 | 0324 | N7 | BO | M94 DIVISION DONE, WITH OR WITHOUT REMAINDER |
| 10B | 1100 1010 1111 0010 | 0325 | | CAK | MLSD1 |
| 10C | 1111 1101 1001 0111 | 0326 | | SF | BTEMP2 |
| 10D | 0011 1101 1010 1100 | 0327 | | BZ | A1 RETURN TO M23 |
| 10E | 1111 1101 1010 1011 | 0328 | M23 | ZF | BTEMP2 |
| 10F | 0110 1101 0111 0110 | 0329 | | SLLA | MANT |
| 110 | 1101 1011 0111 0010 | 0330 | | CCK | MLSD1 |
| 111 | 0001 1001 0110 1100 | 0331 | | BZ | M7 |
| 112 | 0100 0111 0100 0100 | 0332 | | SLLC | MANT |

| | | | | | | |
|---|---|---|---|---|---|---|
| 113 | 1 100 1110 0001 | 0323 | | BO | M6 | ALWAYS BRANCH |
| 114 | 1 100 0110 0110 | 0324 | 49A | SLLR | MANT | |
| 115 | 1 000 0101 0110 | 0325 | | SAKA | DPT1 | |
| 116 | 1 101 0101 1001 | 0326 | | BO | M5 | ALWAYS BRANCH |
| 117 | 1 101 0015 1011 | 0327 | 4833 | SF | AA/D | |
| 118 | 1 115 1111 0010 | 0328 | | BO | M83 | ALWAYS BRANCH |
| 119 | 0 **** **** **** | 0329 | * | POST NORMALIZATION | | |
| 11A | 1 100 1010 0110 | 0330 | R7 | SAKA | DPT1 | |
| 11B | 0 **** **** **** | 0331 | | BO | POST2 | ALWAYS BRANCH |
| 11C | 1 0100 1110 0110 | 0332 | R2 | SRLA | MANT | |
| 11D | 1 0001 1010 0001 | 0333 | POST2 | CAK | EXP1 | |
| 11E | 0 **** **** **** | 0334 | | BO | R21 | |
| 11F | 1 111 0010 0110 | 0335 | R1 | TF | AEAOV | |
| 120 | 0 **** **** **** | 0336 | | BO | R9 | |
| 121 | 1 111 0010 0100 | 0337 | | ZF | AEAOV | |
| 122 | 0 **** **** **** | 0338 | R21 | SAKA | EXP1 | |
| 123 | 1 0001 1010 0110 | 0339 | | BO | R20 | KILLING A COND CODE |
| 124 | 0 0001 0001 1011 | 0340 | | TF | ASEA | |
| 125 | 1 0001 0001 0001 | 0341 | | BZ | R2 | |
| 126 | 0 0011 0001 1010 | 0342 | R20 | CAK | EXP11 | |
| 127 | 0 0011 0001 1001 | 0343 | | BZ | R7 | |
| 128 | 1 0011 0011 0110 | 0344 | | SAKA | EXP11 | |
| 129 | 1 1011 0001 1011 | 0345 | OVERFLOW | SF | AOV | |
| 12A | 1 1001 0001 1100 | 0346 | | BO | POST2 | ALWAYS BRANCH |
| 12B | 1 0000 0000 0001 | 0347 | R3 | EXAB | ALL | ROUND DOWN |
| 12C | 1 0010 1100 0001 | 0348 | | CAB | DPT | |
| 12D | 0 0000 0000 0010 | 0349 | | EXAB | ALL | |
| 12E | 0 **** **** **** | 0350 | | BO | R32 | |
| 12F | 1 0100 1110 0110 | 0351 | | SRLA | MANT | |
| 130 | 1 1000 1010 0110 | 0352 | | SAKA | DPT1 | |
| 131 | 1 1001 1010 1010 | 0353 | | BO | R3 | ALWAYS BRANCH |
| 132 | 1 1111 1111 0110 | 0354 | OP42A | TF | BSIGMA | |
| 133 | 0 0000 0011 0011 | 0355 | | BZ | PRE | |
| 134 | 1 0000 1110 1111 | 0356 | OP44 | EXCD | ALL | |
| 135 | 1 1111 1111 1111 | 0357 | | XF | ASC | |
| 136 | 1 1111 1011 1110 | 0358 | | XF | ASEC | |
| 137 | 1 1111 1111 1100 | 0359 | | TF | BM+ | |
| 138 | 1 0000 1111 1110 | 0360 | | BM+ | | |
| 139 | 1 1111 1001 1110 | 0361 | | HZ | PRE | |
| 13A | 0 **** **** **** | 0362 | | TF | BM+- | |
| 13B | 0 **** **** **** | 0363 | | BO | POST | |

| | | | | | | |
|---|---|---|---|---|---|---|
| 13B | 1 1111 1000 0011 | | 0374 | | SF | BFLT | |
| 13C | 1 0001 1010 0001 | | 0375 | POST | CAK | EXP1 | |
| 13D | 0 0001 0001 1110 | | 0376 | | B7 | R1 | |
| 13E | 1 1111 0101 0111 | | 0377 | | TF | ASEA | |
| 13F | 1 1111 0010 0115 | | 0378 | | BO | R21 | |
| 140 | 1 1001 0010 1110 | | 0379 | | SAKA | EXP1 | |
| 141 | 1 1001 0010 1105 | | 0380 | | AAKA | DPT1 | |
| 142 | 1 1001 0001 1100 | | 0381 | | BQ | POST2 | ALWAYS BRANCH |
| 143 | 1 1111 1001 1110 | | 0382 | OP41 | TF | BM+- | |
| 144 | 0 **** **** **** | | 0383 | | RZ | LOCK | |
| 145 | 1 1111 1010 1110 | | 0384 | | TF | BK | |
| 146 | 1 1111 0110 0110 | | 0385 | | TF | ARV | COMING FROM RV, RM OP. ( |
| 147 | 1 1111 0100 1100 | | 0386 | | BZ | OP3 | |
| 148 | 0 0000 0100 1100 | | 0387 | | BO | OP1 | ALWAYS BRANCH |
| 149 | 1 1111 0101 0111 | | 0388 | R9 | ZF | ASEA | |
| 14A | 1 1111 0011 1110 | | 0389 | | TF | ADV | |
| 14B | 1 1111 1000 0111 | | 0390 | | TF | BCURR1 | |
| 14C | 1 0111 1000 0111 | | 0391 | | TF | RFLT | |
| 14D | 1 1111 0111 1110 | | 0392 | | BZ | FLOATING | |
| 14E | 1 1100 0111 0001 | | 0393 | R40 | WAIT | 14 | |
| 14F | 1 1111 1011 1011 | | 0394 | | SCAN | R | SET COND CODE IF FOUND SOMETHING |
| 150 | 1 1111 1010 1011 | | 0395 | | SF | BNUM | |
| 151 | 0 **** **** **** | | 0396 | | BZ | DATA | RETURN TO R30 |
| 152 | 1 1111 1100 1110 | | 0397 | | ZF | BNUM | |
| 153 | 1 1111 1000 0011 | | 0398 | FLOATING | SF | BFLT | |
| 154 | 0 0000 0010 1110 | | 0399 | | EXAR | ALL | |
| 155 | 1 1100 0010 0110 | | 0400 | | EXP11A | ALL | |
| 156 | 0 0011 0000 0110 | | 0401 | R30 | SRLA | ALL | BNUM MAY BE ON |
| 157 | 1 1010 1100 0001 | | 0402 | | CAB | DPT | |
| 158 | 1 0101 0010 1110 | | 0403 | | EXAB | ALL | |
| 159 | 0 0001 0010 1111 | | 0404 | | BZ | R8 | |
| 15A | 1 1101 1010 0001 | | 0405 | R6 | CAK | OV1 | |
| 15B | 0 1*** 1010 0001 | | 0406 | | BO | R80 | CANNOT ADJUST TO EQUAL DPT |
| 15C | 1 1010 1100 0001 | | 0407 | | CAR | DPT | |
| 15D | 0 1*** 1100 0001 | | 0408 | | BO | OP4A | V = P |
| 15E | 1 0100 0110 1110 | | 0409 | | SLLA | MANT | |
| 15F | 1 1001 0010 1110 | | 0410 | | AAKA | DPT1 | |
| 160 | 1 0001 0101 1010 | | 0411 | | BO | R6 | ALWAYS BRANCH |
| **** | FROM **** INVALID OPCODE. | | 0412 | P4D | MOVR1A | | |
| 161 | 1 1000 1010 0001 | | 0413 | R80 | CAK | DPT1 | |

| | | | | | | |
|---|---|---|---|---|---|---|
| 162 | 0 1001 0010 1111 | 0414 | | BO | RR | |
| 163 | 1 1001 0010 0110 | 0415 | | AAKA | DPT11 | |
| 164 | 1 1000 0010 1000 | 0416 | | AAKA | DPT1 | |
| 165 | 0 1001 0010 1000 | 0417 | | BO | OVERFLOW | ALWAYS BRANCH |
| 166 | 1 1111 1110 0110 | 0418 | R32 | TF | RFLT | |
| 167 | 1 1111 1111 1111 | 0419 | | WAIT | 15 | |
| 168 | 0 **** **** **** | 0420 | | KTEST | S | |
| 169 | 1 1101 1101 1111 | 0421 | | BZ | OP4R | ROUND DOWN |
| 16A | 1 1*** **** **** | 0422 | | KTEST | S | |
| 16B | 0 1111 1111 1111 | 0423 | | BO | OP4C | ROUND OFF |
| 16C | 1 0111 0010 0110 | 0424 | | AAKA | MLSD5 | ROUND UP |
| 16D | 1 0101 0101 0110 | 0425 | | SAKA | MLSD1 | |
| 16E | 0 **** **** **** | 0426 | OP4C | AAKA | MLSD5 | NEWLY CREATED OV OR PSEUDO OV |
| 16F | 1 0111 1110 0110 | 0427 | | BZ | OP4D | |
| 170 | 1 1111 1011 0110 | 0428 | OP4B | SRLA | MANT | |
| 171 | 1 1111 1011 1110 | 0429 | OP4A | TF | BNUM | DETERMINING IF YOU NEED TO GET RID OF TRAILING 0 OR NOT |
| 172 | 1 1111 0011 1100 | 0430 | | TF | AOV | |
| 173 | 1 1111 1011 1100 | 0431 | | ZF | BNUM | |
| 174 | 0 **** **** **** | 0432 | | BZ | OP4 | |
| 175 | 1 1011 1010 0001 | 0433 | R5 | CAK | LLSD1 | |
| 176 | 1 **** **** **** | 0434 | | BO | OP4 | |
| 177 | 1 1000 1010 0001 | 0435 | | CAK | DPT1 | |
| 178 | 0 **** **** **** | 0436 | | BZ | OP4 | |
| 179 | 1 0100 1110 0110 | 0437 | | SRLA | MANT | |
| 17A | 1 1000 1010 0110 | 0438 | | SAKA | DPT1 | |
| 17B | 0 1001 0111 0101 | 0439 | | BO | R5 | ALWAYS BRANCH |
| 17C | 1 0001 1110 0110 | 0440 | OP4 | TF | BSIGMA | |
| 17D | 1 1111 1110 0100 | 0441 | | ZF | BSIGMA | |
| 17E | 0 **** **** **** | 0442 | | BZ | OP42 | |
| 17F | 1 1111 0011 1110 | 0443 | | TF | AOV | |
| 180 | 0 **** **** **** | 0444 | | BZ | OP45 | |
| 181 | 1 1111 1110 1110 | 0445 | | TF | BM+ | |
| 182 | 1 1111 1100 1100 | 0446 | OP45 | TF | BM+ | |
| 183 | 1 0001 0100 0011 | 0447 | | BO | OP41 | |
| 184 | 1 1111 1110 0011 | 0448 | OP43 | SF | BSIGMA | |
| 185 | 1 0000 0000 0011 | 0449 | | EXCO | ALL | |
| 186 | 1 1111 1001 1111 | 0450 | | XF | ASC | |
| 187 | 1 1111 1001 0111 | 0451 | | XF | ASEC | |
| 188 | 1 1111 1111 1011 | 0452 | OP42 | SF | BPREZ | |
| | | 0453 | * | | | EXCHANGE A AND C AND THE ASSOCIATE FLAGS |
| | | 0454 | * | | | B SHOULD BE IDENTICAL TO C |

| | | | | |
|---|---|---|---|---|
| 18D | 1 0000 0000 0010 | 0455 | RV | EXAB ALL |
| 18E | 1 1111 1111 1111 | 0456 | | XF ASA |
| 18F | 1 0000 1101 0111 | 0457 | | XF ASEA |
| 18E | 1 0000 0011 1100 | 0458 | | ACKA ALL |
| 18F | 1 1110 0010 1010 | 0459 | | ABKC ALL |
| 190 | 1 1110 0001 1010 | 0460 | | FLAREG3 ALL |
| 191 | 1 1110 1010 0010 | 0461 | | FLAREG4 ALL |
| 192 | 1 1110 1011 1010 | 0462 | | REGFLA3 |
| 193 | 1 1111 1010 1110 | 0463 | | FLBREG8 |
| 194 | 1 1111 1011 1100 | 0464 | | REGFLA4 |
| 195 | 1 1100 1000 1111 | 0465 | E5 | TF BNUM |
| 196 | 1 1111 1011 1100 | 0466 | | ZF BNUM |
| 197 | 1 1111 1111 1110 | 0467 | | BZ A92 |
| 198 | 1 1111 1111 1100 | 0468 | | TF BPRF2 |
| 199 | 1 0001 0011 0001 | 0469 | | ZF BPRF2 |
| 19A | 1 0001 0011 0001 | 0470 | | BZ OP42A |
| 19B | 1 1111 1000 0011 | 0471 | K3 | SF ARV AN RV OR RM HAS ENTERED |
| 19C | 1 0001 0001 1100 | 0472 | | SF BFLT |
| 19D | 1 0000 1000 1111 | 0473 | | BO POST2 ALWAYS BRANCH |
| 19E | 0 0000 1000 1111 | 0474 | ←-----DATA ENTRY PRIME |
| 19F | 1 0000 0000 0010 | 0475 | PU6 | EXAB ALL |
| 1A0 | 1 1111 0111 1100 | 0476 | LOCK3 | ZF AMEMIND |
| 1A1 | 1 0100 1010 1001 | 0477 | | CDK MANT |
| 1A2 | 1 0111 1011 1001 | 0478 | | BO LOCK1 |
| 1A3 | 1 **** **** **** | 0479 | | SF AMEMIND |
| 1A4 | 1 1111 0111 1011 | 0480 | LOCK1 | AAKA DPT SENDING DPT OF ANS. OUT TO ALU FOR DECIMAL POINT DISPLAY |
| 1A5 | 1 1010 0010 0110 | 0481 | | SIDL 15 SETTING IDLE LATCH |
| 1A6 | 1 1110 0100 0010 | 0482 | | WAIT 15 |
| 1A7 | 1 1101 0111 1101 | 0483 | | SCAN NOPQT |
| 1A8 | 1 1110 0111 1011 | 0484 | | BZ LOCK1 CANNOT PUT ANYTHING INBETWEEN |
| 1A9 | 0 0001 1010 0001 | 0485 | | FETCH 1 |
| 1A6 | 1 1110 0111 1001 | 0486 | IDLE | WAIT 15 FETCH AT THIS LOCATION |
| 1A7 | 1 1101 0111 0000 | 0487 | | SCAN NOPQT |
| 1A8 | 0 1001 1010 0110 | 0488 | | BO IDLE |
| 1A9 | 1 1110 0111 1001 | 0489 | | WAIT 15 |
| 1AA | 1 1101 0111 1011 | 0490 | | SCAN P |
| 1AB | 0 **** **** **** | 0491 | | BZ I1 |
| 1AC | 1 0001 0011 1110 | 0492 | | TF AOV |
| 1AD | 0 0001 1010 0001 | 0493 | | BZ LOCK1 LOCK ON ALL KEYS EXCEPT CE,CM,RS,AND CA WHEN RESULT OV |
| 1AE | 1 1110 0111 1001 | 0494 | | WAIT 15 |
| 1AF | 1 1111 0011 1100 | 0495 | | ZF AOV |

| | | | | | | | |
|---|---|---|---|---|---|---|---|
| 1C4 | 1111 1111 1C01 | 0495 | | WAIT | 15 | | |
| 1C5 | 1111 1111 1C01 | 0497 | | SCAN | OPOT | AT DIS IF NOT FOUND ANYTHING | |
| | 1110 1111 1110 | 0498 | | BO | 12 | NOT A FUNCTION KEY | |
| | 1110 1111 1110 | | 17 | ZIDL | | RESETTING IDLE LATCH | |
| 1C7 | 1110 1111 1010 | 0501 | | POUT | | ALWAYS BRANCH | |
| 148 | 0000 0000 1010 | 0502 | | SCAN | 7 | AT DIS | |
| 149 | 0010 1000 0110 | 0503 | | BO | IDLE | NOT FOUND ANYTHING | |
| 14A | 0001 1010 0110 | 0504 | DATA | EXAR | ALL | | |
| 14B | 1001 1010 0110 | 0505 | | CLA | ALL | | |
| 14C | 0010 1010 0110 | 0506 | | RFGA | EXP | | |
| 14D | 1111 1010 0110 | 0507 | | SAKA | EXP1 | | |
| 14E | 1111 1010 0110 | 0508 | | TF | CNUM | NUMBER SWITCH | |
| 14F | 1111 1010 0110 | 0509 | | BZ | R30 | A DP NUMBER | |
| 150 | 0001 0101 0101 | 0510 | DATA2 | SLLA | ALL | | |
| 151 | 0110 0110 0010 | 0511 | DATA1 | FXAR | ALL | | |
| 152 | 0000 0010 0011 | 0512 | | SF | BFLT | A TEMP FLAG | |
| 153 | 1111 1010 0110 | 0513 | | TF | BDATENT | | |
| 154 | 1*** **** **** | 0514 | P2 | RO | P7 | | |
| 155 | 1*** 1010 1111 | 0515 | | TF | BK | | |
| 156 | 1*** 1111 1111 | 0516 | | BZ | P1 | | |
| 157 | 1*** **** **** | 0517 | * | | | ----------A GOES TO C---- | |
| 1C8 | 0000 0100 0100 | 0518 | OP6 | AAKC | ALL | | |
| 1C9 | 1110 0010 0100 | 0519 | | FLAREG9 | | | |
| 1CA | 1110 0010 0010 | 0520 | | REGFL14 | | | |
| 1CB | 1110 0011 1010 | 0521 | | TF | BCURR1 | COMING FROM DIV OR MULT | |
| 1CC | 1111 0100 0100 | 0522 | P1 | ZF | ARV | | |
| 1CD | 0000 1010 0110 | 0523 | | BZ | OP12 | | |
| 1CE | 1110 1100 0100 | 0524 | | CLA | ALL | | |
| 1CF | 1111 0100 0100 | 0525 | | ZF | AA/D | | |
| 1D0 | 1111 0100 0100 | 0526 | | ZF | BDATENT | | |
| 1D1 | 1111 0100 0100 | 0527 | | ZF | ASA | | |
| 1D2 | 1000 1100 0100 | 0528 | | ZF | ASEA | | |
| 1D3 | 1111 0100 0100 | 0529 | P7 | TF | BFLT | A TEMP FLAG | |
| 1D4 | 1000 1010 0110 | 0530 | | RO | LOCK | | |
| 1D5 | 1010 1010 0001 | 0531 | P6 | CAK | MMSD1 | | |
| 1D6 | **** **** **** | 0532 | | BO | P4 | DIGIT OVERFLOW | |
| 1D7 | 1111 1010 0001 | 0533 | | CAK | DPT11 | | |
| 1D4 | **** 1010 0001 | 0534 | | BZ | P5 | | |
| 1D5 | 1111 1110 1011 | 0535 | P4 | SF | AFKR | | |
| 1D6 | 1110 1110 1011 | 0536 | | RO | LOCK | ALWAYS BRANCH | |

| Addr | Bits | | Label | Op | Operand | Comment |
|---|---|---|---|---|---|---|
| 1D7 | 1111 1100 **** 0110 | | | TF | BDPT | |
| 1D8 | 0 1*** 1010 0110 | | | BO | P6 | |
| 1D9 | 1 1000 1010 0110 | | | AAKA | DPT1 | |
| 1DA | 1 1100 0110 0110 | | | SLLA | MANT | |
| 1DB | 1 1111 0100 0100 | | P6 | AABA | MANT | |
| 1DC | 1 1111 1011 0100 | | | ZF | BCURR1 | |
| 1DD | 1 1111 1011 0101 | | | ZF | BCURR2 | |
| 1DE | 1 1111 1000 0100 | | | ZF | BFLT | |
| 1DF | 1 1111 0101 0100 | | | ZF | ATEMP5 | |
| 1E0 | 1 1111 0101 1100 | | | ZF | BM+- | |
| 1E1 | 1 1111 1001 1100 | | | ZF | DPT1 | LSD OF A MADE TO 0 |
| 1E2 | 1 0000 0010 0111 | | | — DOING A PUNCTUATION — | | |
| 1E3 | 1 0100 0110 0110 | | PU1 | AAKB | ALL | |
| 1E4 | 1 1100 1010 0001 | | | SLLA | MANT | |
| 1E5 | 0 1*** **** 0001 | | | CAK | DV1 | |
| 1E6 | 1 1001 1010 0000 | | | BO | PU2 | |
| 1E7 | 1 1*** **** 0000 | | | CAK | DPT11 | |
| 1E8 | 1 1000 0010 0110 | | | BO | PU2 | |
| 1E9 | 1 1001 1110 0110 | | | AAKA | DPT1 | |
| 1EA | 1 1001 1001 0110 | | | BO | PU1 | |
| 1EB | 1 0100 0010 0110 | | PU2 | CLA | MANT | |
| 1EC | 1 1010 0010 0001 | | | AREG | DPT | |
| 1ED | 1 1010 0010 0001 | | | REGB | EXP | |
| 1EE | 1 0011 0000 0110 | | | EXP11A | EXP | |
| 1EF | 1 0010 0000 0110 | | | SABA | EXP | ALWAYS BRANCH |
| 1F0 | 1 0010 1100 0110 | | | CLB | EXP1 | |
| 1F1 | 1 0001 1000 0110 | | | SAKA | EXP1 | |
| 1F2 | 1 0011 1010 0110 | | PU3 | SAKA | EXP1 | |
| 1F3 | 1 0*** 1010 0110 | | | BZ | PU4 | |
| 1F4 | 1 0101 0010 0110 | | | AAKA | MLSD1 | |
| 1F5 | 1 1010 1010 0110 | | | AAKA | MLSD1 | |
| 1F6 | 1 0110 1010 0110 | | | SLLA | MANT | |
| 1F7 | 1 0100 1010 0110 | | | SLLA | MANT | |
| 1F8 | 1 0100 1010 0110 | | | SLLA | MANT | |
| 1F9 | 1 0101 1111 0000 | | | BO | PU3 | ALWAYS BRANCH |
| 1FA | 1 1010 1110 1110 | | PU4 | ARKA | DPT | |
| 1FB | 1 1000 0110 0110 | | | SAKA | DPT1 | |
| 1FC | 0 0001 1001 1100 | | | BZ | PU6 | |
| 1FD | 1 0100 0110 0110 | | PU5 | SLLA | MANT | |
| 1FE | 0 1111 1111 1C01 | | | BO | PU5 | ALWAYS BRANCH |

TABLE VII

```
1E4503C71E9A1F801144F1F0010961084082F1FA61FAE01C61FEE01721F6415A1087E
10861F4C1F8829771F401F5D1FE9083E1F931F591DDF1E22002010241E2A1E9A1E32
1030E1F631F66084013651201LEAA08481FC409CA14E619A6090E1FC41A861F3C09DE
1FB31FF31F7609C61F66000A08091F4D1F511DDF001711F661F76030E1FA60B0C1FEE
1FEC034A1F5E01721F1C1FF71F071FA31FC409DE1826102C1EA21E2A1FF60B551FAC
1F6603541FAE01121F741CB10050014F415A10995108611F4C09951826182A1F43080F
1FC309C21F4D1F831F9B09721B2419A1C0721A46114E6086D182609DE1F56088911A1
00B611AC097E1826164A10B7414661FDE010919A1007A16A1C813146661F56008908876
1F591126037E1F23347E1FFE1FF00B80F1FE61F2E1F2C00961F7600C01221F5700A6
12C1080D10021FCF12C41F56094210021FCF11B4008014EF08A21FD600AB10021FCF
1FD715A10DA81244C0B909A214C108B410021FCF1F4F00B814C6088914461204F1FB6
0B501F0D091001002C09C41F3609C91FAE00BE1FCF1F0715A1012310021FAC1E591CDF
08CE1FAB91F4F1F4C090021F4B1F5708F51F3600FA124608091F2315A1004F14241486
1F3609EC140101041404152608DF14F41581004F10F4158110740010F14E6168400E4
144603FC14E419A6140F1C260BEC1F36000612C108FA1F5512C409021002120410002
1F36090521F55123605D91CA10B4E15A11FDB00A51FDC14661581010410147408DF146F
18760BEC1F28085A136091714E611A109010F1F26903321F2411A609E1F560116134A1
011413A51F3B091710021AC1100209511A4E619A609251F9E0D10E1FAE1F6600480849
1F541FB61F3E1FF6013C1E711D6F1FBB018911FBC1F8319D21306310E61AC11002012A
1CA10940P1AC1095F1466182609431C061B46C095F19A618A618A609231F76095F1FB6
1FE6E79109F015E1DDF095C17261A5A61726014A14E61FBE1F3E1FBC016A1BA1096A
1BA1016A14E51BA609631FE61FE401761F3E01701FEE1FEC092C1FE310031F8F1F97
1FEFD0021FCF1FD7103510002C1E221E1A1F321EA21E2A1FBE1FBC00B801FFE1FFC018A
1F631F23071171FE6000F10031F8F1F971FEE1FFC000F1F9E09951F8311A101191F56
091C11A61826091710021F7C14B909A11F781A261E421E791D3C01A11E791D300946
1E511DF01F791D78010B01F3E01A11F3C1E791D3103B61E4A1E3A1D7E09A61E441002
1086120511A61FBE01B106610021F831FA609D11FAE01CA10241E221C2A1FF61F64
004910241F2C1F4A1F4C1F541FB4A09DE16A10907191A101091F3B09DE1FC609DC1826
144614441FF41F841F341F50C1F9C10271466114CA10959112A109FB1926609E414861A21
120713061286123711A511A611A501FB1466152415261466146609F11A2E18A6019C
14660DFC0000000000000000000000000000000000000000000000000000000000
```

TABLE VIII  THE INSTRUCTION WORDS AT ROM LOCATIONS

| | 479 | 480 | 481 | 482 | 483 | 484 | 485 | 486 | 487 | 488 | 489 | 490 | 491 | 492 | 493 | 494 | 495 | 496 | 497 | 498 | 499 | 500 | 501 | 502 | 503 | 504 | 505 | 506 | 507 | 508 | 509 | 510 | 511 |
|---|---|---|---|---|---|---|---|---|---|---|---|---|---|---|---|---|---|---|---|---|---|---|---|---|---|---|---|---|---|---|---|---|---|
| | 0 | 0 | 0 | 0 | 0 | 1 | 0 | 1 | 1 | 1 | 1 | 0 | 0 | 0 | 1 | 0 | 0 | 1 | 0 | 0 | 0 | 1 | 0 | 0 | 0 | 0 | 0 | 1 | 0 | 0 | 0 | 0 | 0 |
| | 0 | 0 | 0 | 0 | 1 | 1 | 0 | 1 | 0 | 1 | 1 | 0 | 1 | 0 | 1 | 1 | 1 | 1 | 1 | 1 | 1 | 1 | 1 | 1 | 1 | 0 | 1 | 1 | 0 | 1 | 0 | 1 | 0 |
| | 1 | 1 | 1 | 1 | 1 | 0 | 0 | 0 | 0 | 1 | 1 | 1 | 0 | 1 | 1 | 1 | 1 | 1 | 1 | 0 | 1 | 1 | 1 | 1 | 1 | 0 | 1 | 1 | 1 | 1 | 1 | 1 | 1 |
| | 0 | 0 | 1 | 1 | 0 | 0 | 0 | 1 | 0 | 1 | 0 | 0 | 0 | 0 | 0 | 0 | 0 | 0 | 0 | 1 | 0 | 0 | 0 | 0 | 0 | 0 | 1 | 0 | 1 | 0 | 1 | 0 | 1 |
| | 1 | 0 | 1 | 1 | 0 | 0 | 0 | 0 | 0 | 0 | 0 | 0 | 0 | 0 | 0 | 0 | 0 | 0 | 0 | 1 | 0 | 0 | 0 | 0 | 0 | 1 | 0 | 0 | 1 | 0 | 1 |
| | 1 | 0 | 0 | 0 | 1 | 1 | 1 | 1 | 1 | 1 | 1 | 0 | 1 | 0 | 0 | 0 | 0 | 1 | 1 | 1 | 1 | 1 | 1 | 1 | 1 | 1 | 1 | 1 | 1 | 0 | 1 | 1 |
| | 0 | 0 | 1 | 0 | 0 | 1 | 0 | 1 | 0 | 1 | 0 | 1 | 0 | 0 | 0 | 0 | 1 | 0 | 0 | 0 | 0 | 1 | 1 | 0 | 0 | 1 | 1 | 1 | 0 | 0 | 0 | 1 | 1 |
| | 1 | 1 | 0 | 1 | 0 | 0 | 1 | 1 | 1 | 1 | 0 | 1 | 1 | 1 | 0 | 0 | 0 | 1 | 1 | 1 | 1 | 1 | 1 | 0 | 0 | 0 | 0 | 0 | 1 | 0 | 1 | 1 | 0 | 1 |
| | 1 | 1 | 1 | 1 | 0 | 0 | 0 | 1 | 1 | 1 | 0 | 1 | 0 | 0 | 0 | 1 | 0 | 0 | 1 | 1 | 1 | 1 | 1 | 0 | 1 | 1 | 0 | 0 | 1 | 0 | 0 | 1 | 0 | 1 |
| | 1 | 1 | 1 | 1 | 0 | 0 | 0 | 0 | 0 | 0 | 0 | 0 | 0 | 1 | 1 | 1 | 1 | 1 | 0 | 0 | 0 | 0 | 0 | 0 | 0 | 0 | 0 | 0 | 1 | 0 | 0 | 0 | 0 |
| | 1 | 1 | 1 | 1 | 0 | 1 | 1 | 0 | 0 | 0 | 0 | 0 | 1 | 0 | 0 | 0 | 0 | 0 | 0 | 0 | 0 | 0 | 0 | 1 | 1 | 1 | 1 | 1 | 0 | 0 | 0 | 1 | 0 |
| | 1 | 1 | 1 | 1 | 0 | 0 | 1 | 1 | 1 | 1 | 1 | 0 | 1 | 0 | 0 | 0 | 0 | 0 | 0 | 0 | 0 | 0 | 0 | 0 | 0 | 0 | 1 | 1 | 1 | 1 | 0 | 0 | 1 |
| | 1 | 1 | 1 | 1 | 1 | 1 | 1 | 1 | 0 | 1 | 0 | 1 | 0 | 1 | 1 | 1 | 1 | 1 | 1 | 1 | 1 | 0 | 1 | 1 | 1 | 1 | 1 | 0 | 1 | 1 | 0 | 1 | 0 |

| | 223 | 224 | 225 | 226 | 227 | 228 | 229 | 230 | 231 | 232 | 233 | 234 | 235 | 236 | 237 | 238 | 239 | 240 | 241 | 242 | 243 | 244 | 245 | 246 | 247 | 248 | 249 | 250 | 251 | 252 | 253 | 254 | 255 |
|---|---|---|---|---|---|---|---|---|---|---|---|---|---|---|---|---|---|---|---|---|---|---|---|---|---|---|---|---|---|---|---|---|---|
| | 1 | 0 | 0 | 0 | 1 | 0 | 1 | 1 | 0 | 1 | 0 | 1 | 0 | 0 | 0 | 0 | 0 | 0 | 0 | 1 | 0 | 0 | 0 | 0 | 1 | 0 | 1 | 0 | 0 | 0 | 0 | 0 | 0 |
| | 0 | 0 | 0 | 1 | 1 | 0 | 0 | 1 | 0 | 0 | 0 | 1 | 1 | 0 | 0 | 1 | 0 | 1 | 0 | 1 | 1 | 1 | 0 | 1 | 1 | 0 | 1 | 0 | 0 | 1 | 1 | 0 | 1 |
| | 0 | 1 | 1 | 1 | 1 | 1 | 0 | 1 | 0 | 1 | 1 | 1 | 1 | 1 | 1 | 1 | 1 | 1 | 1 | 1 | 1 | 1 | 1 | 0 | 0 | 1 | 1 | 0 | 0 | 1 | 0 | 1 |
| | 0 | 0 | 0 | 0 | 1 | 0 | 0 | 1 | 0 | 0 | 0 | 1 | 0 | 0 | 0 | 1 | 0 | 0 | 1 | 0 | 1 | 0 | 0 | 0 | 1 | 0 | 0 | 0 | 0 | 0 | 0 |
| | 1 | 0 | 1 | 0 | 1 | 1 | 1 | 0 | 1 | 1 | 1 | 0 | 0 | 1 | 0 | 0 | 0 | 0 | 0 | 0 | 0 | 1 | 1 | 0 | 1 | 1 | 0 | 0 | 0 | 0 | 1 |
| | 0 | 0 | 0 | 1 | 0 | 1 | 1 | 0 | 1 | 1 | 0 | 1 | 1 | 0 | 1 | 1 | 1 | 1 | 1 | 1 | 1 | 0 | 0 | 1 | 0 | 0 | 0 | 0 | 0 | 1 |
| | 1 | 0 | 1 | 0 | 1 | 1 | 0 | 1 | 1 | 0 | 1 | 0 | 1 | 1 | 1 | 1 | 1 | 0 | 1 | 0 | 1 | 1 | 1 | 1 | 0 | 0 | 1 | 0 | 0 |
| | 1 | 0 | 1 | 0 | 1 | 1 | 1 | 0 | 1 | 1 | 0 | 0 | 1 | 1 | 1 | 0 | 1 | 1 | 0 | 1 | 0 | 1 | 1 | 1 | 0 | 1 | 0 | 0 | 1 | 0 |
| | 0 | 1 | 0 | 1 | 0 | 0 | 1 | 0 | 0 | 1 | 0 | 1 | 0 | 1 | 0 | 0 | 0 | 0 | 0 | 0 | 0 | 1 | 0 | 0 | 0 | 1 | 0 | 1 | 0 | 0 | 1 |
| | 0 | 0 | 0 | 0 | 0 | 0 | 0 | 0 | 0 | 0 | 0 | 0 | 1 | 0 | 0 | 0 | 0 | 0 | 0 | 0 | 0 | 1 | 0 | 1 | 0 | 1 | 1 | 0 | 0 | 1 | 0 | 1 |
| | 1 | 0 | 1 | 1 | 0 | 1 | 1 | 0 | 0 | 1 | 0 | 0 | 0 | 0 | 0 | 1 | 0 | 1 | 0 | 1 | 1 | 0 | 1 | 0 | 0 | 0 | 1 | 0 | 0 | 0 | 0 | 1 |
| | 0 | 0 | 0 | 0 | 1 | 0 | 0 | 0 | 0 | 0 | 0 | 0 | 0 | 1 | 0 | 0 | 1 | 0 | 1 | 1 | 1 | 1 | 0 | 0 | 1 | 0 | 1 | 0 | 0 | 0 | 1 |
| | 1 | 0 | 1 | 1 | 0 | 1 | 1 | 0 | 1 | 0 | 1 | 1 | 1 | 0 | 1 | 0 | 1 | 1 | 1 | 1 | 0 | 1 | 0 | 1 | 0 | 1 | 1 | 0 | 1 | 1 | 1 | 1 |

TABLE IX. THE ROM. GATES ARE X's

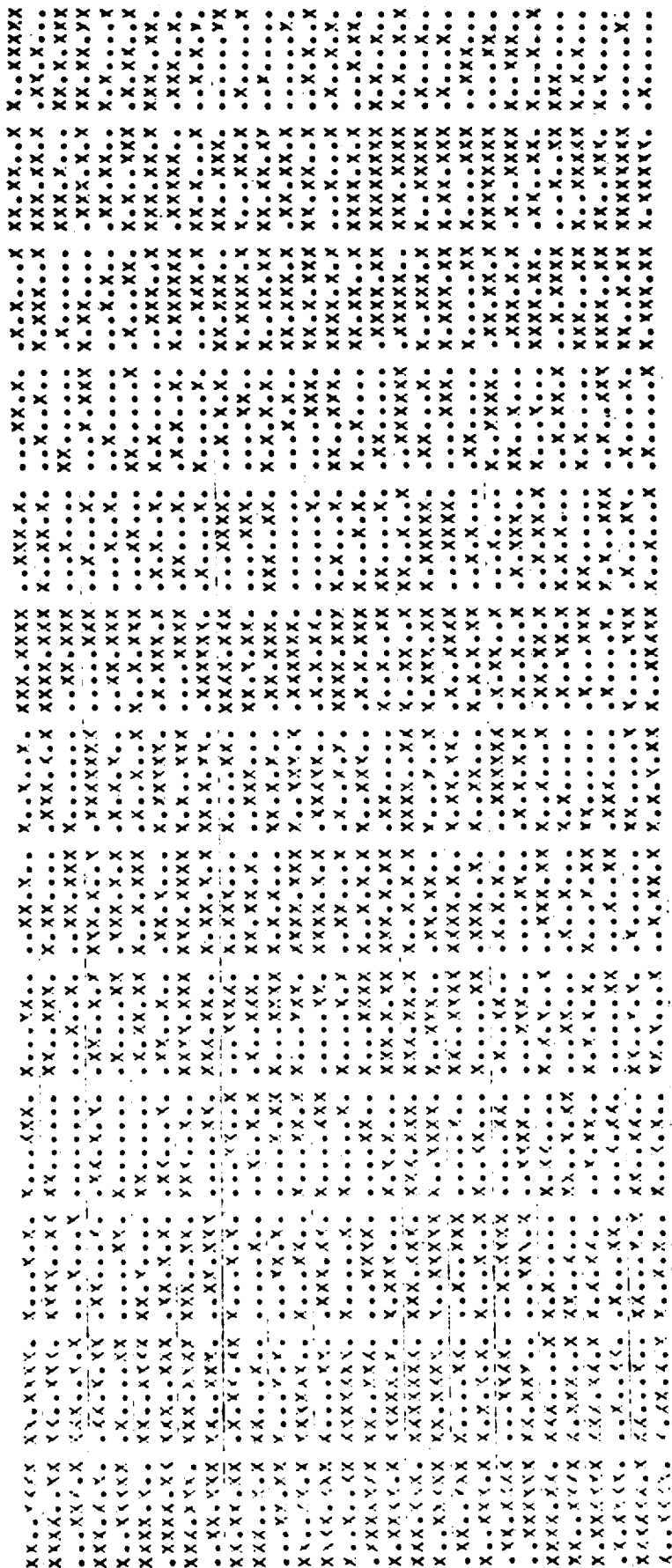

What is claimed is:

1. An electronic calculator comprising:
(a) keyboard input means for entering data and functions;
(b) addressable memory means defining a plurality of data registers, and means for storing in specific addressed locations in the data registers in bit-parallel format a plurality of multi-digit words of binary coded decimal information, the digits of the multi-digit words remaining in specific locations of the addressable memory means until addressed;
(c) means for addressing the memory means for shifting the words out of each register one digit at a time in bit parallel fashion;
(d) addressable storage means for storing a large number of program instructions;
(e) decoder means receiving said program instructions and generating command signals according to the program instructions;
(f) a plurality of logic devices connected to receive and be operated by said command signals;
(g) bit parallel arithmetic logic means connected via the logic devices to the data registers for performing parallel arithmetic and logic operation on said multidigit coded words as shifted out one digit at a time, as commanded by the command signals, and for producing an output, for applying the resulting words from said output of the arithmetic logic means to said means for storing via the logic devices whereby the resulting words are stored in specific addressed locations in one of the data registers;
(h) display output means connected to the storage means via the logic devices for displaying the resulting words as stored in said one of the data registers;
(i) timing means for producing timing signals for sequentially addressing corresponding digits of each of the data registers one digit at a time from least to most significant digit;
(j) means connected to receive a plurality of the timing signals addressing the data registers and producing therefrom encoded timing signals; and
(k) means for generating scanning controls for the keyboard input means and the display output means in response to said encoded timing signals.

2. An electronic calculator according to claim 1 wherein said data registers include addressable memory means comprising:
(a) a random access memory array having rows and columns of memory cells, each of said memory cells including:
  (i) input means for introducing a bit of information into the memory cell;
  (ii) output means for reading information out of the memory cell;
  (iii) read and write control means for addressing the memory cell in order to read information out of the memory cell to the output means and to write information into the memory cell from the input means; and
(b) the timing means comprising commutator means selectively coupled to said read and write control means for selectively applying address signals to the read and write control means of the rows of memory cells.

3. An electronic calculator according to claim 2 wherein the read and write control means of adjacent cells are in common, and means for applying the address signals to the control means one at a time, so at a given time bits from one digit from each of the plurality of multidigit words are read out of a given row of cells while bits from each of the plurality of multidigit words are being written into the preceding row of cells.

4. An electronic calculator according to claim 1 wherein each of the data registers includes N characters, where N is an integer, and memory cells of the data registers are cyclically addressed for one bit time during a word time of N bit times, the scanning controls for the keyboard input means operating in cycles of N bit times.

5. An electronic calculator according to claim 4 wherein the keyboard input means includes means for providing encoded words having timing information and key location information.

6. An electronic calculator according to claim 5 wherein means are provided for using the encoded words for selecting an address in the addressable storage means.

7. An electronic calculator according to claim 6 wherein the keyboard input means includes an interface register, and means are provided for generating said timing information from said encoded timing signals.

8. An electronic calculator comprising:
(a) memory means providing a plurality of data registers of N bits for storing a plurality of words, where N is an integer;
(b) addressable fixed storage means for storing a plurality of program instructions;
(c) decoder means receiving the program instructions and generating command signals; logic means connected to receive command signals and defining interconnections within the calculator according to the instructions;
(d) program address means coupled to the fixed storage means for selecting specific addresses therein for program
(e) means responsive to said keyboard scan signals and for generating keyboard scan signals;
(f) keyboard input means having number keys and operation keys for producing encoded words representing keys punched and also representing said keyboard scan signals; and
(g) means for presenting said encoded words to the program address means to thereby select an address dependent upon the keyboard input.

9. An electronic calculator according to claim 7 wherein means are provided for cyclically addressing registers in parallel with each bit being addressed for one state time for every N state times, and wherein the time signals for the keyboard input means are of N state times in length.

10. An electronic calculator according to claim 9 wherein the keyboard input means includes means for scanning the keyboard in a time period of N(N-1) state times.

11. An electronic calculator according to claim 8 wherein an interface register is provided for receiving said encoded words and transmitting the encoded words to the program address means.

12. An electronic calculator according to claim 11 wherein the interface register includes a first part for receiving encoded keyboard sense line information and a second part for receiving encoded time information.

13. An electronic calculator according to claim 8 wherein the memory means providing the data registers is a random access memory array having rows and columns of memory cells with common column address lines for adjacent cells in a row, and commutator means is provided for selectively addressing such lines.

14. An electronic calculator according to claim 13 wherein the timing signals in said encoded words in the keyboard input means are generated from said commutator means.

15. An electronic calculator according to claim 14 wherein the commutator means cyclically addresses the address lines, in a time period of N bit times, and the keyboad input means includes scanning the keyboard in a time period of N(N-1) bit times.

16. A digital electronic system implemented in at least two complex special-purpose semiconductor integrated circuit units, a first of such units containing memory means for storing numerical data and containing arithmetic means coupled to the memory means for operating on the data, decoder control means included in said first unit generating command signals, logic means included in the first unit connected to receive command signals and defining interconnections for controlling the operation performed in the arithmetic means and defining connections between the memory means and the arithmetic means, a second of such units containing a permanent store memory for storing a plurality of said instruction words and containing addressing means for selecting instruction words to be transmitted to the first unit, storage means in the first unit for receiving said instruction words from the second unit, the decoder means receiving an instruction word temporarily stored in said storage means, means in said first unit for generating control instructions for transmitting to the addressing means in the second unit, means in the first unit for generating timing signals and encoded timing signals, input means including a keyboard having an array of key switches and including means responsive to said timing signals for scanning the switches in groups and for encoding signals generated by closure of key switches, the means for generating control instructions being responsive to the encoded timing signals and encoded key switch signals.

17. A digital electronic calculator system according to claim 16 wherein the memory means comprises a sequentially addressed random access memory array organized in bit parallel serial digit binary coded decimal format with a plurality of data words of N digits in length, where N is an integer, and the arithmetic means is of bit parallel form.

18. A digital electronic calculator system according to claim 16 and further including means in one of the units other than the first unit for generating a plurality of timing signals for operation of parts of such other unit, in response to timing signals generated in the first unit and transmitted to such other unit.

19. A digital electronic calculator system according to claim 16 and further including means for generating a signal in the first unit which gives one indication when the key switches are being scanned and gives another indication when an operation is being performed in the arithmetic unit, and means are provided for transmitting the signal to another of the units.

20. An electronic data processor comprising:
(a) data storage means providing a plurality of data registers for storing a plurality of words;
(b) addressable fixed storage means for storing a plurality of program instructions each of which defines a specific operating condition of the data processor;
(c) control means which includes decode means for receiving the program instructions and generating command signals, and which further includes a plurality of logic devices receiving the command signals and providing an operation condition defined according to the instructions;
(d) program address means coupled to the fixed storage means for selecting specific addresses therein as program instructions;
(e) an input array;
(f) means for generating scan signals and applying said scan signals to the input array;
(g) input means responsive to said scan signals and having input lines for producing encoded words representing particular input lines actuated and said scan signals, the input means including number inputs and operation inputs; and
(h) means for presenting said encoded words to the program address means for selecting an address dependent upon the encoded words.

21. An electronic data processor according to claim 20 wherein said input means includes a keyboard having number keys and operation keys coupled to said input lines and further including an interface register coupled to said keyboard for receiving said encoded words and transmitting the encoded words to the program address means.

22. An electronic data processor according to claim 21 and including means for alternatively transmitting said encoded words from the interface register to the data registers.

23. An electronic data processor according to claim 22 and including means coupled to said data storage means and responsive to timing signals addressing said data storage means for generating therefrom encoded timing signals.

24. The electronic data processor according to claim 23 wherein said data storage means and said means for generating timing signals are implemented on one semiconductor chip and further including means for outputting said encoded timing signals to another semiconductor chip.

25. In an electronic calculator of the type implemented on at least one semiconductor integrated circuit chip, the calculator having addressable means for storing a plurality of instruction words, a keyboard entry and address generating system comprising:
(a) a keyboard array having rows and columns of keys;
(b) means for generating timing signals which define instruction cycles in the calculator;
(c) means responsive to said timing signals for storbing said rows of said keyboard array;
(d) means for monitoring said columns in said array and for producing output signals representing actuation of keys;
(e) means for encoding said timing signals into a first coded format;
(f) means for encoding said output signals from said means for monitoring said columns in a second coded format; and
(g) means for storing said first and second coded formats, the stored first and second coded formats in combination defining an instruction word address, and means responsive to said first and second coded formats for addressing said addressable means.

26. The keyboard entry system of claim 25 wherein said first and second formats are stored in serial format to define said address and including means for incrementing said serial format by one bit so as to increment said address by one.

27. The keyboard entry system of claim 26 wherein said address is communicated from said means for storing to another semi-conductor chip and further including on said one chip:
   (a) an output means; and
   (b) means coupling said output means and said storage means for communicating said stored address to said output means at a preselected time during an instruction cycle.

28. An electronic processor comprising:
a keyboard array having rows and columns of key switches;
display means having a plurality of inputs;
scanning means for actuating in a predetermined sequence rows of the keyboard array and simultaneously actuating inputs of the display means;
means coupled to the scanning means for providing a first multi-bit representation of the particular one of said rows and inputs which is actuated at a given time;
keyboard input means coupled to the columns of key switches to provide a second multi-bit representation dependent upon keys actuated;
control means connected to receive the first and second multi-bit representations and generating command signals in response thereto; and
a plurality of logic devices in said electronic processor responsive to said command signals and functioning to define operating conditions in the processor.

29. An electronic calculator according to claim 28 wherein the control means includes a ready-only-memory containing a plurality of instruction words, and wherein the first and second multi-bit representations are used to generate an address for selecting instruction words in said read-only-memory.

30. An electronic processor according to claim 27 wherein the control means produces said command signals in response to the instruction words selected according to said address.

31. An electronic processor according to claim 28 wherein the display has a plurality of digits and the scanning means actuates the digits of the display repetitively in sequence beginning with the most significant digit.

32. An electronic processor according to claim 28 wherein the first and second representations are encoded representations.

33. An electronic processor comprising:
an array of key switches having a plurality of input terminals and a plurality of output terminals;
display means having a plurality of inputs;
scanning means for actuating in a preselected sequence certain ones of the inputs of the display means while at the same time actuating corresponding ones of the input terminals of the array in said preselected sequence;
means including in the scanning means for providing a first multi-bit representation of the particular one of said inputs of the display means which is activated at a given time;
input means coupled to the output terminals of the array to provide a second multi-bit representation of closure of key switches;
control means responsive to the first and second multi-bit representations to provide control signals; and
a plurality of logic devices in the electronic processor responsive to the control signals and functioning to define operating conditions in the processor.

34. An electronic processor according to claim 33 wherein the control means includes a read-only-memory containing a plurality of instruction words, and wherein the first and second multi-bit representations are used to generate an address for selecting instruction words in said read-only-memory.

35. An electronic processor according to claim 33 wherein the first and second representations are encoded representations.

* * * * *